United States Patent
Yu et al.

(10) Patent No.: US 11,041,017 B2
(45) Date of Patent: Jun. 22, 2021

(54) ANTIBODIES, PHARMACEUTICAL COMPOSITIONS AND METHODS

(71) Applicant: OBI Pharma, Inc., Taipei (TW)

(72) Inventors: Cheng-Der Tony Yu, Taipei (TW); Jiann-Shiun Lai, Taipei (TW); I-Ju Chen, Taipei (TW); Chiu-Chun Lin, Taipei (TW)

(73) Assignee: OBI Pharma, Inc., Taipei (TW)

( * ) Notice: Subject to any disclaimer, the term of this patent is extended or adjusted under 35 U.S.C. 154(b) by 264 days.

(21) Appl. No.: 15/473,267

(22) Filed: Mar. 29, 2017

(65) Prior Publication Data
US 2017/0283488 A1 Oct. 5, 2017

Related U.S. Application Data

(60) Provisional application No. 62/314,841, filed on Mar. 29, 2016.

(51) Int. Cl.

| C07K 16/00 | (2006.01) |
| *A61K 39/395* | (2006.01) |
| *C07K 16/18* | (2006.01) |
| *G01N 33/92* | (2006.01) |
| *C07K 16/44* | (2006.01) |
| *G01N 33/574* | (2006.01) |
| *A61P 35/00* | (2006.01) |
| *A61K 39/00* | (2006.01) |

(52) U.S. Cl.
CPC .............. *C07K 16/18* (2013.01); *A61P 35/00* (2018.01); *C07K 16/44* (2013.01); *G01N 33/57438* (2013.01); *G01N 33/92* (2013.01); *A61K 2039/505* (2013.01); *A61K 2039/507* (2013.01); *G01N 2400/00* (2013.01); *G01N 2405/10* (2013.01)

(58) Field of Classification Search
None
See application file for complete search history.

(56) References Cited

U.S. PATENT DOCUMENTS

| 3,773,919 A | 11/1973 | Boswell et al. |
| RE30,985 E | 6/1982 | Cartaya |
| 4,419,446 A | 12/1983 | Howley et al. |
| 4,522,811 A | 6/1985 | Eppstein et al. |
| 4,560,655 A | 12/1985 | Baker |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,849,222 A | 7/1989 | Broaddus |
| 4,927,762 A | 5/1990 | Darfler |
| 4,943,533 A | 7/1990 | Mendelsohn et al. |
| 4,965,199 A | 10/1990 | Capon et al. |
| 4,975,278 A | 12/1990 | Senter et al. |
| 5,004,697 A | 4/1991 | Pardridge |
| 5,057,540 A | 10/1991 | Kensil et al. |
| 5,061,620 A | 10/1991 | Tsukamoto et al. |
| 5,100,669 A | 3/1992 | Hyon et al. |
| 5,112,596 A | 5/1992 | Malfroy-Camine |
| 5,122,469 A | 6/1992 | Mather et al. |
| 5,212,290 A | 5/1993 | Vogelstein et al. |
| 5,264,365 A | 11/1993 | Georgiou et al. |
| 5,268,164 A | 12/1993 | Kozarich et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,894 A | 11/1996 | Wels et al. |

(Continued)

FOREIGN PATENT DOCUMENTS

| CN | 1871025 A | 11/2006 |
| CN | 103108654 A | 5/2013 |

(Continued)

OTHER PUBLICATIONS

Paul, Fundamental Immunology, 3rd Edition, p. 292-295, 1993.*
Rudikoff et al, Proc. Natl. Acad. Sci. USA, 79:1979-1983,1982.*
Colman P. M. Research in Immunology, 145:33-36, 1994.*
Pascalis et al, Journal of Immunology, 169: 3076-3084, 2002.*
Casset et al, Biochemical and Biophysical Research Communications, 307:198-205, 2003.*
Vajdos et al, Journal of Molecular Biology, 320:415-428, 2002.*
Holm et al, Molecular Immunology, 44:1075-1084, 2007.*
Barbas, C.F. et al., "Semisynthetic combinatorial antibody libraries: a chemical solution to the diversity problem" Proc. Natl. Acad. Sci. USA, May 15, 1992, 89(10): 4457-4461.

(Continued)

*Primary Examiner* — Mark Halvorson
(74) *Attorney, Agent, or Firm* — Prosyla Group PC

(57) ABSTRACT

Pharmaceutical composition comprising antibodies or antigen binding fragments thereof that bind to stage-specific embryonic antigen 4 (SSEA-4) are disclosed herein, as well as methods of use thereof. Methods of use include, without limitation, cancer therapies and diagnostics. The antibodies of the disclosure can bind to certain cancer cell surfaces. Exemplary targets of the antibodies disclosed herein can include carcinomas, such as breast cancer, lung cancer, esophageal cancer, rectal cancer, biliary cancer, liver cancer, buccal cancer, gastric cancer, colon cancer, nasopharyngeal cancer, kidney cancer, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer, basal cell carcinoma, squamous cell carcinoma, melanoma, and/or brain tumor.

33 Claims, 14 Drawing Sheets
(11 of 14 Drawing Sheet(s) Filed in Color)
Specification includes a Sequence Listing.

(56) References Cited

U.S. PATENT DOCUMENTS

| | | |
|---|---|---|
| 5,580,717 A | 12/1996 | Dower et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,686,416 A | 11/1997 | Kozarich et al. |
| 5,733,743 A | 3/1998 | Johnson et al. |
| 5,804,396 A | 9/1998 | Plowman |
| 5,814,344 A | 9/1998 | Tice et al. |
| 5,821,337 A | 10/1998 | Carter et al. |
| 5,840,523 A | 11/1998 | Simmons et al. |
| 5,849,906 A | 12/1998 | Cavalieri et al. |
| 5,869,046 A | 2/1999 | Presta et al. |
| 5,891,996 A | 4/1999 | Mateo de Acosta del Rio et al. |
| 6,004,940 A | 12/1999 | Marasco et al. |
| 6,027,888 A | 2/2000 | Georgiou et al. |
| 6,083,715 A | 7/2000 | Georgiou et al. |
| 6,265,150 B1 | 7/2001 | Terstappen et al. |
| 6,329,173 B1 | 12/2001 | Marasco et al. |
| 6,524,584 B2 | 2/2003 | Kensil |
| 6,544,952 B1 | 4/2003 | Danishefsky et al. |
| 6,703,019 B1 | 3/2004 | Malfroy-Camine |
| 7,595,292 B2 | 9/2009 | Brocchini et al. |
| 8,268,969 B2 | 9/2012 | Wong et al. |
| 9,850,473 B2 | 12/2017 | Wang |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0129186 A1 | 7/2003 | Beliveau et al. |
| 2003/0153492 A1 | 8/2003 | Danishefsky et al. |
| 2003/0162695 A1 | 8/2003 | Schatzberg et al. |
| 2004/0018194 A1 | 1/2004 | Francisco et al. |
| 2004/0131692 A1 | 7/2004 | Kreuter et al. |
| 2004/0204354 A1 | 10/2004 | Nelson et al. |
| 2004/0208884 A1 | 10/2004 | Danishefsky et al. |
| 2004/0229310 A1 | 11/2004 | Simmons |
| 2004/0247608 A1 | 12/2004 | Krantz et al. |
| 2005/0048572 A1 | 3/2005 | Reilly et al. |
| 2005/0089473 A1 | 4/2005 | Black et al. |
| 2005/0124533 A1 | 6/2005 | Schatzberg et al. |
| 2006/0035267 A1 | 2/2006 | Livingston et al. |
| 2007/0059769 A1 | 3/2007 | Blixt et al. |
| 2009/0317411 A1 | 12/2009 | Wong et al. |
| 2010/0136042 A1 | 6/2010 | Wong et al. |
| 2010/0166790 A1 | 7/2010 | Agadjanyan et al. |
| 2010/0286035 A1 | 11/2010 | Ohtaki et al. |
| 2011/0117009 A1 | 5/2011 | Kratz et al. |
| 2012/0237532 A1 | 9/2012 | Olbrich et al. |
| 2012/0294859 A1 | 11/2012 | Goletz et al. |
| 2012/0321583 A1 | 12/2012 | Yurkovetskiy et al. |
| 2012/0328646 A1 | 12/2012 | Wong et al. |
| 2013/0095173 A1 | 4/2013 | Danishefsky et al. |
| 2013/0232589 A1* | 9/2013 | Papkoff ............ A61K 39/39558 800/18 |
| 2014/0363455 A1* | 12/2014 | Stull ................. A61K 47/6855 424/181.1 |
| 2015/0030669 A1 | 1/2015 | Platscher et al. |
| 2015/0079090 A1 | 3/2015 | Sato et al. |
| 2015/0087814 A1 | 3/2015 | Wang et al. |
| 2015/0297696 A1 | 10/2015 | Yu et al. |
| 2015/0316556 A1 | 11/2015 | Hardt et al. |
| 2015/0344551 A1 | 12/2015 | Wong et al. |
| 2016/0074522 A1 | 3/2016 | Okuda et al. |
| 2016/0102151 A1 | 4/2016 | Wong et al. |
| 2016/0339089 A1 | 11/2016 | Yu et al. |
| 2017/0067885 A1 | 3/2017 | Yu et al. |
| 2017/0101462 A1 | 4/2017 | Yu et al. |
| 2017/0283488 A1 | 10/2017 | Yu et al. |
| 2017/0283489 A1 | 10/2017 | Bosio et al. |
| 2017/0304419 A1 | 10/2017 | Yu et al. |
| 2017/0335281 A1 | 11/2017 | Loew et al. |
| 2018/0028629 A1 | 2/2018 | Yu et al. |
| 2018/0193481 A1 | 7/2018 | Chang et al. |
| 2018/0208915 A1 | 7/2018 | Kawaguchi et al. |
| 2018/0291109 A1 | 10/2018 | Lin et al. |
| 2018/0339061 A1 | 11/2018 | Yu et al. |

FOREIGN PATENT DOCUMENTS

| | | |
|---|---|---|
| EP | 0404097 A2 | 12/1990 |
| EP | 1391213 A1 | 2/2004 |
| EP | 2993182 A1 | 3/2016 |
| JP | 2006-507233 A | 3/2006 |
| KR | 10-2012-0014238 A | 2/2012 |
| WO | WO 87/00195 A1 | 1/1987 |
| WO | WO 90/03184 A1 | 4/1990 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/09690 A2 | 6/1992 |
| WO | WO 93/01161 A1 | 1/1993 |
| WO | WO 93/06213 A1 | 4/1993 |
| WO | WO 93/007861 A1 | 4/1993 |
| WO | WO 93/08829 A1 | 5/1993 |
| WO | WO 93/16185 A2 | 8/1993 |
| WO | WO 94/04690 A1 | 3/1994 |
| WO | WO-1994/011026 A2 | 5/1994 |
| WO | WO 95/011010 A1 | 4/1995 |
| WO | WO 96/07754 A1 | 3/1996 |
| WO | WO 96/11711 A1 | 4/1996 |
| WO | WO 96/30347 A1 | 10/1996 |
| WO | WO 96/33735 A1 | 10/1996 |
| WO | WO 96/33978 A1 | 10/1996 |
| WO | WO 96/33980 A1 | 10/1996 |
| WO | WO 96/34096 A1 | 10/1996 |
| WO | WO 96/40210 A1 | 12/1996 |
| WO | WO 97/38983 A1 | 10/1997 |
| WO | WO 98/24893 A2 | 6/1998 |
| WO | WO 98/36772 A1 | 8/1998 |
| WO | WO 98/43960 A1 | 10/1998 |
| WO | WO 99/06378 A1 | 2/1999 |
| WO | WO 99/06396 A1 | 2/1999 |
| WO | WO 99/09016 A1 | 2/1999 |
| WO | WO 99/042130 A1 | 8/1999 |
| WO | WO 2000/41720 A1 | 7/2000 |
| WO | WO 2000/48630 A1 | 8/2000 |
| WO | WO-2000/49412 A1 | 8/2000 |
| WO | WO 2003/015796 A1 | 2/2003 |
| WO | WO 2003/043583 A2 | 5/2003 |
| WO | WO 2003/077945 A1 | 9/2003 |
| WO | WO 2004/011476 A1 | 2/2004 |
| WO | WO 2004/032828 A2 | 4/2004 |
| WO | WO 2005/007197 A2 | 1/2005 |
| WO | WO 2006/105152 A2 | 10/2006 |
| WO | WO 2006/134423 A2 | 12/2006 |
| WO | WO 2007/026190 | 3/2007 |
| WO | WO 2007/026190 A2 | 3/2007 |
| WO | WO 2007/044515 A1 | 4/2007 |
| WO | WO 2009/035494 A2 | 3/2009 |
| WO | WO 2009/126737 A2 | 10/2009 |
| WO | WO-2011/156774 A2 | 12/2011 |
| WO | 2013/125687 A1 | 8/2013 |
| WO | WO 2014/107652 A2 | 7/2014 |
| WO | WO 2014/178195 A1 | 11/2014 |
| WO | WO 2015/143123 A2 | 9/2015 |
| WO | WO 2015/157629 A2 | 10/2015 |
| WO | WO 2015/159118 A2 | 10/2015 |
| WO | WO 2016/026742 A1 | 2/2016 |
| WO | WO 2016/044326 A1 | 3/2016 |
| WO | WO 2016/118961 A1 | 7/2016 |
| WO | WO 2016/123593 A1 | 8/2016 |
| WO | WO 2017/041027 A1 | 3/2017 |
| WO | WO 2017/062792 A1 | 4/2017 |
| WO | WO 2017/172990 A1 | 10/2017 |
| WO | 2018/002640 A2 | 1/2018 |
| WO | WO 2018/022933 A1 | 2/2018 |

(56) References Cited

FOREIGN PATENT DOCUMENTS

WO    WO 2018/023121 A1    2/2018
WO    WO 2018/094414 A1    5/2018

OTHER PUBLICATIONS

Bird, R.E., et al., "Single-chain antigen-binding proteins" Science Oct. 21, 1988; 242(4877):423-426.
Hogrefe, H.H. et al., "A bacteriophage lambda vector for the cloning and expression of immunoglobulin Fab fragments on the surface of filamentous phage" Gene, 1993, 128(1): 119-126.
Matsuda, F. et al., "Structure and physical map of 64 variable segments in the 3' 0.8—megabase region of the human immunoglobulin heavy-chain locus." Nature Genet., 1993, 3: 88-94.
Nicolaou, K.C. et al., "Calicheamicin ΘI1: A rationally designed molecule with extremely potent and selective DNA cleaving properties and apoptosis inducing activity." Angew. Chem. Intl. Ed. Engl., Feb. 1, 1994, 33(2):183-186.
Presta, L.G. et al., "Humanization of an Anti-Vascular Endothelial Growth Factor Monoclonal Antibody for the Therapy of Solid Tumors and Other Disorders" Cancer Res. 1997, 57(20):4593-4599.
Sjölander, A. et al., "ISCOMs: an adjuvant with multiple functions," J. Leukocyte Biol. 1998, 64(6):713-723.
Tomlinson, I.M. et al., "The repertoire of human germline $V_h$ sequences reveals about fifty groups of $V_h$ segments with different hypervariable loops" J. Mol. Biol., Oct. 5, 1992, 227(3): 776-798.
Williams, S.C. and Winter, G. "Cloning and sequencing of human immunoglobulin $V_\lambda$ gene segments " Eur. J. Immunol., 1993, 23: 1456-1461.
Abrahmsén et al, "Analysis of signals for secretion in the staphylococcal protein A gene," EMBO J., Dec. 30, 1985, 4(13B):3901-3906.
Arié et al., "Chaperone function of FkpA, a heat shock prolyl isomerase, in the periplasm of Escherichia coli," Mol. Microbiol., Jan. 2001, 39(1):199-210.
Bachmann, Cellular and Molecular Biology, vol. 2, Chapter 72: Derivations and Genotypes of Some Mutant Derivatives of Escherichia coli K-12, Neidhardt et al., eds.,. 1987, pp. 1190-1219, American Society for Microbiology, Washington, D.C.
Baldwin et al., "Monoclonal antibodies in cancer treatment," Lancet, Mar. 15, 1986, 327(8481):603-605.
Barbas et al., "Assembly of combinatorial antibody libraries on phage surfaces: the gene III site," Proc. Natl. Acad. Sci. U.S.A., Sep. 15, 1991, 88(18):7978-7982.
Barbas et al., "In vitro evolution of a neutralizing human antibody to human immunodeficiency virus type 1 to enhance affinity and broaden strain cross-reactivity," Proc. Nat. Acad. Sci. U.S.A., Apr. 26, 1994, 91(9):3809-3813.
Barnes et al., "Methods for growth of cultured cells in serum-free medium," Anal. Biochem., Mar. 1, 1980, 102(2):255-270.
Bass et al., "Hormone phage: an enrichment method for variant proteins with altered binding properties," Proteins, 1990, 8(4):309-314.
Bobo et al., "Convection-enhanced delivery of macromolecules in the brain," Proc. Natl. Acad. Sci. U.S.A., Mar. 15, 1994, 91(6) 2076-2080.
Boerner et al., "Production of antigen-specific human monoclonal antibodies from in vitro-primed human splenocytes," J. Immunol., Jul. 1, 1991, 147(1):86-95.
Bothmann et al., "The periplasmic Escherichia coli peptidylprolyl cis,trans-isomerase FkpA. I. Increased functional expression of antibody fragments with and without cis-prolines," J. Biol. Chem., Jun. 2, 2000, 275(22):17100-17105.
Bowie, Ju et al., Deciphering the Message in Protein Sequences: Tolerance to Amino Acid Substitutions, Science, 247: 1306-1310 (1990).
Brennan et al., "Preparation of bispecific antibodies by chemical recombination of monoclonal immunoglobulin Gi fragments," Science, Jul. 5, 1985, 229(4708):81-83.

Brodeur et al., Monoclonal Antibody Production Techniques and Applications, Chapter 4: Mouse-Human Myeloma Partners for the Production of Heterohybridomas, Schook, ed., 1987, pp. 51-63, Marcel Dekker, Inc., New York.
Brüggemann et al., "Designer mice: the production of human antibody repertoires in transgenic animals," Year in Immunol., 1993, 7:33-40.
Carter et al., "High level Escherichia coli expression and production of a bivalent humanized antibody fragment," Nature Biotechnology, Feb. 1992, 10(2):163-167.
Carter et al., "Humanization of an anti-p185$^{HER2}$ antibody for human cancer therapy," Proc. Natl. Acad. Sci. U.S.A., May 15, 1992, 89(10):4285-4289.
Chang et al., "Expression of Globo H and SSEA3 in breast cancer stem cells and the involvement of fucosyl transferases 1 and 2 in Globo H synthesis," Proc. Natl. Acad. Sci. U.S.A., Aug. 19, 2008, 105(33):11667-11672.
Chen et al., "Chaperone activity of DsbC," J. Bio. Chem., Jul. 9. 1999, 274(28):19601-19605.
Chen et al., "Selection and analysis of an optimized anti-Vegf antibody: crystal structure of an affinity-matured Fab in complex with antigen," J. Mol. Biol., Nov. 5, 1999, 293(4):865-881.
Chen et al., "Selective killing of transformed cells by cyclin/cyclin-dependent kinase 2 antagonists," Proc. Natl. Acad. Sci. U.S.A., Apr. 13, 1999, 96(8):4325-4329.
Chothia et al., "Canonical structures for the hypervariable regions of immunoglobulins," J. Mol. Biol., Aug. 20, 1987, 196(4):901-917.
Clackson et al., "Making antibody fragments using phage display libraries," Nature, Aug. 15, 1991, 352(6336):624-628.
Cunningham et al., "High-resolution epitope mapping of hGH-receptor interactions by alanine-scanning mutagenesis," Science, Jun. 2, 1989, 244(4908):1081-1085.
Embleton et al., "In-cell PCR from mRNA: amplifying and linking the rearranged immunoglobulin heavy and light chain V-genes within single cells," Nucl. Acids Res., Aug. 11, 1992, 20(15):3831-3837.
Engels et al., "Gene synthesis [new synthetic methods (77)]," Angew. Chem. Int. Ed. Engl., Jun. 1989, 28(6):716-734.
Fellouse et al., "Synthetic antibodies from a four-amino-acid code: a dominant role for tyrosine in antigen recognition," Proc. Natl. Acad. Sci. U.S.A., Aug. 24, 2004, 101(34):12467-12472.
Fishwild et al., "High-avidity human IgGK monoclonal antibodies from a novel strain of minilocus transgenic mice," Nature Biotechnol., Jul. 1996, 14(7):845-851.
Galfré et al., "Preparation of monoclonal antibodies: strategies and procedures," Methods Enzymol., 1981, 73(Pt B):3-46.
Gill et al., "Direct brain infusion of glial cell line-derived neurotrophic factor in Parkinson disease," Nature Med., May 2003, 9(5):589-595 and Addendum from Apr. 2006, 12(4):479.
Goding, Monoclonal Antibodies: Principles and Practice $2^{nd}$ ed., Chapter 3: Production of Monoclonal Antibodies, 1986, pp. 59-103, Academic Press, London.
Gonnet, GH et al., Exhaustive Matching of the Entire Protein Sequence Database, Science 256: 1443-45 (1992).
Graham et al., "Characteristics of a human cell line transformed by DNA from human adenovirus type 5," J. Gen. Virol., Jul. 1977, 36(1):59-72.
Gram et al., "In vitro selection and affinity maturation of antibodies from a naive combinatorial immunoglobulin library," Proc. Nati. Acad. Sci. U.S.A., Apr. 15, 1992, 89(8):3576-3580.
Griffiths et al., "Human anti-self antibodies with high specificity from phage display libraries," EMBO J., Feb. 1993, 12(2):725-734.
Gruber et al., "Efficient tumor cell lysis mediated by a bispecific single chain antibody expressed in Escherichia coli," J. Immunol., Jun. 1, 1994, 152(11):5368-5374.
Guss et al., "Structure of the IgG-binding regions of streptococcal protein G," EMBO J., Jul. 1986, 5(7):1567-1575.
Ham, Richard et al., Media and Growth Requirements, Meth. Enz 58, 44 (1979).
Hammerling et al., in: Monoclonal Antibodies and T-Cell Hybridomas 563-681, 1981.

(56) References Cited

OTHER PUBLICATIONS

Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hawkins et al., "Selection of phage antibodies by binding affinity. Mimicking affinity maturation," *J. Mol. Biol.*, 1992, 226(3):889-896.
Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Holliger et al., "'Diabodies': small bivalent and bispecific antibody fragments," *Proc. Natl. Acad. Sci. U.S.A.*, Jul. 15, 1993, 90(14):6444-6448.
Hoogenboom et al., "By-passing immunisation: Human antibodies from synthetic repertoires of germline $V_h$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Hurle et al., "Protein engineering techniques for antibody humanization," *Curr. Opin. Biotechnol.*, Aug. 1994, 5(4):428-433.
Huston, James et al, Protein Engineering of Antibody Binding Sites: Recovery of Specific Activity in an Anti-Digoxin Single-Chain FV Analogue Produced in *Escherichia coli*, Proc. Natl. Acad. Sci. USA, 1988, 85:5879-5883.
International Search Report dated Jul. 7, 2017, from corresponding International Patent Application No. PCT/US2017/024853, 21 pages.
Jackson et al., "In vitro antibody maturation: Improvement of a high affinity, neutralizing antibody against IL-1β," *J. Immunol.*, Apr. 1, 1995, 154(7):3310-3319.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Köhler et al., "Continuous cultures of fused cells secreting antibody of predefined specificity," *Nature*, Aug. 7, 1975, 256(5517):495-497.
Kontermann, "Intrabodies as therapeutic agents," *Methods*, Oct. 2004, 34(2):163-170.
Kostelny et al., "Formation of a bispecific antibody by the use of leucine zippers," *J. Immunol.*, Mar. 1, 1992, 148(5):1547-1553.
Kozbor, "A human hybrid myeloma for production of human monoclonal antibodies," *J. Immunol.*, Dec. 1984, 133(6):3001-3005.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lehninger, *Biochemistry: The Molecular Basis of Cell Structure and Function*, $2^{nd}$ ed., 1975, pp. 73-75, Worth Publishers, New York.
Leung et al., "A method for random mutagenesis of a defined DNA segment using a modified polymerase chain reaction," *Technique—A Journal of Methods in Cell and Molecular Biology*, Aug. 1989, 1(1):11-15.
Lindmark et al., "Binding of immunoglobulins to protein A and immunoglobulin levels in mammalian sera," *J. Immunol. Meth.*, Aug. 12, 1983, 62(1):1-13.
Liu et al., "Eradication of large colon tumor xenografts by targeted delivery of maytansinoids," *Proc. Natl., Acad. Sci. U.S.A.*, Aug. 6, 1996, 93(16):8618-8623.
Lode et al., "Targeted therapy with a novel enediyene antibiotic calicheamicin $\Theta^I_1$ effectively suppresses growth and dissemination of liver metastases in a syngeneic model of murine neuroblastoma," *Cancer Res.*, Jul. 15, 1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Lou, et al., Stage-specific embryonic antigent-4 as a potential therapeutic target in glioblastoma multiforms and other cancers. Proc Natl Acad Sci USA 2014, 111(7):2482-7.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.
Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.
Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.
Marasco, "Intrabodies: turning the humoral immune system outside in for intracellular immunization," *Gene Therapy*, Jan. 1997, 4(1):11-15.
Marks et al., "By-passing immunization. Human antibodies from V-gene libraries displayed on phage," *J. Mol. Biol.*, Dec. 5, 1991, 222(3):581-597.
Marks et al., "By-passing immunization: Building high affinity human antibodies by chain shuffling," *Nature Biotechnology*, Jul. 1992, 10(7):779-783.
Mather et al., "Culture of testicular cells in hormone-supplemented serum-free medium," *Annals N.Y. Acad. Sci.*, 1982, 383:44-68.
Mather, "Establishment and characterization of two distinct mouse testicular epithelial cell lines," *Biol. Reprod.*, Aug. 1980, 23(1):243-252.
McCafferty et al., "Phage antibodies: Filamentous phage displaying antibody variable domains," *Nature*, Dec. 6, 1990, 348:552-554.
Milstein, C & Cuello, AC, Hybrid Hydridomas and their use in immunohistochemistry, Nature 305, 537-540, Oct. 1993.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Munson et al., "Ligand: A versatile computerized approach for characterization of ligand-binding systems," *Anal. Biochem.*, Sep. 1, 1980, 107(1):220-239.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.

(56) References Cited

OTHER PUBLICATIONS

Niculescu-Duvaz et al., "Antibody-directed enzyme prodrug therapy (ADEPT): A review," *Adv. Drg. Del. Rev.*, Jul. 7, 1997, 26(2-3):151-172.
Nikula, Kristen et al., Animal Models of Chronic Bronchitis and Their Relevance to Studies of Particle-Induced Disease, Inhal. Toxicol. 4(12): 123-53, 2000.
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Papanastassiou et al., "The potential for efficacy of the modified (ICP 34.5) herpes simplex virus HSV1716 following intratumoural injection into human malignant glioma: a proof of principle study," *Gene Therapy*, Mar. 2002, 9(6):398-406.
Pearson, William, Using the FASTA Program to Search Protein and DNA Sequence Databases, Methods Mol. Biol. 243:307-31, 1994.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology*, vol. 113: The Pharacology of Monoclonal Antibodies, Chapter 11: Antibodies from *Escherichia coli*, Rosenberg et. al., eds., 1994, pp. 269-315, Springer-Verlag, Berlin.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Struct. Biol.*, Aug. 1992, 2(4):593-596.
Proba et al., "Functional antibody single-chain fragments from the cytoplasm of *Escherichia coli*: influence of thioredoxin reductase (TrxB)," *Gene*, Jul. 4, 1995, 159(2):203-207.
Queen, Cary et al, A Humanized Antibody that Binds to the Interleukin 2 Receptor, Proc Natl Acad Sci., 86: 10029-10033 (1989).
Ramm et al., "The periplasmic *Escherichia coli* peptidylprolyl cis, trans-isomerase FkpA. II. Isomerase-independent chaperone activity in vitro," *J. Biol. Chem.*, Jun. 2, 2000, 275(22):17106-17113.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Rowland et al, "Drug localisation and growth inhibition studies of vindesine-monoclonal anti-CEA conjugates in a human tumour xenograft," *Cancer Immunol. Immunother.*, 1986, 21(3):183-187.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schier et al., "Identification of functional and structural amino-acid residues by parsimonious mutagenesis," *Gene*, Mar. 9, 1996, 169(2):147-155.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.

Sims et al., "A humanized CD18 antibody can block function without cell destruction," *J. Immunol.*, Aug. 15, 1993, 151(4):2296-2308.
Sjolander, Dirk et al., Cationic Cage-Like Complexes Formed by DC-Cholesterol, Quil-A, and Phospholipid, J. Leukocyte Biol. 64:713, 1998.
Skerra, "Bacterial expression of immunoglobulin fragments," *Curr. Opinion in Immunol.*, Apr. 1993, 5(2):256-262.
Sonderstrup, Grete, Development of Humanized Mice as a Model of Inflammatory Arthritis, Springer Sem. Immunopathol. 25: 35-45, 2003.
Suresh et al., "Bispecific monoclonal antibodies from hybrid hybridomas," *Methods in Enzymology*, 1986, 121:210-228.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Traunecker et al., "Bispecific single chain molecules (Janusins) target cytotoxic lymphocytes on HIV infected cells," *EMBO J.*, Dec. 1991, 10(12):3655-3659.
Tutt et al., "Trispecific F(ab')$_3$ derivatives that use cooperative signaling via the TCR/CD3 complex and CD2 to activate and redirect resting cytotoxic T cells," *J. Immunol.*, Jul. 1, 1991, 147(1):60-69.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Vaswani et al., "Humanized antibodies as potential therapeutic drugs," *Ann. Allergy, Asthma Immunol.*, Aug. 1998, 81(2):105-116, 119.
Verhoeyen et al., "Reshaping human antibodies: grafting an antilysozyme activity," *Science*, Mar. 25, 1988, 239(4847):1534-1536.
Ward et al., "Binding activities of a repertoire of single immunoglobulin variable domains secreted from *Escherichia coli*," *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Winter et al., "Making antibodies by phage display technology," *Annu. Rev. Immunol.*, 1994, 12:433-455.
Yaniv, Moshe, Enhancing Elements for Activation of Eukaryotic Promoters, Nature 297: 17-18, 1982.
Yansura et al., "Nucleotide sequence selection for increased expression of heterologous genes in *Escherichia coli*," *Methods: A Companion to Methods in Enzymol.*, Aug. 1992, 4(2):151-158.
Yelton et al., "Affinity maturation of the BR96 anti-carcinoma antibody by codon-based mutagenesis." *J. Immunol.*, Aug. 15, 1995, 155(4):1994-2004.
Barbas, C.F. et al., "Assembly of combinatorial antibody libraries on phage surfaces: the gene III site," *Proc. Natl. Acad. Sci. U.S.A.*, Sep. 15, 1991, 88(18):7978-7982.
Bowie, JU et al., Deciphering the Message in Protein Sequences: Tolerance to Amino Acid Substitutions, Science, 1990, 247: 1306-1310.
Brennan et al., "Preparation of bispecific antibodies by chemical recombination of monoclonal immunoglobulin Gl fragments," *Science*, Jul. 5, 1985, 229(4708):81-83.
Clackson, T. et al., "Making antibody fragments using phage display libraries," *Nature*, Aug. 15, 1991, 352(6336):624-628.
Fishwild et al., "High-avidity human IgGκ monoclonal antibodies from a novel strain of minilocus transgenic mice," *Nature Biotechnol.*, Jul. 1996, 14(7):845-851.
Goding, J.W. *Monoclonal Antibodies: Principles and Practice* 2$^{nd}$ ed., Chapter 3: Production of Monoclonal Antibodies, 1986, pp. 59-103, Academic Press, London.
Gonnet, G.H. et al., Exhaustive Matching of the Entire Protein Sequence Database, Science, 1992, 256: 1443-1445.

(56) References Cited

OTHER PUBLICATIONS

Gram et al., "In vitro selection and affinity maturation of antibodies from a naive combinatorial immunoglobulin library," Proc. Natl. Acad. Sci. U.S.A., Apr. 15, 1992, 89(8):3576-3580.

Ham, Richard et al., Media and Growth Requirements, Meth. Enz 1979, 58, 44-93.

Hammerling et al., in: Monoclonal Antibodies and T-Cell Hybridomas, 1981, 563-681, sole distributors for the USA and Canada, Elsevier North-Holland.

Holliger et al., "'Diabodies': small bivalent and bispecific antibody fragments," Proc. Natl. Acad. Sci. U.S.A., Jul. 15, 1993, 90(14):6444-6448.

International Search Report dated Jul. 7, 2017, from corresponding International Patent Application No. PCT/US2017/024853, by Yu, Cheng-Der Tony et al., "Antibodies, Pharmaceutical Compositions and Methods" filed Mar. 29, 2017, 21 pages.

Jones, A. J. S. et al., "Rapid PCR-cloning of full-length mouse immunoglobulin variable regions," Nature Biotechnol., Jan. 1991, 9(1):88-89.

Jones, A. J. S. et al., "Replacing the complementarity-determining regions in a human antibody with those from a mouse," Nature, May 29-Jun. 4, 1986, 321(6069):522-525.

Jones, A. J. S. "Analysis of polypeptides and proteins," Adv. Drug Delivery Rev., JanuaryApril 1993, 10(1):29-90.

Kam et al., "Carbon nanotubes as multifunctional biological transporters and near-infrared agents for selective cancer cell destruction," Proc. Natl. Acad. Sci. U.S.A., Aug. 16, 2005, 102(33):11600-11605.

Köhler, G. et al., "Continuous cultures of fused cells secreting antibody of predefined specificity," Nature, Aug. 7, 1975, 256(5517):495-497.

Kontermann, R.E. "Intrabodies as therapeutic agents," Methods, Oct. 2004, 34(2):163-170.

Lindmark, R. et al., "Binding of immunoglobulins to protein A and immunoglobulin levels in mammalian sera," J. Immunol. Meth., Aug. 12, 1983, 62(1):1-13.

Lode, H.N. et al., "Targeted therapy with a novel enediyene antibiotic calicheamicin $\Theta^I_1$ effectively suppresses growth and dissemination of liver metastases in a syngeneic model of murine neuroblastoma," Cancer Res., Jul. 15, 1998, 58(14):2925-2928.

Lou, Y. et al., Stage-specific embryonic antigent-4 as a potential therapeutic target in glioblastoma multiforms and other cancers. Proc Natl Acad Sci USA 2014, 111(7):2482-7.

Mandler, R. et al., "Immunoconjugates of geldanamycin and anti-HER2 monoclonal antibodies: antiproliferative activity on human breast carcinoma cell lines," J. Nat. Cancer Inst., Oct. 4, 2000, 92(19):1573-1581.

Milstein, C & Cuello, AC, Hybrid Hydridomas and their use in immunohistochemistry, Nature 305, 537-540, Oct. 1983.

Nikula, Kristen et al., Animal Models of Chronic Bronchitis and Their Relevance to Studies of Particle-Induced Disease, Inhal. Toxicol., 2000, 4(12): 123-153.

Pearson, William, Using the FASTA Program to Search Protein and DNA Sequence Databases, Methods Mol. Biol. 243:307-331, 1994.

Plückthun, Handbook of Experimental Pharmacology, vol. 113: The Pharmacology of Monoclonal Antibodies, Chapter 11: Antibodies from Escherichia coli, Rosenberg et al., eds., 1994, pp. 269-315, Springer-Verlag, Berlin.

Queen, Cary et al, A Humanized Antibody that Binds to the Interleukin 2 Receptor, Proc Natl Acad Sci., 1989, 86: 10029-10033.

Shalaby et al., "Development of humanized bispecific antibodies reactive with cytoxic lymphocytes and tumor cells overexpressing the HER2 protooncogene," J. Exp. Med., Jan. 1, 1992, 175(1):217-225.

Sønderstrup, Grete, Development of Humanized Mice as a Model of Inflammatory Arthritis, Springer Sem. Immunopathol., 2003, 25(1): 35-45.

Thorpe, P.E. (1985) "Antibody Carriers of Cytotoxic Agents in Cancer Therapy: A Review," in Monoclonal Antibodies '84: Biological and Clinical Applications, A. Pinchera et al. (ed.s), pp. 475-506.

Allen, P. Z. et al., Immunochemical Studies on a Sophorosyl-Azoprotein Conjugate, Biochemistry, 1967, 6(10), 3029-3036.

Arigi, Emma, et al. "Design of a covalently bonded glycosphingolipid microarray." Glycoconjugate Journal 29.1 (2012): 1-12.

Avery, Oswald et al., Chemo-Immunological Studies on Conjugated Carbohydrate-Proteins, J. Exp. Med., 1929, 50, 533-550.

Berenbaum, M. C., What is Synergy?, Pharmacol. Rev. 41(2):93-141, 1989.

Bergman, Jan, and Lennart Venemalm. "Efficient synthesis of 2-chloro-, 2-bromo-, and 2-iodoindole." The Journal of Organic Chemistry 57.8 (1992): 2495-2497.

Bertozzi, CR et al., Glycans in Cancer and Inflammation-Potential for Therapeutics and Diagnostics, Nat Rev Drug Discovery, 2005, 4, 477-488.

Bhaskar, Vinay, et al. "E-selectin up-regulation allows for targeted drug delivery in prostate cancer." Cancer Research 63.19 (2003): 6387-6394.

Bliss, C.I., The Calculation of Microbial Assays, Bacterial. Rev. 20:243-258, 1956.

Borisy, Alexis et al., Systematic Discovery of Multicomponent Therapeutics, Proc. Natl. Acad. Sci. 100(13):7977-7982, 2003.

Bosse, Folkert et al., Linear Synthesis of the Tumor-Associated Carbohydrate Antigens Globo-H, SSEA-3, and Gb3, J Org Chem. 67(19):6659-70, 2002.

Bremer, E. G., et al. "Characterization of a glycosphingolipid antigen defined by the monoclonal antibody MBr1 expressed in normal and neoplastic epithelial cells of human mammary gland." Journal of Biological Chemistry 259.23 (1984): 14773-14777.

Chang et al., "Potent immune-modulating and anticancer effects of NKT cell stimulatory glycolipids," Proc. Natl. Acad. Sci. USA, Jun. 19, 2007, 104(25):10299-10304.

Chen, Wei, et al. "Determination of thiols and disulfides via HPLC quantification of 5-thio-2-nitrobenzoic acid." Journal of Pharmaceutical and Biomedical Analysis 48.5 (2008): 1375-1380.

Cheung, Sarah et al., Stage-Specific Embryonic Antigen-3 (SSEA-3) and β3GalT5 are cancer specific and Significant Markers for Breast Cancer Stem Cells, PNAS, Jan. 26, 2016, vol. 113, No. 4, pp. 960-965.

Chou, Ting-Chao and Talalay, Paul, A Simple Generalized Equation for the Analysis of Multiple Inhibitions of Michaelis-Menten Kinetic Systems, J. Biol. Chem. 252:6438-6442, 1977.

Chou, T. C. And Talalay, P., Quantitative Analysis of Dose-Effect Relationships: The Combined Effects of Multiple Drugs or Enzyme Inhibitors. Adv. Enzyme Regul. 22:27-55, 1984.

Chuang, Po-Kai, et al. "Signaling pathway of globo-series glycosphingolipids and β1, 3-galactosyltransferase V (β3GalT5) in breast cancer." Proceedings of the National Academy of Sciences 116.9 (2019): 3518-3523.

ClinicalTrials.gov [Internet]. Bethesda (MD): National Library of Medicine (US). Jan. 24, 2012—. Trial of Active Imunotherapy with Globo H-KLH (OPT-822) in Metastatic Breast Cancer Subjects); Jan. 24, 2012 [cited Oct. 11, 2017]; [about 7 screens]. Available from: https:clinicaltrials.gov/ct2/show/NCT01516307.

Clynes, Raphael, et al. "Fc receptors are required in passive and active immunity to melanoma." Proceedings of the National Academy of Sciences 95.2 (1998): 652-656.

Cuzick, J., et al. "Overview of the main outcomes in breast-cancer prevention trials." The Lancet 361.9354 (2003): 296-300.

Danishefsky, Samuel J., et al. "Development of Globo-H cancer vaccine." Accounts of Chemical Research 48.3 (2015): 643-652.

Doronina, Svetlana O., et al. "Development of potent monoclonal antibody auristatin conjugates for cancer therapy." Nature Biotechnology 21.7 (2003): 778-784.

Eller, Chelcie et al., Human Cancer Antigen Globo H Is a Cell-Surface Ligand for Human Ribonuclease 1, ACS Central Science. vol. 1, p. 181-90, Jul. 13, 2015.

Evans, T. R. J., and S. B. Kaye. "Vaccine therapy for cancer—fact or fiction?" Q J Med 92.6 (1999): 299-307.

(56) References Cited

OTHER PUBLICATIONS

Extended European Search Report, Application No. 15842660.1, dated Mar. 12, 2018, 9 pages.
Extended European Search Report from corresponding European App. No. 16843131.0, dated Feb. 14, 2019, 13 Pages.
Feng, Li. "Probing lipid—protein interactions using lipid microarrays." Prostaglandins & other lipid mediators 77.1-4 (2005): 158-167.
Fielder, R. J. et al., An Immunogenic Polysaccharide-Protein Conjugate, J. Immunol., 1970, 105(1), 265-267.
Fitzgerald, Jonathan et al., Systems Biology and Combination Therapy in the Quest for Clinical Efficacy, Nature Chem. Biol. 2(9):458-466, 2006.
Francisco, Joseph A., et al. "cAC10-vcMMAE, an anti-CD30—monomethyl auristatin E conjugate with potent and selective antitumor activity." Blood 102.4 (2003): 1458-1465.
Gazzano-Santoro, Hélène, et al. "A non-radioactive complement-dependent cytotoxicity assay for anti-CD20 monoclonal antibody." Journal of Immunological Methods 202.2 (1997): 163-171.
Gijsen, H.J. et al., Recent Advances in the Chemoenzymatic Synthesis of Carbohydrates and Carbohydrate Mimetics, Chem. Rev., 96, 443-473, 1996.
Gilewski, Teresa et al Immunization of Metastatic Breast Cancer Patients with a Fully Synthetic Globo H Conjugate: A Phase I Trial, Proc Natl Acad Sci USA 98:3270-3275, 2001.
Goebel, Walther et al., Chemo-immunological Studies on Conjugated Carbohydrate-Proteins, J. Exp. Med., 1929, 50, 521-531.
Grant, Oliver C., et al. "Presentation, presentation, presentation! Molecular-level insight into linker effects on glycan array screening data." Glycobiology 24.1 (2014): 17-25.
Greco, William et al., The Search for Synergy: A Critical Review From a Response Surface Perspective, Pharmacol. Rev. 47(2) :331-385, 1995.
Hakomori et al., "Glycosphingolipid antigens and cancer therapy," Chem. & Biol., Feb. 1997, 4(2):97-104.
Hakomori, Sen-Itiroh, Tumor-associated carbohydrate antigens defining tumor malignancy: Basis for development of and-cancer vaccines, 2001, Advances in Experimental Medicine and Biology. 491 :369-402.
Harris, J. Robin, et al. "Keyhole limpet hemocyanin (KLH), II: Characteristic reassociation properties of purified KLH1 and KLH2." Micron 28.1 (1997): 43-56.
Harris, J. R., and J. Mark 1. "Keyhole limpet hemocyanin (KLH): a biomedical review." Micron 30.6 (1999): 597-623.
Heffernan, Michael J., et al. "In vivo efficacy of a chitosan/IL-12 adjuvant system for protein-based vaccines." Biomaterials 32.3 (2011): 926-932.
Hernández-Ledesma, Blanca, Chia-Chien Hsieh, and O. Ben. "Lunasin, a novel seed peptide for cancer prevention." Peptides 30.2 (2009): 426-430.
Himmelspach, K. et al., Use of 1-(m-aminophenyl)flavazoles for the Preparation of Immunogens with Oligosaccharide Determinant Groups, Eur. J. Immunol., 1971, 1(2), 106-112.
Hirabayashi, J. et al., Oligosaccharide Microarrays for Glycomics, Trends in Biotechnology 21 (4): 141-143, 2003.
Hirano, Fumiya, et al. "Blockade of B7-H1 and PD-1 by monoclonal antibodies potentiates cancer therapeutic immunity." Cancer Research 65.3 (2005): 1089-1096.
Huang, Cheng-Yuan et al., Carbohydrate Microarray for Profiling the Antibodies Interacting with Globo H Tumor Antigen, Proc Natl Acad Sci, 103:15-20, 2006.
Huang, Yen-Lin, and Chung-Yi Wu. "Carbohydrate-based vaccines: challenges and opportunities." Expert Review of Vaccines 9.11 (2010): 1257-1274.
Huang, Yen-Lin, et al. "Carbohydrate-based vaccines with a glycolipid adjuvant for breast cancer." Proceedings of the National Academy of Sciences 110.7 (2013): 2517-2522.
International Search Report dated Jan. 8, 2016 in counterpart application PCT/IB2014/002744, 3 pages.
International Search Report and Written Opinion of the International Searching Authority, from corresponding International Patent Application No. PCT/US2015/050270, dated Dec. 15, 2015, 14 Pages.
International Search Report and Written Opinion of the International Searching Authority, from corresponding International Patent Application No. PCT/US16/50252, dated Nov. 17, 2016, 12 Pages.
International Search Report/Written Opinion dated Oct. 31, 2017 in counterpart PCT Application No. PCT/US2017/044244, 13 pages.
International Search Report dated Nov. 28, 2017 in counterpart application PCT/US2017/044713, 6 pages.
International Search Report/Written Opinion dated Mar. 12, 2018 in counterpart PCT Application No. PCT/US17/062886, 22 pages.
International Search Report/Written Opinion dated Oct. 18, 2019 in counterpart application PCT/US2019/035168, 13 pages.
Jeon, Insik et al., A Practical Total Synthesis of Globo-H for Use in Anticancer Vaccines, J. Org. Chem., 2009, 74(21), pp. 8452-8455.
Kannagi, Reiji, et al. "Stage-specific embryonic antigens (SSEA-3 and-4) are epitopes of a unique globo-series ganglioside isolated from human teratocarcinoma cells." EMBO Journal 2.12 (1983): 2355-2361.
Kannagi et al., "New globoseries glycosphingolipids in human teratocarcinoma reactive with the monoclonal antibody directed to a developmentally regulated antigen, stage-specific embryonic antigen 3," J. Biol. Chem., Jul. 25, 1983, 258(14):8934-8942.
Klussman, Kerry, et al. "Secondary mAb-vcMMAE conjugates are highly sensitive reporters of antibody internalization via the lysosome pathway." Bioconjugate chemistry 15.4 (2004): 765-773.
Koeller, Kathryn et al., Enzymes for Chemical Synthesis, Nature, 409, 232-240, 2001.
Komenaka, Ian, Heidi Hoerig, and Howard L. Kaufman "Immunotherapy for melanoma." Clinics in Dermatology 22.3 (2004): 251-265.
Konecny, G. et al., Drug Interactions and Cytotoxic Effects of Paclitaxel in Combination with Carboplatin, Epirubicin, Gemcitabine or Vinorelbine in Breast Cancer Cell Lines and Tumor Samples, Breast Cancer Res. and Treatment 67:223-233, 2001.
Krainer, Florian et al., An Updated View on Horseradish Peroxidases: Recombinant Production and Biotechnological Applications, Applied Microbiology and Biotechnology, vol. 99, pg. 1611-1625, Jan. 11, 2015.
Kufer, Peter, et al. "A revival of bispecific antibodies." Trends in biotechnology 22.5 (2004): 238-244.
Lee et al. "Immunogenicity study of Globo H analogues with modification at the reducing or nonreducing end of the tumor antigen" Journal of the American Chemical Society, (2014) 136(48), 16844-16853.
Liang, Pi-Hui, et al. "Quantitative Microarray Analysis of Intact Glycolipid—CD1d Interaction and Correlation with Cell-Based Cytokine Production." Journal of the American Chemical Society 130.37 (2008): 12348-12354.
Liu, Gui, et al. "QS-21 structure/function studies: effect of acylation on adjuvant activity." Vaccine 20.21-22 (2002): 2808-2815.
Livingston, Philip, "Augmenting the immunogenicity of carbohydrate tunor antigens" Seminars in Cancer Biology, Cancer Biol, 6(6):357-366, 1995.
Lloyd, Kenneth, "Tumor Antigens Known to be Immunogenic in Man" in Specific Immunotherapy of Cancer with Vaccines, 1993, 690, 50-58.
Lucas, A.H. et al., Carbohydrate Moieties as Vaccine Candidates: Meeting Summary, Vaccine, vol. 28(4), Jan. 2010, pp. 1121-1131.
Mao, Shenlan, et al. "Phage-display library selection of high-affinity human single-chain antibodies to tumor-associated carbohydrate antigens sialyl Lewisx and Lewisx." Proceedings of the National Academy of Sciences 96.12 (1999): 6953-6958.
Mao, Weiguang, et al. "EphB2 as a therapeutic antibody drug target for the treatment of colorectal cancer." Cancer Research 64.3 (2004): 781-788.
Martineau, R.S. et al., Immunochemical Studies on a Panosyl-Azoprotein conjugate, Immunochemistry, vol. 8, 705-718, 1971.
Menard S et al., Generation of Monoclonal Antibodies Reacting with Normal and Cancer Cells of Human Breast, Cancer Res 43: 1295-1300, 1983.

(56) References Cited

OTHER PUBLICATIONS

Miller, Kathy, et al. "Design, construction, and in vitro analyses of multivalent antibodies." The Journal of Immunology 170.9 (2003): 4854-4861.
Office Action issued in corresponding Taiwan patent application No. 103131876, dated Dec. 26, 2016, 7 pages.
Oxenius, Annette, et al. "CpG-containing oligonucleotides are efficient adjuvants for induction of protective antiviral immune responses with T-cell peptide vaccines." Journal of Virology 73.5 (1999): 4120-4126.
Pegram, Mark et al., Inhibitory Effects of Combinations of HER-2/neu Antibody and Chemotherapeutic Agents Used for Treatment of Human Breast Cancers, Oncogene 18:2241-2251, 1999.
Pegram, Mark et al., Rational Combinations of Trastuzumab With Chemotherapeutic Drugs Used in the Treatment of Breast Cancer, J. of the Nat. Cancer Inst. 96(10):739-749, 2004.
Presta, Leonard G. "Antibody engineering." Current Opinion in Biotechnology 3.4 (1992): 394-398.
Ragupathi, Govindaswami et al., Immunization of Mice with a Fully Synthetic Globo H Antigen Results in Antibodies against Human Cancer Cells: A Combined Chemical—Immunological Approach to the Fashioning of an Anticancer Vaccine, Angew Chem Int, 36(1-2), 125-128, Feb. 1997.
Ragupathi, Govindaswami, et al. "Constructing an adenocarcinoma vaccine: Immunization of mice with synthetic KH-1 nonasaccharide stimulates anti-KH-1 and anti-Le$^y$ antibodies." International Journal of Cancer 99.2 (2002): 207-212.
Ravetch et al., "Fc receptors," Annu. Rev. Immunol., 1991, 9:457-492.
Rüde, Erwin et al., Synthesis of the N-carboxy-α-amino Acid Anhydrides of Several O-acetylated Serine Glycosides, Carbohydr. Research, 1968, 8(2), 219-232.
Schiffman, Mark, and Philip E. Castle. "The promise of global cervical-cancer prevention." New England Journal of Medicine 353.20 (2005): 2101-2104.
Schwarz, Mikael, et al. "A new kind of carbohydrate array, its use for profiling antiglycan antibodies, and the discovery of a novel human cellulose-binding antibody." Glycobiology 13.11 (2003): 749-754.
Search Report issued in corresponding Taiwan patent application No. 103131876, prepared Dec. 20, 2016, 1 page.
Sedlik, Christine et al., Effective Antitumor Therapy Based on a Novel Antibody-Drug Conjugate Targeting the Tn Carbohydrate Antigen, Oncoimmunology, Jul. 2016, vol. 5, No. 7, e1171434-1-13.
Sigma-Aldrich, Product Information for Hemocyanin From Megathura Crenulata, Catalog No. H7017, 1 Page, 2016.
Slovin, S.F. et al., Carbohydrate Vaccines in Cancer: Immunogenicity of a Fully Synthetic Globo H Hexasaccharide Conjugate in Man, Proc Natl Acad Sci, 96:5710-5715, May 1999.
Speed, Margaret A., Daniel IC Wang, and Jonathan King. "Multimeric intermediates in the pathway to the aggregated inclusion body state for P22 tailspike polypeptide chains." Protein Science 4.5 (1995): 900-908.
Sun, Hongfan, Kevin GJ Pollock, and James M. Brewer. "Analysis of the role of vaccine adjuvants in modulating dendritic cell activation and antigen presentation in vitro." Vaccine 21.9-10 (2003): 849-855.
Toyokuni, Tatsushi et al., Synthetic Vaccines: Synthesis of a Dimeric Tn Antigen-Lipopeptide Conjugate That Elicits Immune Responses Against Tn-Expressing Glycoproteins, J. Am. Chem. Soc., 1994, 116(1), 395-396.
Wakimoto, Hiroaki, et al. "Intensified antitumor immunity by a cancer vaccine that produces granulocyte-macrophage colony-stimulating factor plus interleukin 4." Cancer Research 56.8 (1996): 1828-1833.
Wallner, Fredrik K., et al. "Solid-phase synthesis of serine-based glycosphingolipid analogues for preparation of glycoconjugate arrays." Organic & Biomolecular Chemistry 3.2 (2005): 309-315.
Wang et al., "Glycan microarray of Globo H and related structures for quantitative analysis of breast cancer," Proc. Natl. Acad. Sci. U.S.A., Aug. 19, 2008, 105(33):11661-11666.
Wilen et al., "Strategies in optical resolutions," Tetrahedron, 1977, 33(21):2725-2736.
Wilman, "Prodrugs in Cancer Chemotherapy" Biochemical Society Transactions, 14, pp. 375-382, 615th Meeting Belfast, 1986.
Wymer, Nathan et al., Enzyme-Catalyzed Synthesis of Carbohydrates, Curr. Opin. Chem. Biol., 4, 110-119, 2000.
Zhang et al., "Selection of tumor antigens as targets for immune attack using immunohistochemistry: I. Focus on gangliosides," Int. J. Cancer, Sep. 26, 1997,73(1):42-49.
Zhou, Zhifang et al., A Fully Synthetic Self-Adjuvanting Globo H-Based Vaccine Elicited Strong T Cell-Mediated Antitumor Immunity, Chem. Sci., 2015, 6, 7112-7121.
Zhu, Jianglong et al., From Synthesis to Biologics: Preclinical Data on a Chemistry Derived Anticancer Vaccine, J. Am. Chem. Soc. 131(26):9298-9303, 2009.
Büll, Christian, et al. "Sialic acid blockade suppresses tumor growth by enhancing T-cel mediated tumor immunity," Cancer Research 78.13 (2018): 3574-3588.
Chevolot, Yann, Ed. "Carbohydrate microarrays: methods and protocols," Humana Press, 2012, 431 pages.
Extended European Search Report from corresponding European App. No. 17776596.3, dated Feb. 6, 2020, 9 pages.
Huang, Yuhui, et al. "Vascular normalizing closes of antiangiogenic treatment reprogram the immunosuppressive tumor microenvironment and enhance immunotherapy." Proceedings of the National Academy of Sciences 109.43 (2012): 17561-17566.
International Search Report dated Dec. 3, 2019 in counterpart application PCT/US2019/039414, 5 pages.
International Search Report dated Dec. 30, 2019 in counterpart application PCT/US2019/054221, 4 pages.
MacCallum, Robert M., et al. "Antibody-antigen interactions: contact analysis arid binding site topography." Journal of Molecular Biology 262.5 (1996): 732-745.
O'Cearbhaill, et al. "Polyvalent vaccine-KLH conjugate and OPT-821 with bevacizumab (BEV) in patients with ovarian cancer in second or greater remission" Journal of Clinical Oncology 31, No. 15_suppl(May 20, 2013), 5550-5550.
Ragupathi, Govindaswami, et al. "A novel and efficient method for synthetic carbohydrate conjugate vaccine preparation: synthesis of sialyl Tn-KLH conjugate using a 4-(4-N-maleimidomethyl) cyclohexane-1-carboxy hydrazide (MMCCH) linker arm," Glycoconjugate Journal 15.3 (1998): 217-221.

\* cited by examiner

Group 2: Globo H-2C2, 0.4 mg/kg x 10, IP, Twice weekly

Group 3: Commercial SSEA-4 antibody (MC-813-70), 0.4 mg/kg x 10, IP, Twice weekly Group 4: 1G1s, 0.4 mg/kg x 10, IP, Twice weekly Group 5: 1J1s, 0.4 mg/kg x 10, IP, Twice weekly

Figure 9

| Ab | Clone | MCF-7 breast cancer | MDA-MB231 breast cancer | HPAC Pancreatic cancer | LN-18 Glioblastoma | LL-2 Lewis lung carcinoma | HK-2 Kidney cortex / proximal tubule | NL-20 Bronchial Epithelium | TH-LE3 Liver | HUMEC Mammary Epithelium |
|---|---|---|---|---|---|---|---|---|---|---|
| SSEA4 | 1J1s | 93% | 84.28% | 99.59% | 2.42% | 9.82% | 89.88% | 9.31% | 6.09% | 4.53% |
| | 1G1s | 70.57% | 51.78% | 95.76% | 4.09% | 4.76% | 35.63% | 8.29% | 5.06% | 5.73% |
| | 2F20s | 16.04% | 7.60% | 55.56% | 3.11% | 5.65% | 10.48% | 13.98% | 5.36% | 4.92% |
| | commercial | 99.68% | 99.41% | 100% | 33.53% | 54.59% | 96.07% | 0.96% | 11.23% | 7.19% |

Cancer cell lines / Non-tumorigenic cell lines

ANTIBODIES, PHARMACEUTICAL COMPOSITIONS AND METHODS

CROSS-REFERENCE TO RELATED APPLICATIONS

This application claims the priority of U.S. Provisional Patent Application No. 62/314,841, filed Mar. 29, 2016. The entirety of the aforementioned application is incorporated herein by reference.

FIELD

The present disclosure relates to antibodies and binding fragments thereof to carbohydrate antigens, as well as nucleic acids encoding such as antibodies, complementary nucleic acids, polypeptides, vectors, host cells, and methods of making and using thereof, including pharmaceutical compositions comprising said antibody and/or binding fragments. Furthermore, methods are provided for administering antibodies to a subject in an amount effective to inhibit cancer cells. Specifically, antibodies that bind to stage-specific embryonic antigen 4 (SSEA-4) are disclosed herein, as well as related compositions and methods of use. Methods of use include, without limitation, cancer therapies and diagnostics.

BACKGROUND OF THE INVENTION

Numerous surface carbohydrates are expressed in malignant tumor cells. For example, Globo H has been shown to overexpress on a variety of epithelial cancers and is associated with tumor aggressiveness and poor prognosis in breast cancer and small cell lung carcinoma. Previous studies have shown that Globo H and Stage-specific embryonic antigen 3 (SSEA-3, also called Gb5) were observed on breast cancer cells and breast cancer stem cells (WW Chang et al. "Expression of Globo H and SSEA3 in breast cancer stem cells and the involvement of fucosyl transferases 1 and 2 in Globo H synthesis." PNAS, 105(33): 11667-11672, 2008). These findings support a rationale for the development of antibodies to tumor associated carbohydrate antigens, as there is still an medical unmet need for effective treatment and/or prevention for cancer. It is of great interest to identify glycan markers associated with and/or predictive of cancers, and develop antibodies against the markers for use in diagnosing and treating a broad spectrum of cancers.

SUMMARY OF THE INVENTION

The present disclosure is based on the discovery that stage-specific embryonic antigen 4 (SSEA-4) is abundantly expressed in a broad spectrum of cancers, but not on normal cells. Cancers expressing SSEA-4 include, but are not limited to, breast cancer, lung cancer, esophageal cancer, rectal cancer, biliary cancer, liver cancer, buccal cancer, gastric cancer, colon cancer, nasopharyngeal cancer, kidney cancer, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer, basal cell carcinoma, squamous cell carcinoma, melanoma, or brain tumor.

In one aspect, the present disclosure features an antibody or binding fragment thereof specific to SSEA-4. The anti-SSEA-4 antibody binds to Neu5Acα2→3Galβ1→3GalNAcβ1→3Galα1→4Galβ1→4Glcβ1.

In certain aspects, the present disclosure provides for hybridoma clones designated as 1J1s (deposited under American Type Culture Collection (ATCC) Accession Number PTA-122679), 1G1s (deposited under ATCC Accession Number PTA-122678), 2F20s (deposited under ATCC Number PTA-122676), and antibodies or antigen-binding fragments produced therefrom.

In one aspect, the present disclosure provides an antibody, or an antigen-binding fragment thereof, comprising: a heavy chain variable domain (VH) comprises of an amino acid sequence of at least about 80% sequence homology to the amino acid sequence set forth in SEQ ID NO: 3 and/or a light chain variable domain (VL) comprises of an amino acid sequence of at least about 80% homology to the amino acid sequence as set forth in SEQ ID NO: 4 (Table 1). In some aspects, the amino acid sequence of the heavy chain variable domain (VH), which comprises of an amino acid sequence of at least about 80% sequence homology to the amino acid sequence set forth in SEQ ID NO: 3, will include or exclude naturally occurring sequences. In some aspects the amino acid sequence of the light chain variable domain (VL), which comprises of an amino acid sequence of at least about 80% sequence homology to the amino acid sequence set forth in SEQ ID NO: 4, will include or exclude naturally occurring sequences.

In certain embodiments, the antibody or antigen-binding fragment further comprising: H-CDR1, H-CDR2, and H-CDR3 selected from (i)-(iii) as set forth in Table 1:
(i) H-CDR1 selected from SEQ ID NO:13;
(ii) H-CDR2 selected from SEQ ID NO: 15;
(iii) H-CDR3 selected from SEQ ID NO:17, respectively;
and comprising L-CDR1, L-CDR2 and L-CDR3 selected from (iv)-(vi):
(iv) L-CDR1 selected from SEQ ID NO: 6;
(v) L-CDR2 selected from SEQ ID NO:8; and
(vi) L-CDR3 selected from SEQ ID NO: 10, respectively.
In certain embodiments, antibody or antigen-binding fragment thereof, comprises a heavy chain region, wherein the heavy chain region comprises a complementarity determining region (CDR) amino acid sequence of at least about 80% homology to the amino acid sequence selected from SEQ ID NOs: 13, 15 or 17. In certain embodiments, the antibody or antigen-binding fragment thereof, comprise a light chain region, wherein the light chain region comprises a complementarity determining region (CDR) amino acid sequence of at least about 80% homology to the amino acid sequence selected from SEQ ID NOs: 6, 8 or 10. In certain embodiments, the antibody or antigen-binding fragment excludes naturally occurring sequences. In certain embodiments, the antibody or antigen-binding fragment includes naturally occurring sequences.

In certain embodiments, the antibody or antigen-binding fragment further comprising: H-FW1, H-FW2, H-FW3, and H-FW4, selected from (i)-(iv) as set forth in Table 1:
(i) H-FW1 selected from SEQ ID NO: 12;
(ii) H-FW2 selected from SEQ ID NO: 14;
(iii) H-FW3 selected from SEQ ID NO: 16,
(iv) H-FW4 selected from SEQ ID NO: 18, respectively;
and comprising L-FW1, L-FW2, L-FW3, and L-FW4 selected from (v)-(viii):
(v) L-FW1 selected from SEQ ID NO: 5;
(vi) L-FW2 selected from SEQ ID NO: 7;
(vii) L-FW3 selected from SEQ ID NO: 9,
(viii) L-FW4 selected from SEQ ID NO: 11, respectively.

In one aspect, the present disclosure provides an antibody, or an antigen-binding fragment thereof, produced by the hybridoma designated as Ms deposited under ATCC Accession Number PTA-122679.

In one aspect, the present disclosure provides a hybridoma designated as Ms deposited under ATCC Accession Number PTA-122679.

In certain aspects, the present disclosure provides an antibody, or an antigen-binding fragment thereof, comprising: a heavy chain variable domain (VH) comprises of an amino acid sequence of at least about 80% sequence homology to the amino acid sequence set forth in SEQ ID NO: 21 and/or a light chain variable domain (VL) comprises of an amino acid sequence of at least about 80% homology to the amino acid sequence as set forth in SEQ ID NO: 22. (Table 2). In some aspects, the amino acid sequence of the heavy chain variable domain (VH), which comprises of an amino acid sequence of at least about 80% sequence homology to the amino acid sequence set forth in SEQ ID NO: 21, will include or exclude naturally occurring sequences. In some aspects, the amino acid sequence of the light chain variable domain (LH), which comprises of an amino acid sequence of at least about 80% sequence homology to the amino acid sequence set forth in SEQ ID NO: 22, will include or exclude naturally occurring sequences.

In certain embodiments, the antibody, or antigen-binding fragment further comprising H-CDR1, H-CDR2, and H-CDR3 selected from (i)-(iii) as set forth in Table 2:
(i) H-CDR1 selected from SEQ ID NO:31;
(ii) H-CDR2 selected from SEQ ID NO: 33;
(iii) H-CDR3 selected from SEQ ID NO:35, respectively; and comprising L-CDR1, L-CDR2 and L-CDR3 selected from (iv)-(vi):
(iv) L-CDR1 selected from SEQ ID NO: 24;
(v) L-CDR2 selected from SEQ ID NO:26; and
(vi) L-CDR3 selected from SEQ ID NO: 28, respectively.
In certain embodiments the antibody, or antigen-binding fragment thereof, comprises a heavy chain region, wherein the heavy chain region comprises a complementarity determining region (CDR) amino acid sequence of at least about 80% homology to the amino acid sequence selected from SEQ ID NOs: 31, 33, or 35. In certain embodiments the antibody, or antigen-binding fragment thereof, comprises a light chain region, wherein the light chain region comprises a complementarity determining region (CDR) amino acid sequence of at least about 80% homology to the amino acid sequence selected from SEQ ID NOs: 24, 26 or 28. In certain embodiments the antibody or antigen-binding fragment includes or excludes naturally occurring sequences.

In certain embodiments, the antibody or antigen-binding fragment further comprising: H-FW1, H-FW2, H-FW3 and H-FW4, selected from (i)-(iv) as set forth in Table 2:
(i) H-FW1 selected from SEQ ID NO: 30;
(ii) H-FW2 selected from SEQ ID NO: 32;
(iii) H-FW3 selected from SEQ ID NO: 34,
(iv) H-FW4 selected from SEQ ID NO: 36, respectively; and comprising L-FW1, L-FW2, L-FW3 and L-FW4 selected from (v)-(viii):
(v) L-FW1 selected from SEQ ID NO: 23;
(vi) L-FW2 selected from SEQ ID NO: 25;
(vii) L-FW3 selected from SEQ ID NO: 27,
(viii) L-FW4 selected from SEQ ID NO: 29, respectively.

In one aspect, the present disclosure provides an antibody, or an antigen-binding fragment thereof, produced by the hybridoma designated as 1G1s deposited under ATCC Accession Number PTA-122678.

In one aspect, the present disclosure provides a hybridoma designated as 1G1s deposited under ATCC Accession Number PTA-122678.

In certain aspects, the present disclosure provides an antibody, or an antigen-binding fragment thereof, comprises a heavy chain variable domain (VH) comprises of an amino acid sequence of at least about 80% sequence homology to the amino acid sequence set forth in SEQ ID NO: 39 and/or a light chain variable domain (VL) comprises an amino acid sequence of at least about 80% homology to the amino acid sequence as set forth in SEQ ID NO: 40. (Table 3). In some aspects the amino acid sequence of the heavy chain variable domain (VH), which comprises an amino acid sequence of at least about 80% sequence homology to the amino acid sequence set forth in SEQ ID NO: 39, will include or exclude naturally occurring sequences. In some aspects the amino acid sequence of the light chain variable domain (VH), which comprises an amino acid sequence of at least about 80% sequence homology to the amino acid sequence set forth in SEQ ID NO: 40, will include or exclude naturally occurring sequences.

In certain embodiments, the antibody, or antigen-binding fragment thereof further comprising H-CDR1, H-CDR2, and H-CDR3 selected from (i)-(iii) as set forth in Table 3:
(i) H-CDR1 selected from SEQ ID NO:49;
(ii) H-CDR2 selected from SEQ ID NO: 51;
(iii) H-CDR3 selected from SEQ ID NO:53, respectively; and comprising L-CDR1, L-CDR2 and L-CDR3 selected from (iv)-(vi):
(iv) L-CDR1 selected from SEQ ID NO: 42;
(v) L-CDR2 selected from SEQ ID NO:44; and
(vi) L-CDR3 selected from SEQ ID NO: 46, respectively.
In certain embodiments of the antibody, or antigen-binding fragment thereof, comprises a heavy chain region, wherein the heavy chain region comprises a complementarity determining region (CDR) amino acid sequence of at least about 80% homology to the amino acid sequence selected from SEQ ID NOs: 49, 51 or 53. In certain embodiments the antibody, or antigen-binding fragment thereof, comprises a light chain region, wherein the light chain region comprises a complementarity determining region (CDR) amino acid sequence of at least about 80% homology to the amino acid sequence selected from SEQ ID NOs: 42, 44 or 46. In certain embodiments the antibody or antigen-binding fragment includes or excludes naturally occurring sequences.

In certain embodiments, the antibody or antigen-binding fragment further comprising: H-FW1, H-FW2, H-FW3 and H-FW4, selected from (i)-(iv) as set forth in Table 3:
(i) H-FW1 selected from SEQ ID NO: 48;
(ii) H-FW2 selected from SEQ ID NO: 50;
(iii) H-FW3 selected from SEQ ID NO: 52,
(iv) H-FW4 selected from SEQ ID NO: 54, respectively; and comprising L-FW1, L-FW2, L-FW3 and L-FW4 selected from (v)-(viii):
(v) L-FW1 selected from SEQ ID NO: 41;
(vi) L-FW2 selected from SEQ ID NO: 43;
(vii) L-FW3 selected from SEQ ID NO: 45,
(viii) L-FW4 selected from SEQ ID NO: 47, respectively.

In one aspect, the present disclosure provides an antibody, or an antigen-binding fragment thereof, produced by the hybridoma designated as 2F20s deposited under ATCC Accession Number PTA-122676.

In one aspect, the present disclosure provides a hybridoma designated as 2F20s deposited under ATCC Accession Number PTA-122676.

In certain embodiments, the exemplary antibody or antigen-binding fragment thereof, includes variable domain capable of binding to one or more carbohydrate antigens.

In certain embodiments, the antibody or antigen-binding fragment thereof, targets carbohydrate antigen SSEA-4 (Neu5Acα2→3Galβ1→3GalNAcβ1→3Galα1→4Galβ1→4Glcβ1) (SSEA-4 hexasaccharide).

In certain aspects, the present disclosure provides an antibody or binding fragment thereof, wherein the antibody or binding fragment thereof comprises VH selected from SEQ ID NO: 3, SEQ ID NO:21, or SEQ ID NO:39 and VL selected from SEQ ID NO: 4, SEQ ID NO:22 or SEQ ID NO:40. In some aspects the present disclosure provides an antibody, or an antigen-binding fragment thereof, comprising: a heavy chain variable domain (VH) comprises an amino acid sequence of at least about 80% sequence homology to the amino acid sequence set forth in SEQ ID NOs:3, 21 or 39 and/or a light chain variable domain (VL) comprises an amino acid sequence of at least about 80% homology to the amino acid sequence as set forth in SEQ ID NO: 4, 22 or 40. In some aspects the antibody, or an antigen-binding fragment thereof may include or exclude natural sequences.

In certain embodiments, the antibody or antigen-binding fragment thereof is selected from:
(a) a whole immunoglobulin molecule;
(b) an scFv;
(c) a Fab fragment;
(d) an F(ab')$_2$; or
(e) a disulfide linked Fv.

In certain embodiments, the antibody is a humanized antibody.

In certain embodiments, the antibody is an IgG or IgM.

In one aspect, the present disclosure provides a pharmaceutical composition comprises an antibody or an antigen-binding fragment thereof of any one of claims 1-21; and at least one pharmaceutically acceptable carrier.

In certain embodiments, the pharmaceutical composition further comprises at least one additional therapeutic agent.

In one aspect, the present disclosure provides a method for inhibiting the proliferation of cancer cells, comprising the administering of an effective amount of an exemplary pharmaceutical composition to a subject in need thereof, wherein the proliferation of cancer cells is inhibited.

In certain embodiments, the present disclosure provides a method of treating cancer in a subject. The method comprises administering to a subject in need thereof an effective amount of the exemplary antibody described herein.

In certain embodiments, the cancer is selected from the group consisting breast cancer, lung cancer, esophageal cancer, rectal cancer, biliary cancer, liver cancer, buccal cancer, gastric cancer, colon cancer, nasopharyngeal cancer, kidney cancer, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer, basal cell carcinoma, squamous cell carcinoma, melanoma, or brain tumor.

In one aspect, the present disclosure provides a method for staging cancer in a subject, comprising:
(a) applying one or more antibodies that detect the expression of SSEA-4 to a cell or tissue sample obtained from the subject;
(b) assaying the binding of one or more antibodies to the cell or the tissue sample;
(c) comparing the binding with a normal control to determine the presence of the cancer in the subject; and
(d) categorizing disease progression stage based on relative levels of corresponding antibody binding compared to normal baseline index.

The details of one or more embodiments of the invention are set forth in the description below. Other features and/or advantages of the present invention will be apparent from the drawings, detailed description of several embodiments, and also from the appending claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9 shows FACS binding assay results of exemplary SSEA-4 antibodies Ms, 1G1s, 2F20s, and commercial clone MC-813-70 to various cancer and non-cancer cell lines. The cancer cell lines tested were MCF-7 (breast cancer), MDA-MB231 (breast cancer), HPAC (pancreatic cancer), LN-18 (glioblastoma) and LL-2 (Lewis lung carcinoma). The non-tumorigenic cell lines tested were HK2 (kidney, cortex/proximal tubule), NL-20 (bronchial epithelium), THLE-3 (liver, normal cell) and HuMEC (human mammary epithelial cells).

FIG. 11 shows the characterization of epitopes by titration ELISA.

DETAILED DESCRIPTION OF THE INVENTION

Figure 1:
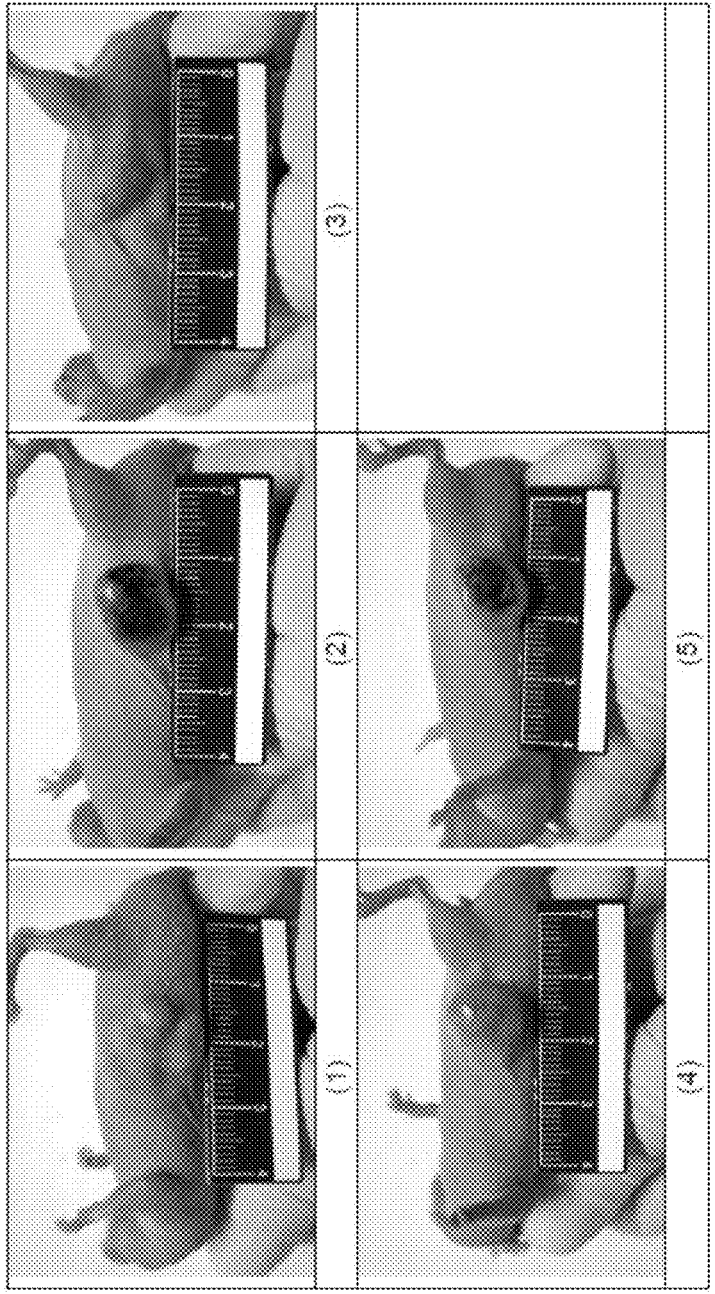
FIG. 1 shows pictures of BALB/c nude male mice with HPAC implanted tumors on Day 36 after treatment with Vehicle, 10 mL/kg×10, intraperitoneally, twice weekly.
Figure 2:
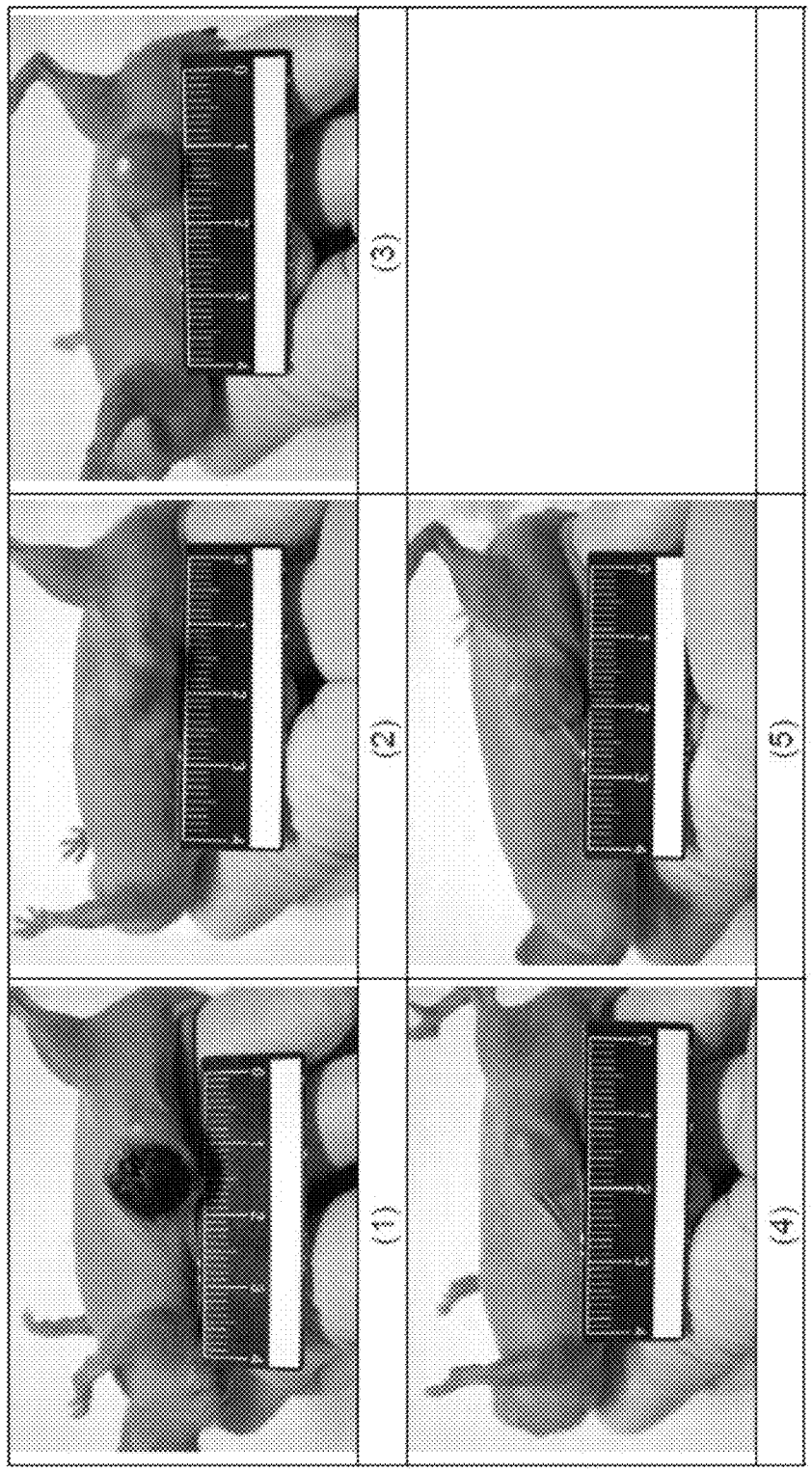
FIG. 2 shows pictures of BALB/c nude male mice with HPAC implanted tumors on Day 36 after treatment with Globo H-2C2, 0.4 mg/kg×10, intraperitoneally, twice weekly.
Figure 3:
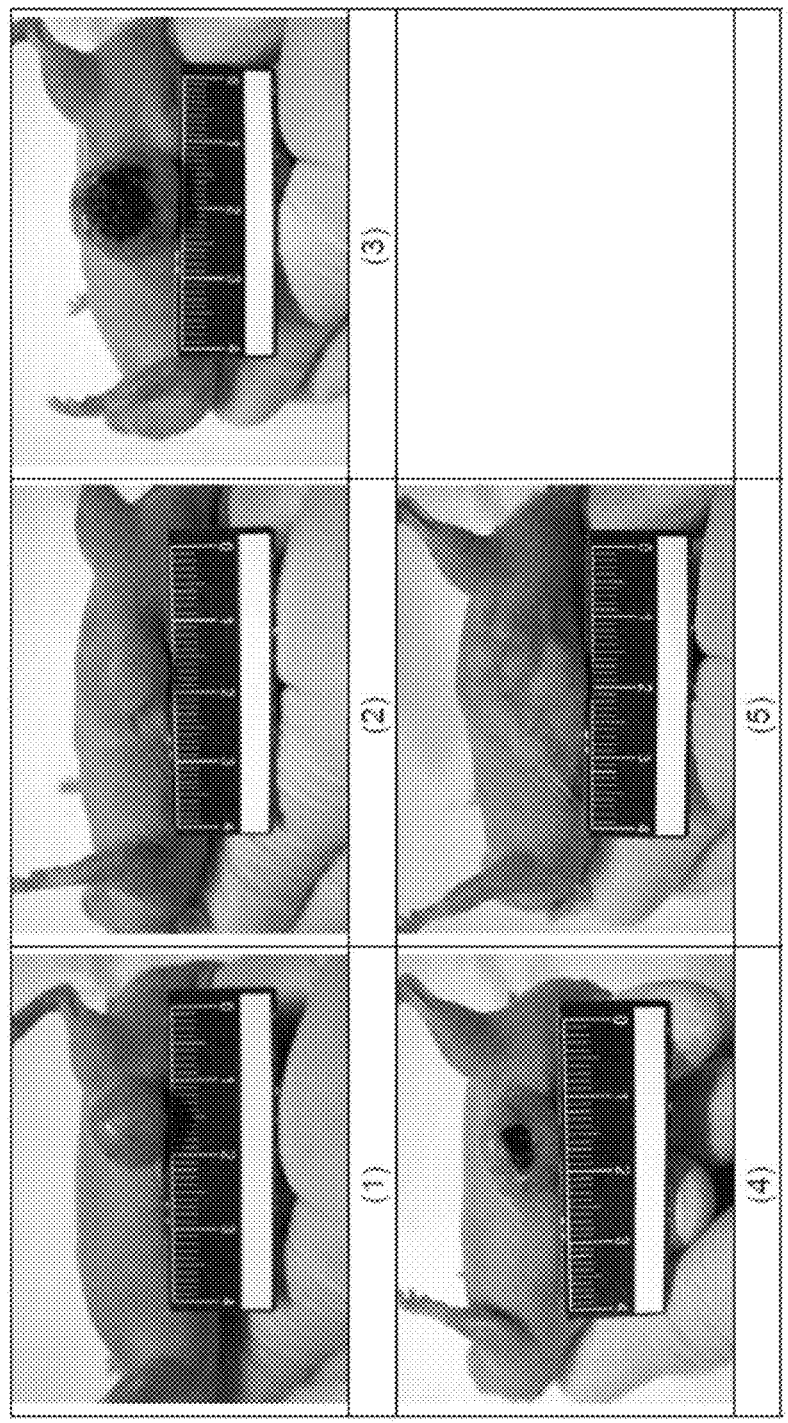
FIG. 3 shows pictures of BALB/c nude male mice with HPAC implanted tumors on Day 36 after treatment with commercial SSEA-4 antibody (MC-813-70), 0.4 mg/kg×10, intraperitoneally, twice weekly.
Figure 4:
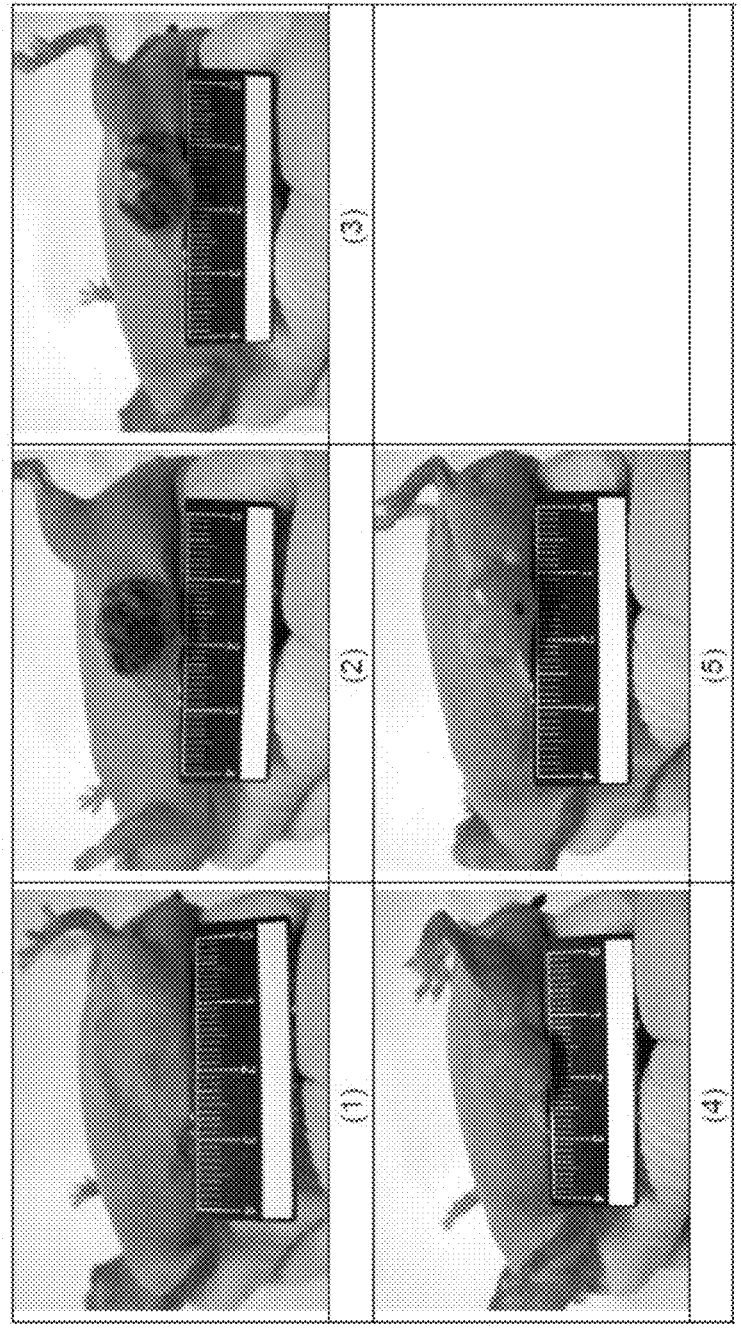
FIG. 4 shows pictures of BALB/c nude male mice with HPAC implanted tumors on Day 36 after treatment with 1G1s, 0.4 mg/kg×10, intraperitoneally, twice weekly.
Figure 5:
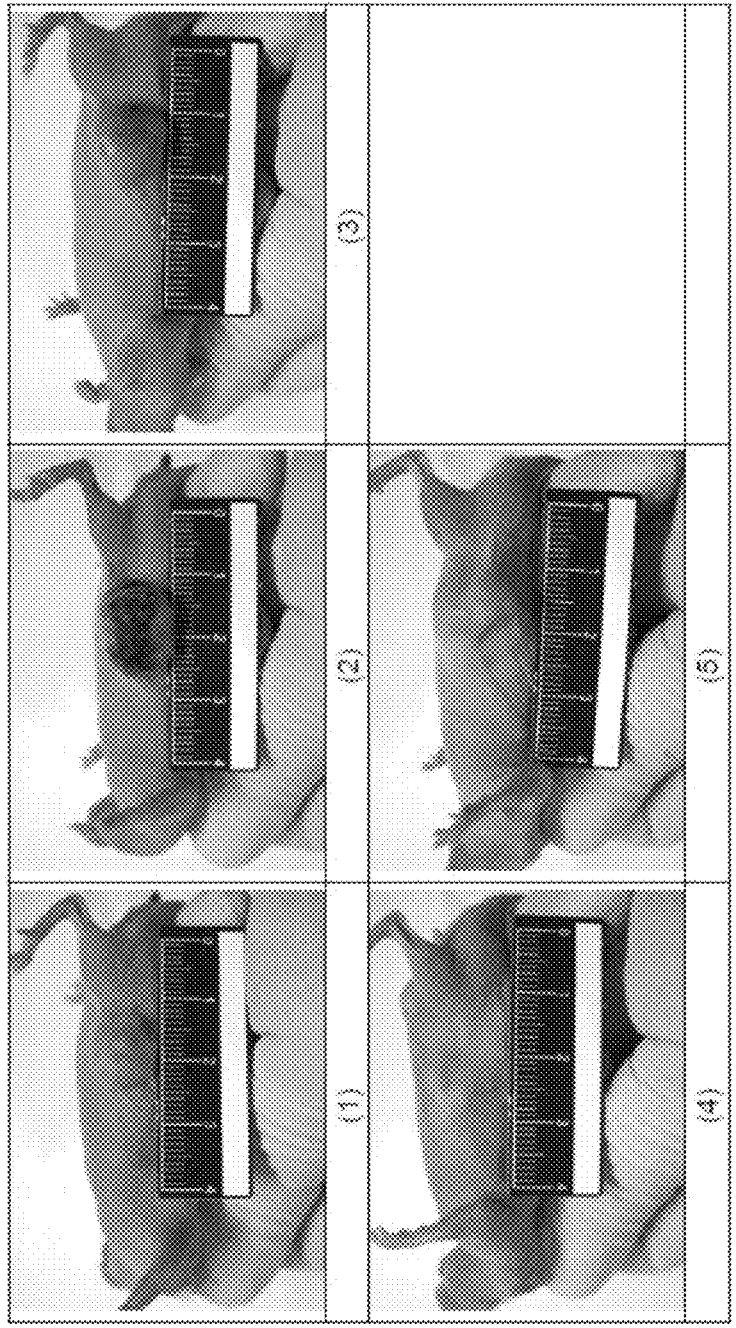
FIG. 5 shows pictures of BALB/c nude male mice with HPAC implanted tumors on Day 36 after treatment with 1J1s, 0.4 mg/kg×10, intraperitoneally, twice weekly.
Figure 6:
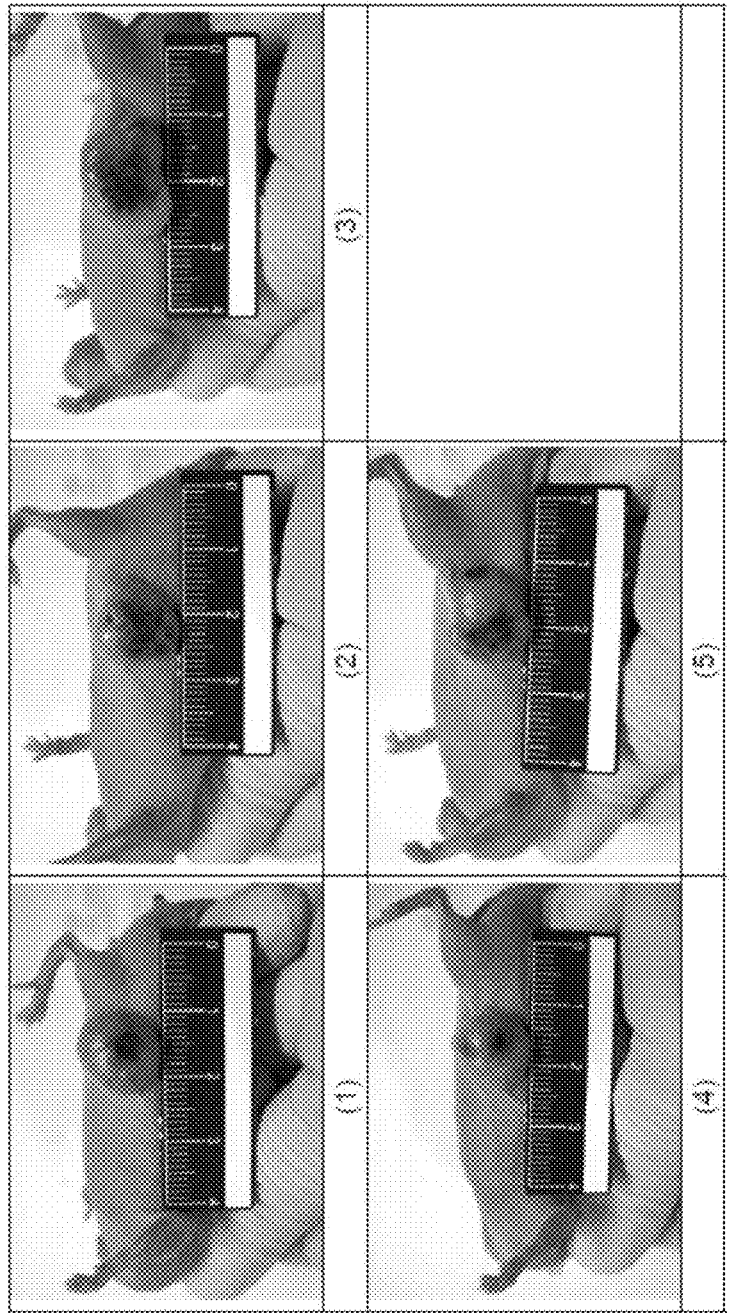
FIG. 6 shows pictures of BALB/c nude male mice with HPAC implanted tumors on Day 36 after treatment with 2F20s, 0.4 mg/kg×10, intraperitoneally, twice weekly.

Antibody methods and compositions directed to the markers for use in diagnosing and treating a broad spectrum of cancers are provided. Anti-SSEA-4 antibodies were developed and disclosed herein. Methods of use include, without limitation, cancer therapies and diagnostics. The antibodies described herein can bind to a broad spectrum of SSEA-4-expressing cancer cells, thereby facilitating cancer diagnosis and treatment. Cells that can be targeted by the antibodies include carcinomas, such as those in skin, blood, lymph node, brain, lung, breast, mouse, esophagus, stomach, liver, bile duct, pancreas, colon, kidney, cervix, ovary, prostate cancer, etc.

Definitions

The practice of the present invention employs, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide, or a proteoglycan. Glycans usually consist solely of O-glycosidic linkages between monosaccharides. For example, cellulose is a glycan (or more specifically a glucan) composed of ß-1,4-linked D-glucose, and chitin is a glycan composed of ß-1,4-linked N-acetyl-D-glucosamine. Glycans can be homopolymers or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

As used herein, the term "antigen" is defined as any substance capable of eliciting an immune response.

As used herein, the term "immunogenicity" refers to the ability of an immunogen, antigen, or vaccine to elicit an immune response.

As used herein, the term "epitope" is defined as the parts of an antigen molecule which contact the antigen binding site of an antibody or a T cell receptor.

As used herein, the term "vaccine" refers to a preparation that contains an antigen, consisting of whole disease-causing organisms (killed or weakened) or components of such organisms, such as proteins, peptides, or polysaccharides, that is used to confer immunity against the disease that the organisms cause. Vaccine preparations can include or exclude any one of natural, synthetic or recombinantly derived preparations. Recombinantly derived preparations can be obtained, for example, by recombinant DNA technology.

As used herein, the term "antigen specific" refers to a property of a cell population such that the supply of a particular antigen, or a fragment of the antigen, results in specific cell proliferation.

As used herein, the term "specific binding," refers to the interaction between binding pairs (e.g., an antibody and an antigen). In various instances, specific binding can be embodied by an affinity constant of about $10^{-6}$ moles/liter, about $10^{-7}$ moles/liter, or about $10^{-8}$ moles/liter, or less.

The phrase "substantially similar", "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the differences between the two values to be of little or no biological and/or statistical significance within the context of the biological characteristic measured by said values (e.g., Kd values, anti-viral effects, etc.). The differences between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The differences between said two values are, for example, greater than about 10%, greater than about 20%, greater than about 30%, greater than about 40%, and/or greater than about 50% as a function of the value for the reference/comparator molecule.

"Binding affinity", as used herein, generally refers to the strength of the sum of total noncovalent interactions between a single binding site of a molecule (e.g., an antibody) and its binding partner (e.g., an antigen). Unless indicated otherwise, as used herein, "binding affinity" refers to the intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In certain embodiments, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 μg/mL of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc, Cat #269620), 100 pM or 26 pM [125I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μL/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C., with immobilized antigen CMS chips at ~10 response units (RU). Briefly, carboxymethylated dextran biosensor chips (CMS, BIAcore Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 μg/mL (~0.2 μM) before injection at a flow rate of 5 μL/minute to achieve approximately 10 response units (RU) of coupled protein. Following the injection of antigen, 1 M ethanolamine is injected to block unreacted groups. In each experiment, a spot was activated and ethanolamine blocked without immobilizing protein, to be used for reference subtraction. For kinetics measurements, two-fold serial dilutions of Fab (0.78 nM to 500 nM) are injected in PBS with 0.05% Tween 20 (PBST) at 25° C. at a flow rate of approximately 25 μL/min. Association rates (kon) and dissociation rates (koff) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio koff/kon. See, e.g., Chen, Y., et al., (1999) J. Mol Biol 293:865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophometer (ThermoSpectronic) with a stirred cuvette.

An "on-rate" or "rate of association" or "association rate" or "kon" according to this invention can also be determined with the same surface plasmon resonance technique described above using a BIAcore™-2000 or a BIAcore™-3000 (BIAcore, Inc., Piscataway, N.J.) at 25° C. with immobilized antigen CMS chips at or "association rate" or "kon" according to this invention can also be determined with the same surface plasmon N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 μg/mL (~0.2 μM) before injection at a flow rate of 5 μL/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μL/min. Association rates (kon) and dissociation rates (koff) are calculated using a simple one-to-one Langmuir binding model (BIAcore Evaluation Software version 3.2) by simultaneously fitting the association and dissociation sensorgram. The equilibrium dissociation constant (Kd) was calculated as the ratio koff/kon. See, e.g., Chen, Y., et al., (1999) J. Mol Biol 293:865-881. However, if the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophometer (ThermoSpectronic) with a stirred cuvette.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, tituted with amines or organic capping group moieties of from 1 to 20 carbon atoms. Other hydroxyls may also be derivatized to standard protecting groups. Polynucleotides can also contain side. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20C) optionally containing an ether (from 1 to 20 carbon atoms. Other hydroxyls may also be derivatized to standard protecting nucleotide need be identical. The preceding description applies to all polynucleotides referred to herein, including RNA and DNA.

"Oligonucleotide," as used herein, generally refers to short, single-stranded, synthetic polynucleotides that are typically, but not necessarily, less than about 200 nucleotides in length. The terms "oligonucleotide" and "polynucleotide" are not mutually exclusive. The description above for polynucleotides is equally and fully applicable to oligonucleotides.

"Antibodies" (Abs) and "immunoglobulins" (Igs), as used herein, are glycoproteins having the same structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin", as used herein, are used interchangeably in the broadest sense and include monoclonal antibodies (e.g., full length or intact monoclonal antibodies), polyclonal antibodies, monovalent, multivalent antibodies, multi specific antibodies (e.g., bispecific antibodies so long as they exhibit the desired biological activity), and may also include certain antibody fragments, as described in greater detail herein. An antibody can be chimeric, human, humanized, and/or affinity matured.

The "variable region" or "variable domain" of an antibody, as used herein, refers to the amino-terminal domains of heavy or light chain of the antibody. These domains are generally the most variable parts of an antibody and contain the antigen-binding sites.

The term "variable", as used herein, refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called bulins) can be assigned to different classes. There are five three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments", as used herein, comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise an antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. In certain embodiments, the monoclonal antibody may exclude natural sequences. In some aspects, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (e.g., epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2nd ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

Antibodies of the present invention also include chimerized or humanized monoclonal antibodies generated from antibodies of the present invention.

The antibodies can be full-length or can comprise a fragment (or fragments) of the antibody having an antigen-binding portion, including, but not limited to, Fab, F(ab')$_2$, Fab', F(ab)', Fv, single chain Fv (scFv), bivalent scFv (bi-scFv), trivalent scFv (tri-scFv), Fd, dAb fragment (e.g., Ward et al, Nature, 341:544-546 (1989)), an CDR, diabodies, triabodies, tetrabodies, linear antibodies, single-chain antibody molecules, and multispecific antibodies formed from antibody fragments. Single chain antibodies produced by joining antibody fragments using recombinant methods, or a synthetic linker, are also encompassed by the present invention. Bird et al. Science, 1988, 242:423-426. Huston et al, Proc. Natl. Acad. Sci. USA, 1988, 85:5879-5883.

The antibodies or antigen-binding portions thereof of the present invention may be monospecific, bi-specific or multispecific.

All antibody isotypes are encompassed by the present invention, including IgG (e.g., $IgG_1$, $IgG_2$, $IgG_3$, $IgG_4$), IgM, IgA $IgA_2$), IgD or IgE (all classes and subclasses are encompassed by the present invention). The antibodies or antigen-binding portions thereof may be mammalian (e.g., mouse, human) antibodies or antigen-binding portions thereof. The light chains of the antibody may be of kappa or lambda type.

Thus, anti-cancer antibodies of the present invention include in combination with a heavy chain or light chain variable region, a heavy chain or light chain constant region, a framework region, or any portion thereof, of non-murine origin, preferably of human origin, which can be incorporated into an antibody of the present invention.

Antibodies with a variable heavy chain region and a variable light chain region that are at least about 70%, at least about 75%, at least about 80%, at least about 81%, at least about 82%, at least about 83%, at least about 84%, at least about 85%, at least about 86%, at least about 87%>, at least about 88%>, at least about 89%>, at least about 90%>, at least about 91>, at least about 92%>, at least about 93%>, at least about 94%>, at least about 95%), at least about 96%>, at least about 97%>, at least about 98%>, at least about 99%> or about 100% homologous to the variable heavy chain region and variable light chain region of the antibody produced by the reference antibody, and can also bind to a carbohydrate antigen (e.g., SSEA-4). Homology can be present at either the amino acid or nucleotide sequence level. In some aspects the sequence of the antibodies having the recited homologies to either the amino acid or nucleotide sequences will exclude naturally occurring antibody sequences. In some aspects the sequence of the antibodies having the recited homologies to either the amino acid or nucleotide sequences will include naturally occurring antibody sequences.

In certain embodiments, CDRs corresponding to the CDRs in Table 1-3 have sequence variations. For example, CDRs, in which 1, 2, 3, 4, 5, 6, 7 or 8 residues, or less than 20%, less than 30%, or less than about 40% of total residues in the CDR, are substituted or deleted can be present in an antibody (or antigen-binding portion thereof) that binds a carbohydrate antigen.

The antibodies or antigen-binding portions may be peptides. Such peptides can include variants, analogs, orthologs, homologs and derivatives of peptides, that exhibit a biological activity, e.g., binding of a carbohydrate antigen. The peptides may contain one or more analogs of an amino acid (including, for example, non-naturally occurring amino acids, amino acids which only occur naturally in an unrelated biological system, modified amino acids from mammalian systems etc.), peptides with substituted linkages, as well as other modifications known in the art.

Also within the scope of the invention are antibodies or antigen-binding portions thereof in which specific amino acids have been substituted, deleted, or added. In an exemplary embodiment, these alternations do not have a substantial effect on the peptide's biological properties such as binding affinity. In another exemplary embodiment, antibodies may have amino acid substitutions in the framework region, such as to improve binding affinity of the antibody to the antigen. In yet another exemplary embodiment, a selected, small number of acceptor framework residues can be replaced by the corresponding donor amino acids. The donor framework can be a mature or germline human antibody framework sequence or a consensus sequence. Guidance concerning how to make phenotypically silent amino acid substitutions is provided in Bowie et al., Science, 247: 1306-1310 (1990). Cunningham et al, Science, 244: 1081-1085 (1989). Ausubel (ed.), Current Protocols in Molecular Biology, John Wiley and Sons, Inc. (1994). T. Maniatis, E. F. Fritsch and J. Sambrook, Molecular Cloning: A Laboratory Manual, Cold Spring Harbor laboratory, Cold Spring Harbor, N.Y. (1989). Pearson, Methods Mol. Biol. 243:307-31 (1994). Gonnet et al., Science 256: 1443-45 (1992).

The antibody, or antigen-binding portion thereof, can be derivatized or linked to another functional molecule. For example, an antibody can be functionally linked (by chemical coupling, genetic fusion, noncovalent interaction, etc.) to one or more other molecular entities, such as another antibody, a detectable agent, a cytotoxic agent, a pharmaceutical agent, a protein or peptide that can mediate association with another molecule (such as a streptavidin core region or a polyhistidine tag), amino acid linkers, signal sequences, immunogenic carriers, or ligands useful in protein purification, such as glutathione-S-transferase, histidine tag, and staphylococcal protein A. One type of derivatized protein is produced by crosslinking two or more proteins (of the same type or of different types). Suitable crosslinkers include those that are heterobifunctional, having two distinct reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, 111. Useful detectable agents with which a protein can be derivatized (or labeled) include fluorescent compounds, various enzymes, prosthetic groups, luminescent materials, bioluminescent materials, and radioactive materials. Non-limiting, exemplary fluorescent detectable agents include fluorescein, fluorescein isothiocyanate, rhodamine, and, phycoerythrin. A protein or antibody can also be derivatized with detectable enzymes, such as alkaline phosphatase, horseradish peroxidase, beta-galactosidase, acetylcholinesterase, glucose oxidase and the like. A protein can also be derivatized with a prosthetic group (e.g., streptavidin/biotin and avidin/biotin).

Nucleic acids encoding a functionally active variant of the present antibody or antigen-binding portion thereof are also encompassed by the present invention. These nucleic acid molecules may hybridize with a nucleic acid encoding any of the present antibody or antigen-binding portion thereof under medium stringency, high stringency, or very high stringency conditions. Guidance for performing hybridization reactions can be found in Current Protocols in Molecular Biology, John Wiley & Sons, N.Y. 6.3.1-6.3.6, 1989, which is incorporated herein by reference. Specific hybridization conditions referred to herein are as follows: 1) medium stringency hybridization conditions: 6×SSC at about 45° C., followed by one or more washes in 0.2×SSC, 0.1% SDS at 60° C.; 2) high stringency hybridization conditions: 6×SSC at about 45° C., followed by one or more washes in 0.2×SSC, 0.1% SDS at 65° C.; and 3) very high stringency hybridization conditions: 0.5 M sodium phosphate, 7% SDS at 65° C., followed by one or more washes at 0.2×SSC, 1% SDS at 65° C.

A nucleic acid encoding the present antibody or antigen-binding portion thereof may be introduced into an expression vector that can be expressed in a suitable expression system, followed by isolation or purification of the expressed antibody or antigen-binding portion thereof. Optionally, a nucleic acid encoding the present antibody or antigen-binding portion thereof can be translated in a cell-free translation system. U.S. Pat. No. 4,816,567. Queen et al, Proc Natl Acad Sci USA, 86: 10029-10033 (1989).

The present antibodies or antigen-binding portions thereof can be produced by host cells transformed with DNA encoding light and heavy chains (or portions thereof) of a desired antibody. Antibodies can be isolated and purified from these culture supernatants and/or cells using standard techniques. For example, a host cell may be transformed with DNA encoding the light chain, the heavy chain, or both, of an antibody. Recombinant DNA technology may also be used to remove some or all of the DNA encoding either or both of the light and heavy chains that is not necessary for binding (e.g., the constant region).

The present nucleic acids can be expressed in various suitable cells, including prokaryotic and eukaryotic cells, e.g., bacterial cells, (e.g., E. coli), yeast cells, plant cells, insect cells, and mammalian cells. A number of mammalian cell lines are known in the art and include immortalized cell lines available from the American Type Culture Collection (ATCC). Non-limiting examples of the cells include all cell lines of mammalian origin or mammalian-like characteristics, including but not limited to, parental cells, derivatives and/or engineered variants of monkey kidney cells (COS, e.g., COS-1, COS-7), HEK293, baby hamster kidney (BHK, e.g., BHK21), Chinese hamster ovary (CHO), NSO, PerC6, BSC-1, human hepatocellular carcinoma cells (e.g., Hep G2), SP2/0, HeLa, Madin-Darby bovine kidney (MDBK), myeloma and lymphoma cells. The engineered variants include, e.g., glycan profile modified and/or site-specific integration site derivatives.

The present invention also provides for cells comprising the nucleic acids described herein. The cells may be a hybridoma or transfectant.

Alternatively, the present antibody or antigen-binding portion thereof can be synthesized by solid phase procedures well known in the art. Solid Phase Peptide Synthesis: A Practical Approach by E. Atherton and R. C. Sheppard, published by IRL at Oxford University Press (1989). Methods in Molecular Biology, Vol. 35: Peptide Synthesis Protocols (ed. M. W. Pennington and B. M. Dunn), chapter 7. Solid Phase Peptide Synthesis, 2nd Ed., Pierce Chemical Co., Rockford, Ill. (1984). G. Barany and R. B. Merrifield, The Peptides: Analysis, Synthesis, Biology, editors E. Gross and J. Meienhofer, Vol. 1 and Vol. 2, Academic Press, New York, (1980), pp. 3-254. M. Bodansky, Principles of Peptide Synthesis, Springer-Verlag, Berlin (1984).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)).

"Framework" or "FW" residues, as used herein, are those variable domain residues other than the hypervariable region residues as herein defined.

The term "variable domain residue numbering as in Kabat" or "amino acid position numbering as in Kabat" and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (e.g., residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments, as used herein, comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies", as used herein, refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

A "human antibody", as used herein, is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured antibody", as used herein, is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking antibody" or an "antagonist antibody", as used herein, is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder", as used herein, is any condition that would benefit from treatment with an antibody of the invention. This includes chronic and acute disorders or diseases including those pathological conditions which predispose the mammal to the disorder in question. Non-limiting examples of disorders to be treated herein include cancer.

The terms "cell proliferative disorder" and "proliferative disorder", as used herein, refer to disorders that are associated with some degree of abnormal cell proliferation. In one embodiment, the cell proliferative disorder is cancer.

"Tumor" as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous", as used herein, refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulvar cancer, thyroid cancer, hepatic carcinoma, leukemia and other lymphoproliferative disorders, and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In certain embodiments, antibodies of the invention are used to delay development of a disease or disorder.

As used herein, "antibody-drug conjugates (ADCs)" refers to an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

As used herein, "T cell surface antigen" refers to an antigen can include representative T cell surface markers known in the art, including T-cell antigen receptor (TcR), which is the principle defining marker of all T-cells which are used by the T-cell for specific recognition of MHC-associated peptide antigens. An exemplar associated with the TcR is a complex of proteins known as CD3, which participate in the transduction of an intracellular signal following TcR binding to its cognate MHC/antigen complex. Other examples of T cell surface antigen can include (or exclude) CD2, CD4, CD5, CD6, CD8, CD28, CD40L and/or CD44.

An "individual" or a "subject", as used herein, is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment, as used herein, refers to any animal classified as a mammal, including humans, domestic and farm animals, and zoo, sports, or pet animals, such as dogs, horses, cats, cows, etc. In certain embodiments, the mammal is human.

An "effective amount", as used herein, refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32, Pb212 and radioactive isotopes of Lu), chemotherapeutic agents (e.g., methotrexate, adriamycin, *vinca* alkaloids, vincristine, vinblastine, etoposide, doxorubicin, melphalan, mitomycin C, chlorambucil, daunorubicin, or other intercalating agents), enzymes, and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent", as used herein, is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1l (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Antibodies Targeting SSEA-4

One aspect of the present disclosure features the new antibody targeting the SSEA-4 related antigens.

The mAb 1J1s (ATCC Accession No. PTA-122679) is a monoclonal antibody, produced by the hybridoma cell line (ATCC Accession No. PTA-122679). The antibody described herein can contain the same VH and VL chains as antibody 1J1s. Antibodies binding to the same epitope as 1J1s are also within the scope of this disclosure.

Exemplars and their amino acid and nucleic acid structures/sequences are provided below:

TABLE 1

Amino Acid and Nucleotide Sequences of Antibody 1J1s

| SEQ ID NO | DESCRIPTION | SEQUENCE |
|---|---|---|
| 1 | 1J1s VH nucleotide sequence | CAGGTGCAGCTGAAGGAGTCAGGACCTGGCCTGGTGGCGCCCT CACAGAGCCTGTCCATCACTTGCACTGTCTCTGGGTTTTCATTA ATCAGCTATGGTGTAGACTGGGTTCGCCAGCCTCCAGGAAAGG GTCTGGAGTGGCTGGGAGTAATATGGGGTGGTGGAAATACAA |

TABLE 1-continued

Amino Acid and Nucleotide Sequences of Antibody 1J1s

| SEQ ID NO | DESCRIPTION | SEQUENCE |
|---|---|---|
| | | ATTATAATTCATCTCTCATGTCCAGACTGAGCATCAGCAAAGA CAACTCCAAGAGCCAAGTTTTCTTAAAAATGAACAGTCTGCAA ACTGATGACACAGCCATGTACTACTGTGCCAAAACTGGGACCG GATATGCTTTGGAGTACTGGGGTCAAGGAACCTCAGTCACCGT CTCCTCC |
| 2 | 1J1s VL nucleotide sequence | GAAAATGTTCTCACCCAGTCTCCAGCAATCATGTCTGCATCTCC AGGGGAAAAGGTCACCATGACCTGCAGTGCCAGGTCAAGTGT AAGTTACATGCACTGGTACCAGCAGAAGTCAACCGCCTCCCCC AAACTCTGGATTTATGACACATCCAAACTGGCTTCTGGAGTCC CAGGTCGCTTCAGTGGCAGTGGGTCTGGAAACTCTTACTCTCTC ACGATCAGCAGCATGGAGGCTGAAGATGTTGCCACTTATTACT GTTTTCAGGCGAGTGGGTACCCGCTCACGTTCGGTGCTGGGAC CAAGCTGGAGCTGAAACGG |
| 3 | 1J1s VH amino acid sequence | QVQLKESGPGLVAPSQSLSITCTVSGFSLISYGVDWVRQPPGKGLE WLGVIWGGGNTNYNSSLMSRLSISKDNSKSQVFLKMNSLQTDDT AMYYCAKTGTGYALEYWGQGTSVTVSS |
| 4 | 1J1s VL amino acid sequence | ENVLTQSPAIMSASPGEKVTMTCSARSSVSYMHWYQQKSTASPK LWIYDTSKLASGVPGRFSGSGSGNSYSLTISSMEAEDVATYYCFQ ASGYPLTFGAGTKLELKR |
| 5 | 1J1s VL FW1 | ENVLTQSPAIIVISASPGEKVTMTC |
| 6 | 1J1s VL CDR1 | SARSSVSYMH |
| 7 | 1J1s VL FW2 | WYQQKSTASPKLWIY |
| 8 | 1J1s VL CDR2 | DTSKLAS |
| 9 | 1J1s VL FW3 | GVPGRFSGSGSGNSYSLTISSMEAEDVATYYC |
| 10 | 1J1s VL CDR3 | FQASGYPLT |
| 11 | 1J1s VL FW4 | FGAGTKLELKR |
| 12 | 1J1s VH FW1 | QVQLKESGPGLVAPSQSLSITCTVS |
| 13 | 1J1s VH CDR1 | GFSLISYGVD |
| 14 | 1J1s VH FW2 | WVRQPPGKGLEWLG |
| 15 | 1J1s VH CDR2 | VIWGGGNTNYNSSLMS |
| 16 | 1J1s VH FW3 | RLSISKDNSKSQVFLKMNSLQTDDTAMYYCAK |
| 17 | 1J1s VH CDR3 | TGTGYALEY |
| 18 | 1J1s VH FW4 | WGQGTSVTVSS |

The mAb 1G1s (ATCC Accession No. PTA-122678) is a mouse monoclonal antibody, produced by the hybridoma cell line (ATCC Accession No. PTA-122678). The antibodies described herein can contain the same VH and VL chains as antibody 1G1s. Antibodies binding to the same epitope as 1G1s are also within the scope of this disclosure.

Exemplars and their amino acid and nucleic acid structures/sequences are provided below:

TABLE 2

Amino Acid and Nucleotide Sequences of Antibody 1G1s

| SEQ ID NO | DESCRIPTION | SEQUENCE |
|---|---|---|
| 19 | 1G1s VH nucleotide sequence | CAGGTGCAGCTGAAGGAGTCAGGACCTGGCCTGGTGGCGCCCT CACAGAGCCTGTCCATCACTTGTACTGTCTCTGGGTTTTCATTA AGCAGCTATGGTGTAGACTGGGTTCGCCAACCTCCAGGAAAGG GTCTGGAGTGGCTGGGAGTAATATGGGGTGGTGGAAGCATAA ATTATAATTCAGCTCTCATGTCCAGACTGAGCATCAGCAAAGA CAATTCCAAGAGCCAAATTTTCTTAAAAATGAACAGTCTGCAA ACTGATGACACAGCCATATACTACTGTACCACACATGAGGATT ACGGTCCTTTTGCTTACTGGGGCCAAGGGACTCTGGTCACTGTC TCTGCA |

TABLE 2-continued

Amino Acid and Nucleotide Sequences of Antibody 1G1s

| SEQ ID NO | DESCRIPTION | SEQUENCE |
|---|---|---|
| 20 | 1G1s VL nucleotide sequence | CAAATTGTTCTCTCCCAGTCTCCAGCAATCCTGTCTGCATCTCC AGGGGAGAAGGTCACAATGACTTGCAGGGCCAGCTCAAGTGT AAGTTACATGCACTGGTACCAGCAGAAGCCAGGATCCTCCCCC AAATCCTGGATTTATGCCACATCCAACCTGGCTTCTGGAGTCCC TGCTCGCTTCAGTGGCAGTGGGTCTGGGACCTCTTACTCTCTCA CAATCAGCAGAGTGGAGGCTGAAGATGCTGCCACTTATTACTG CCAGCAGTGGGGTAGTTACCCGTGGACGTTCGGTGGAGGCACC AAGCTGGAAATCAAACGG |
| 21 | 1G1s VH amino acid sequence | QVQLKESGPGLVAPSQSLSITCTVSGFSLSSYGVDWVRQPPGKGL EWLGVIWGGGSINYNSALMSRLSISKDNSKQIFLKMNSLQTDDT AIYYCTTHEDYGPFAYWGQGTLVTVSA |
| 22 | 1G1s VL amino acid sequence | QIVLSQSPAILSASPGEKVTMTCRASSSVSYMHWYQQKPGSSPKS WIYATSNLASGVPARFSGSGSGTSYSLTISRVEAEDAATYYCQQW GSYPWTFGGGTKLEIKR |
| 23 | 1G1s VL FW1 | QIVLSQSPAILSASPGEKVTMTC |
| 24 | 1G1s VL CDR1 | RASSSVSYMH |
| 25 | 1G1s VL FW2 | WYQQKPGSSPKSWIY |
| 26 | 1G1s VL CDR2 | ATSNLAS |
| 27 | 1G1s VL FW3 | GVPARFSGSGSGTSYSLTISRVEAEDAATYYC |
| 28 | 1G1s VL CDR3 | QQWGSYPWT |
| 29 | 1G1s VL FW4 | FGGGTKLEIKR |
| 30 | 1G1s VH FW1 | QVQLKESGPGLVAPSQSLSITCTVS |
| 31 | 1G1s VH CDR1 | GFSLSSYGVD |
| 32 | 1G1s VH FW2 | WVRQPPGKGLEWLG |
| 33 | 1G1s VH CDR2 | VIWGGGSINYNSALMS |
| 34 | 1G1s VH FW3 | RLSISKDNSKQIFLKMNSLQTDDTAIYYCTT |
| 35 | 1G1s VH CDR3 | HEDYGPFAY |
| 36 | 1G1s VH FW4 | WGQGTLVTVSA |

The mAb 2F20s (ATCC Accession No. PTA-122676) is a monoclonal antibody, produced by the hybridoma cell line (ATCC Accession No. PTA-122676). The antibodies described herein can contain the same VH and VL chains as antibody 2F20s. Antibodies binding to the same epitope as 2F20s are also within the scope of this disclosure.

Exemplars and their amino acid and nucleic acid structures/sequences are provided below:

TABLE 3

Amino Acid and Nucleotide Sequences of Antibody 2F20s

| SEQ ID NO | DESCRIPTION | SEQUENCE |
|---|---|---|
| 37 | 2F20s VH nucleotide sequence | CAGGTGCAGCTGAAGGAGTCAGGACCTGGCCTGGTGGCGCCC TCACAGAGCCTGTCCATCACATGCACTGTCTCAGGGTTTTCAT TAACCAGTTATGGTGTAAGCTGGGCTCGCCAGCCTCCAGGAA AGGGTCTGGAGTGGCTGGGAGTAATATGGGGTGACGGGAGC ACAAATTATCATTCAGCTCTCATATCCAGACTGAGCATCAGC AAGGATAACTCCAAGAGCCAAGTTTTCTTAAAACTGAACAGT CTGCAAACTGATGACACAGCCACGTACTACTGTGCCAAACCG GAAAACTGGGACGGCTTCGATGTCTGGGGCCCAGGGACCACG GTCACCGTCTCCTCA |
| 38 | 2F20s VL nucleotide sequence | CAAATTGTTCTCTCCCAGTCTCCAGCAATCCTGTCTGCATCTC CAGGGGAGAAGGTCACAATGACTTGCAGGGCCAGCTCAAGT GTAAGTTACATGCACTGGTACCGACAGAAGCCAGGATCCTCC CCCAAACCCTGGATTTATGCCACATCCGACCTGGCTTCTGGA |

TABLE 3-continued

Amino Acid and Nucleotide Sequences of Antibody 2F20s

| SEQ ID NO | DESCRIPTION | SEQUENCE |
|---|---|---|
|  |  | GTCCCTACTCGCTTCAGTGGCAGTGGGTCTGGGACCTCTTACT CTCTCACAATCAGCAGAGTGGAGGCTGAAGATGCTGCCACTT ATTACTGCCAGCAGTGGAGTAGTTACCCGTGGACGTTCGGTG GAGGCACCAAGCTGGAAATCAAACGG |
| 39 | 2F20s VH amino acid sequence | QVQLKESGPGLVAPSQSLSITCTVSGFSLTSYGVSWARQPPGKGL EWLGVIWGDGSTNYHSALISRLSISKDNSKSQVFLKLNSLQTDD TATYYCAKPENWDGFDVWGPGTTVTVSS |
| 40 | 2F20s VL amino acid sequence | QIVLSQSPAILSASPGEKVTMTCRASSSVSYMEIWYRQKPGSSPKP WIYATSDLASGVPTRFSGSGSGTSYSLTISRVEAEDAATYYCQQ WSSYPWTFGGGTKLEIKR |
| 41 | 2F20s VL FW1 | QIVLSQSPAILSASPGEKVTMTC |
| 42 | 2F20s VL CDR1 | RASSSVSYMEI |
| 43 | 2F20s VL FW2 | WYRQKPGSSPKPWIY |
| 44 | 2F20s VL CDR2 | ATSDLAS |
| 45 | 2F20s VL FW3 | VPTRFSGSGSGTSYSLTISRVEAEDAATYYC |
| 46 | 2F20s VL CDR3 | QQWSSYPWT |
| 47 | 2F20s VL FW4 | FGGGTKLEIKR |
| 48 | 2F20s VH FW1 | QVQLKESGPGLVAPSQSLSITCTVS |
| 49 | 2F20s VH CDR1 | GFSLTSYGVS |
| 50 | 2F20s VH FW2 | WARQPPGKGLEWLG |
| 51 | 2F20s VH CDR2 | VIWGDGSTNYHSALIS |
| 52 | 2F20s VH FW3 | RLSISKDNSKSQVFLKLNSLQTDDTATYYCAK |
| 53 | 2F20s VH CDR3 | PENWDGFDV |
| 54 | 2F20s VH FW4 | WGPGTTVTVSS |

A "1J1s antibody" or "mAb 1J1s" or "antibody from clone 1J1s" refers to an antibody expressed by clone 1J1s or to an antibody synthesized in other manners, but having the same CDRs and optionally, the same framework regions as the antibody expressed by clone 1J1s.

One aspect of the present disclosure features the new antibodies specific to SSEA-4. The anti-SSEA-4 antibody binds to Neu5Acα2→3Galβ1→3GalNAcβ1→3Galα1→4Galβ1→4Glcβ1 (SSEA-4 hexasaccharide).

Any of the antibodies described herein can be a full length antibody or an antigen-binding fragment thereof. In some examples, the antigen binding fragment is a Fab fragment, a F(ab')$_2$ fragment, or a single-chain Fv fragment. In some examples, the antigen binding fragment is a Fab fragment, a F(ab')$_2$ fragment, or a single-chain Fv fragment. In some examples, the antibody is a human antibody, a humanized antibody, a chimeric antibody, or a single-chain antibody.

Any of the antibodies described herein has one or more characteristics of: (a) is a recombinant antibody, a monoclonal antibody, a chimeric antibody, a humanized antibody, a human antibody, an antibody fragment, a bispecific antibody, a monospecific antibody, a monovalent antibody, an IgG$_1$ antibody, an IgG$_2$ antibody, or derivative of an antibody; (b) is a human, murine, humanized, or chimeric antibody, antigen-binding fragment, or derivative of an antibody; (c) is a single-chain antibody fragment, a multibody, a Fab fragment, and/or an immunoglobulin of the IgG, IgM, IgA, IgE, IgD isotypes and/or subclasses thereof; (d) has one or more of the following characteristics: (i) mediates ADCC and/or CDC of cancer cells; (ii) induces and/or promotes apoptosis of cancer cells; (iii) inhibits proliferation of target cells of cancer cells; (iv) induces and/or promotes phagocytosis of cancer cells; and/or (v) induces and/or promotes the release of cytotoxic agents; (e) specifically binds the tumor-associated carbohydrate antigen, which is a tumor-specific carbohydrate antigen; (f) does not bind an antigen expressed on non-cancer cells, non-tumor cells, benign cancer cells and/or benign tumor cells; and/or (g) specifically binds a tumor-associated carbohydrate antigen expressed on cancer stem cells and on normal cancer cells.

Preferably the binding of the antibodies to their respective antigens is specific. The term "specific" is generally used to refer to the situation in which one member of a binding pair will not show any significant binding to molecules other than its specific binding partner (s) and e.g. has less than about 30%, preferably 20%, 10%, or 1% cross-reactivity with any other molecule other than those specified herein.

The antibodies are suitable bind to the target epitopes with a high affinity (low KD value), and preferably KD is in the nanomolar range or lower. Affinity can be measured by methods known in the art, such as, for example; surface plasmon resonance.

Exemplary Antibody Preparation

Exemplary Antibodies capable of binding to the Globo H epitopes and SSEA-4 epitopes described herein can be made by any method known in the art. See, for example, Harlow and Lane, (1988) Antibodies: A Laboratory Manual, Cold Spring Harbor Laboratory, New York.

Immunization of Host Animals and Hybridoma Technology

In one embodiment, the present invention provides for a method for making a hybridoma that expresses an antibody that specifically binds to a carbohydrate antigen (e.g., Globo H). The method contains the following steps: immunizing an animal with a composition that includes a carbohydrate antigen (e.g., Globo H); isolating splenocytes from the animal; generating hybridomas from the splenocytes; and selecting a hybridoma that produces an antibody that specifically binds to Globo H. Kohler and Milstein, Nature, 256: 495, 1975. Harlow, E. and Lane, D. Antibodies: A Laboratory Manual, Cold Spring Harbor Laboratory Press, Cold Spring Harbor, N.Y., 1988.

In one embodiment, carbohydrate antigen is used to immunize mice subcutaneously. One or more boosts may or may not be given. The titers of the antibodies in the plasma can be monitored by, e.g., ELISA (enzyme-linked immunosorbent assay) or flow cytometry. Mice with sufficient titers of anti-carbohydrate antigen antibodies are used for fusions. Mice may or may not be boosted with antigen 3 days before sacrifice and removal of the spleen. The mouse splenocytes are isolated and fused with PEG to a mouse myeloma cell line. The resulting hybridomas are then screened for the production of antigen-specific antibodies. Cells are plated, and then incubated in selective medium. Supernatants from individual wells are then screened by ELISA for human anti-carbohydrate antigen monoclonal antibodies. The antibody secreting hybridomas are repeated, screened again, and if still positive for anti-carbohydrate antigen antibodies, can be subcloned by limiting dilution.

Adjuvants that may be used to increase the immunogenicity of one or more of the carbohydrate antigens. Non-limiting examples of adjuvants include aluminum phosphate, aluminum hydroxide, MF59 (4.3% w/v squalene, 0.5% w/v polysorbate 80 (Tween 80), 0.5%>w/v sorbitan trioleate (Span 85)), CpG-containing nucleic acid, QS21 (saponin adjuvant), a-Galactosyl-ceramides or synthetic analogs thereof (e.g., C34, see U.S. Pat. No. 8,268,969), MPL (Monophosphoryl Lipid A), 3DMPL (3-O-deacylated MPL), extracts from Aquilla, ISCOMS (see, e.g., Sjolander et al. (1998) J. Leukocyte Biol. 64:713; WO90/03184; WO96/11711; WO 00/48630; WO98/36772; WO00/41720; WO06/134423 and WO07/026190), LT/CT mutants, poly (D,L-lactide-co-glycolide) (PLG) microparticles, Quil A, interleukins, Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(-2'-dip-almitoyl-sn-glycero-3-hydroxyphosphoryloxy)-ethylamine (CGP 19835 A, referred to as MTP-PE), and RIBI, which contains three components extracted from bacteria, monophosphoryl lipid A, trehalose dimycolate and cell wall skeleton (MPL+TDM+CWS) in a 2%>squalene/Tween 80 emulsion.

Exemplary Polyclonal antibodies against the anti-SSEA-4 antibodies may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum.

Polyclonal antibodies are generally raised in host animals (e.g., rabbit, mouse, horse, or goat) by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, etc.

Any mammalian animal may be immunized with the antigen for producing the desired antibodies. In general, animals of Rodentia, Lagomorpha, or Primates can be used. Animals of Rodentia include, for example, mouse, rat, and hamster. Animals of Lagomorpha include, for example, rabbit. Animals of Primates include, for example, a monkey of Catarrhini (old world monkey) such as *Macaca fascicularis*, rhesus monkey, baboon, and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Animals are immunized against the antigen, immunogenic conjugates, or derivatives by combining 1 mg or 1 μg of the peptide or conjugate (for rabbits or mice, respectively) with 3 volumes of Freund's incomplete adjuvant.

Animals can be boosted until the titer plateaus by several administrations of antigen mixed with an appropriately amount of Freund's incomplete adjuvant every 4 to 21 days. Animals are boosted with ⅕ to 1/10 the original amount of peptide or conjugate in Freund's complete adjuvant by subcutaneous injection at multiple sites. Seven to 14 days later the animals are bled and the serum is assayed for antibody titer. An appropriate carrier may also be used for immunization. After immunization as above, serum is examined by a standard method for an increase in the amount of desired antibodies. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Over the past two to three decades, a number of methodologies have been developed to prepare chimeric, humanized or human antibodies for human in-vivo therapeutic applications. The most used and proven methodology is to prepare mouse mAbs using hybridoma methodology and then to humanize the mAbs by converting the framework regions of the VH and VL domains and constant domains of the mAbs into most homologous human framework regions of human VH and VL domains and constant regions of a desirable human γ immunoglobulin isotype and subclass. Many mAbs, such as Xolair, used clinically are humanized mAbs of human γ1, κ isotype and subclass and prepared using this methodology.

In certain embodiments, antibodies can be made by the conventional hybridoma technology. Kohler et al., Nature, 256:495 (1975). In the hybridoma method, a mouse or other appropriate host animal, such as a hamster or rabbit, is immunized as hereinabove described to elicit lymphocytes that produce or are capable of producing antibodies that will specifically bind to the protein used for immunization. Alternatively, lymphocytes may be immunized in vitro.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

Preferred myeloma cells are those that fuse efficiently, support stable high-level production of antibody by the selected antibody-producing cells, and sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

The above immunocyte and myeloma cells can be fused according to known methods, for example, the method of Milstein et al. (Galfre et al., Methods Enzymol. 73:3-46, 1981). Lymphocytes are fused with myeloma cells using a suitable fusing agent, such as polyethylene glycol, to form a hybridoma cell (Goding, Monoclonal Antibodies: Principles and Practice, pp. 59-103 (Academic Press, 1986)). Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay. Measurement of absorbance in enzyme-linked immunosorbent assay (ELISA), enzyme immunoassay (EIA), radioimmunoassay (RIA), and/or immunofluorescence may be used to measure the antigen binding activity of the antibody of the invention. In ELISA, the antibody of the present invention is immobilized on a plate, protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of the protein, such as a C-terminal or N-terminal fragment may be used in this method. BIAcore (Pharmacia) may be used to evaluate the activity of the antibody according to the present invention. The binding affinity of the monoclonal antibody can, for example, be determined by the Scatchard analysis of Munson et al., Anal. Biochem., 107:220 (1980).

Applying any of the conventional methods, including those described above, hybridoma cells producing antibodies that bind to epitopes described herein can be identified and selected for further characterization.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In addition, the hybridoma cells may be grown in vivo as ascites tumors in an animal. For example, the obtained hybridomas can be subsequently transplanted into the abdominal cavity of a mouse and the ascites are harvested.

The obtained monoclonal antibodies can be purified by, for example, ammonium sulfate precipitation, a protein A or protein G column, DEAE ion exchange chromatography, or an affinity column to which the protein of the present invention is coupled. The antibody of the present invention can be used not only for purification and detection of the protein of the present invention, but also as a candidate for agonists and antagonists of the protein of the present invention. In addition, this antibody can be applied to the antibody treatment for diseases related to the protein of the present invention.

Recombinant Technology

The monoclonal antibodies thus obtained can be also recombinantly prepared using genetic engineering techniques (see, for example, Borrebaeck C. A. K. and Larrick J. W. Therapeutic Monoclonal Antibodies, published in the United Kingdom by MacMillan Publishers LTD, 1990). A DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

When the obtained antibody is to be administered to the human body (antibody treatment), a human antibody or a humanized antibody is preferable for reducing immunogenicity. For example, transgenic animals having a repertory of human antibody genes may be immunized with an antigen selected from a protein, protein expressing cells, or their lysates. Antibody producing cells are then collected from the animals and fused with myeloma cells to obtain hybridoma, from which human antibodies against the protein can be prepared. Alternatively, an immune cell, such as an immunized lymphocyte, producing antibodies may be immortalized by an oncogene and used for preparing monoclonal antibodies.

DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Rev., 130:151-188 (1992).

DNAs encoding the antibodies produced by the hybridoma cells described above can be genetically modified, via routine technology, to produce genetically engineered antibodies. Genetically engineered antibodies, such as humanized antibodies, chimeric antibodies, single-chain antibodies, and bi-specific antibodies, can be produced via, e.g., conventional recombinant technology. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad Sci. USA, 89:4285 (1992); Presta et al., J. Immnol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i. e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993). Human antibodies can also be derived from phage-display libraries (Hoogenboom et al., J. Mol. Biol., 227:381 (1991); Marks et al., J. Mol. Biol., 222:581-597 (1991)).

Any of the nucleic acid encoding the anti-SSEA-4 antibodies described herein (including heavy chain, light chain, or both), vectors such as expression vectors comprising one or more of the nucleic acids, and host cells comprising one or more of the vectors are also within the scope of the present disclosure. In some examples, a vector comprises a nucleic acid comprising a nucleotide sequence encoding either the heavy chain variable region or the light chain variable region of an anti-Globo H antibody as described herein. In some examples, a vector comprises a nucleic acid comprising a nucleotide sequence encoding either the heavy chain variable region or the light chain variable region of an anti-SSEA-4 antibody as described herein. In other examples, the vector comprises nucleotide sequences encoding both the heavy chain variable region and the light chain variable region, the expression of which can be controlled by a single promoter or two separate promoters. Also provided here are methods for producing any of the anti-Globo Hand anti-SSEA-4 antibodies as described herein, e.g., via the recombinant technology described herein.

Other Technology for Preparing Antibodies

In certain embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse® from Medarex, Inc. (Princeton, N.J.). Alternatively, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody, (i.e., full-length antibody), can be prepared via routine methods. For example, F(ab')$_2$ fragments can be produced by pepsin digestion of an antibody molecule, and Fab fragments that can be generated by reducing the disulfide bridges of F(ab')$_2$ fragments.

Alternatively, the anti-Globo H and anti-SSEA-4 antibodies described herein can be isolated from antibody phage libraries (e.g., single-chain antibody phage libraries) generated using the techniques described in McCafferty et al., Nature, 348:552-554 (1990). Clackson et al., Nature, 352: 624-628 (1991) and Marks et al., J. Mol Biol., 222:581-597 (1991). Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

Antibodies obtained as described herein may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory, 1988), but are not limited thereto. The concentration of the antibodies obtained as above may be determined by the measurement of absorbance, Enzyme-linked immunosorbent assay (ELISA), or so on. Exemplary chromatography, with the exception of affinity includes, for example, ion-exchange chromatography, hydrophobic chromatography, gel filtration, reverse-phase chromatography, adsorption chromatography, and so on (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography, such as HPLC or FPLC.

The antibodies can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In additional, epitope mapping can be used to determine the sequence to which an antibody binds. The epitope can be a linear epitope, (e.g., contained in a single stretch of amino acids), or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays.

In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various residues in the binding epitope for the candidate antibody have been replaced (swapped) with sequences from a closely related, but antigenically distinct protein (such as another member of the neurotrophin protein family). By assessing binding of the antibody to the mutant target protein, the importance of the particular antigen fragment to antibody binding can be assessed.

Alternatively, competition assays can be performed using other antibodies known to bind to the same antigen to determine whether an antibody binds to the same epitope (e.g., the MC45 antibody described herein) as the other antibodies. Competition assays are well known to those of skill in the art.

Additional Aspects of Exemplary Suitable General Antibody Production Methods

Methods of making monoclonal and polyclonal antibodies and fragments thereof in animals (e.g., mouse, rabbit, goat, sheep, or horse) are well known in the art. See, for example, Harlow and Lane, (1988) Antibodies: A Laboratory Manual, Cold Spring Harbor Laboratory, New York. The term "antibody" includes intact immunoglobulin molecules as well as fragments thereof, such as Fab, $F(ab)_2$, Fv, scFv (single chain antibody), and dAb (domain antibody; Ward, et. al. (1989) Nature, 341, 544).

The compositions disclosed herein can be included in a pharmaceutical composition together with additional active agents, carriers, vehicles, excipients, or auxiliary agents identifiable by a person skilled in the art upon reading of the present disclosure.

The pharmaceutical compositions preferably comprise at least one pharmaceutically acceptable carrier. In such pharmaceutical compositions, the compositions disclosed herein form the "active compound", also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (e.g., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Compositions comprising at least one anti-SSEA-4 antibody or at least one polynucleotide comprising sequences encoding an anti-SSEA-4 antibody are provided. In certain embodiments, a composition may be a pharmaceutical composition. As used herein, compositions comprise one or more antibodies that bind to one or more SSEA-4 and/or one or more polynucleotides comprising sequences encoding one or more antibodies that bind to one or more SSEA-4. These compositions may further comprise suitable carriers, such as pharmaceutically acceptable excipients including buffers, which are well known in the art.

In one embodiment, anti-SSEA-4 antibodies are monoclonal. In another embodiment, fragments of the anti-SSEA-4 antibodies (e.g., Fab, Fab'-SH and $F(ab')_2$ fragments) are provided. These antibody fragments can be created by traditional means, such as enzymatic digestion, or may be generated by recombinant techniques. Such antibody fragments may be chimeric, humanized, or human. These fragments are useful for the diagnostic and therapeutic purposes set forth below.

A variety of methods are known in the art for generating phage display libraries from which an antibody of interest can be obtained. One method of generating antibodies of interest is through the use of a phage antibody library as described in Lee et al., J. Mol. Biol. (2004), 340(5): 1073-93.

The anti-SSEA-4 antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-SSEA-4 antibodies of the invention can be obtained by designing a suitable antigen screening procedure to select for the phage clone of interest followed by construction of a full length anti-SSEA-4 antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597

(1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., Nucl. Acids Res., 19: 4133-4137 (1991).

In general, nucleic acids encoding antibody gene fragments are obtained from immune cells harvested from humans or animals. If a library biased in favor of anti-SSEA-4 clones is desired, the subject is immunized with SSEA-4 to generate an antibody response, and spleen cells and/or circulating B cells or other peripheral blood lymphocytes (PBLs) are recovered for library construction. In one embodiment, a human antibody gene fragment library biased in favor of anti-human SSEA-4 clones is obtained by generating an anti-human SSEA-4 antibody response in transgenic mice carrying a functional human immunoglobulin gene array (and lacking a functional endogenous antibody production system) such that SSEA-4 immunization gives rise to B cells producing human antibodies against SSEA-4. The generation of human antibody-producing transgenic mice is described below.

Additional enrichment for anti-SSEA-4 reactive cell populations can be obtained by using a suitable screening procedure to isolate B cells expressing SSEA-4-specific antibody, e.g., by cell separation with SSEA-4 affinity chromatography or adsorption of cells to fluorochrome-labeled/SSEA-4/followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which SSEA-4 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., Proc. Natl. Acad. Sci. (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., Nature, 341: 544-546 (1989). However, for amplifying from cDNA, back primers can also be based in the leader exon as described in Jones et al., Biotechnol., 9: 88-89 (1991), and forward primers within the constant region as described in Sastry et al., Proc. Natl. Acad. Sci. (USA), 86: 5728-5732 (1989). To maximize complementarity, degeneracy can be incorporated in the primers as described in Orlandi et al. (1989) or Sastry et al. (1989). In certain embodiments, the library diversity is maximized by using PCR primers targeted to each V-gene family in order to amplify all available VH and VL arrangements present in the immune cell nucleic acid sample, e.g. as described in the method of Marks et al., J. Mol. Biol., 222: 581-597 (1991) or as described in the method of Orum et al., Nucleic Acids Res., 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., Nature, 352: 624-628 (1991).

Repertoires of synthetically rearranged V genes can be derived in vitro from V gene segments. Most of the human VH-gene segments have been cloned and sequenced (reported in Tomlinson et al., J. Mol. Biol., 227: 776-798 (1992)), and mapped (reported in Matsuda et al., Nature Genet., 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., Proc. Natl. Acad. Sci. USA, 89: 4457-4461 (1992). Human Vκ and Vλ, segments have been cloned and sequenced (reported in Williams and Winter, Eur. J. Immunol., 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, J. Mol. Biol., 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., Gene, 128: 119-126 (1993), or in vivo by combinatorial infection, e.g., the loxP system described in Waterhouse et al., Nucl. Acids Res., 21: 2265-2266 (1993). The in vivo recombination approach exploits the two-chain nature of Fab fragments to overcome the limit on library size imposed by E. coli transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about 1012 clones). Both vectors contain in vivo recombination signals so that the VH and VL genes are recombined onto a single replicon and are co-packaged into phage virions. These huge libraries provide large numbers of diverse antibodies of good affinity.

Alternatively, the repertoires may be cloned sequentially into the same vector, e.g., as described in Barbas et al., Proc. Natl. Acad. Sci. USA, 88: 7978-7982 (1991), or assembled together by PCR and then cloned, e.g. as described in Clackson et al., Nature, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., Nucl. Acids Res., 20: 3831-3837 (1992).

Screening of the libraries can be accomplished by any art-known technique. For example, SSEA-4 targets can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized SSEA-4 under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., Proc. Natl. Acad. Sci. USA, 88: 7978-7982 (1991), or by alkali, e.g. as described in Marks et al., J. Mol. Biol., 222: 581-597 (1991), or by SSEA-43/antigen competition, e.g. in a procedure similar to the antigen competition method of Clackson et al., Nature, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

It is possible to select between phage antibodies of different affinities, even with affinities that differ slightly, for SSEA-4. However, random mutation of a selected antibody (e.g. as performed in some of the affinity maturation techniques described above) is likely to give rise to many mutants, most binding to antigen, and a few with higher affinity. With limiting SSEA-4, rare high affinity phage could be competed out. To retain all the higher affinity mutants, phages can be incubated with excess biotinylated SSEA-4, but with the biotinylated SSEA-4 at a concentration of lower molarity than the target molar affinity constant for SSEA-4. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-SSEA-4 clones may be selected. In one embodiment, the invention provides anti-SSEA-4 antibodies that block the binding between a SSEA-4 ligand and SSEA-4, but do not block the binding between a SSEA-4 ligand and a second protein. Fv clones corresponding to such anti-SSEA-4 antibodies can be selected by (1) isolating anti-SSEA-4 clones from a phage library as described in Section B(I)(2) above, and optionally amplifying the isolated population of phage clones by growing up the population in a suitable bacterial host; (2) selecting SSEA-4 and a second protein against which blocking and non-blocking activity, respectively, is desired; (3) adsorbing the anti-SSEA-4 phage clones to immobilized SSEA-4; (4) using an excess of the second protein to elute any undesired clones that recognize SSEA-4-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., Curr. Opinion in Immunol., 5: 256 (1993) and Pluckthun, Immunol. Revs, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In one embodiment, a Fv clone derived from human variable DNA is fused to human constant region DNA to form coding sequence(s) for all human, full or partial length heavy and/or light chains.

The antibodies produced by naive libraries (either natural or synthetic) can be of moderate affinity, but affinity maturation can also be mimicked in vitro by constructing and reselecting from secondary libraries as described in Winter et al. (1994), supra. In some aspects the antibodies may exclude naturally occurring antibody sequences. In some aspects, mutation can be introduced at random in vitro by using error-prone polymerase (reported in Leung et al., Technique, 1: 11-15 (1989)) in the method of Hawkins et al., J. Mol. Biol., 226: 889-896 (1992) or in the method of Gram et al., Proc. Natl. Acad. Sci. USA, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., Biotechnol., 10: 779-783 (1992). This technique allows the production of antibodies and antibody fragments with affinities in the $10^{-9}$ M range. Other Methods of Generating Anti-SSEA-4 Antibodies.

Other methods of generating and assessing the affinity of antibodies are well known in the art and are described, e.g., in Kohler et al., Nature 256: 495 (1975); U.S. Pat. No. 4,816,567; Goding, Monoclonal Antibodies: Principles and Practice, pp. 59-103 (Academic Press, 1986; Kozbor, J. Immunol., 133:3001 (1984); Brodeur et al., Monoclonal Antibody Production Techniques and Applications, pp. 51-63 (Marcel Dekker, Inc., New York, 1987; Munson et al., Anal. Biochem., 107:220 (1980); Engels et al., Agnew. Chem. Int. Ed. Engl., 28: 716-734 (1989); Abrahmsen et al., EMBO J., 4: 3901 (1985); Methods in Enzymology, vol. 44 (1976); Morrison et al., Proc. Natl. Acad. Sci. USA, 81: 6851-6855 (1984).

General Methods

In general, the invention provides affinity-matured SSEA-4 antibodies. These antibodies have increased affinity and specificity for SSEA-4. This increase in affinity and sensitivity permits the molecules of the invention to be used for applications and methods that are benefited by (a) the increased sensitivity of the molecules of the invention and/or (b) the tight binding of SSEA-4 by the molecules of the invention.

In one embodiment, SSEA-4 antibodies that are useful for treatment of SSEA-4-mediated disorders in which a partial or total blockade of one or more SSEA-4 activities is desired. In one embodiment, the anti SSEA-4 antibodies of the invention are used to treat cancer.

The anti-SSEA-4 antibodies of the invention permit the sensitive and specific detection of the epitopes in straightforward and routine biomolecular assays such as immunoprecipitations, ELISAs, or immunomicroscopy without the need for mass spectrometry or genetic manipulation. In turn, this provides a significant advantage in both observing and elucidating the normal functioning of these pathways and in detecting when the pathways are functioning aberrantly.

The SSEA-4 antibodies of the invention can also be used to determine the role in the development and pathogenesis of disease. For example, as described above, the SSEA-4 antibodies of the invention can be used to determine whether the TACAs are normally temporally expressed which can be correlated with one or more disease states.

The SSEA-4 antibodies of the invention can further be used to treat diseases in which one or more SSEA-4s are aberrantly regulated or aberrantly functioning without interfering with the normal activity of SSEA-4s for which the anti-SSEA-4 antibodies of the invention are not specific.

In another aspect, the anti-SSEA-4 antibodies of the invention find utility as reagents for detection of cancer states in various cell types and tissues.

In yet another aspect, the present anti-SSEA-4 antibodies are useful for the development of SSEA-4 antagonists with blocking activity patterns similar to those of the subject antibodies of the invention. For example, anti-SSEA-4 antibodies of the invention can be used to determine and identify other antibodies that have the same SSEA-4 binding characteristics and/or capabilities of blocking SSEA-4 pathways.

As a further example, anti-SSEA-4 antibodies of the invention can be used to identify other anti-SSEA-4 antibodies that bind substantially the same antigenic determinant(s) of SSEA-4 as the antibodies exemplified herein, including linear and conformational epitopes.

The anti-SSEA-4 antibodies of the invention can be used in assays based on the physiological pathways in which SSEA-4 is involved to screen for small molecule antagonists of SSEA-4 which will exhibit similar pharmacological effects in blocking the binding of one or more binding partners to SSEA-4 as the antibody does.

Generation of antibodies can be achieved using routine skills in the art, including those described herein, such as the hybridoma technique and screening of phage displayed libraries of binder molecules. These methods are well-established in the art.

Briefly, the anti-SSEA-4 antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-SSEA-4 antibodies of the invention can be obtained by designing a suitable antigen screening procedure to select for the phage clone of interest followed by construction of a full length anti-SSEA-4 antibody clone using the Fv sequences from the phage clone of interest and suitable constant region (Fc) sequences described in Kabat et al., Sequences of Proteins of Immunological Interest, Fifth Edition, NIH Publication 91-3242, Bethesda Md. (1991), vols. 1-3.

In one embodiment, anti-SSEA-4 antibodies of the invention are monoclonal. Also encompassed within the scope of the invention are antibody fragments such as Fab, Fab', Fab'-SH and F(ab')$_2$ fragments, and variations thereof, of the anti-SSEA-4 antibodies provided herein. These antibody fragments can be created by traditional means, such as enzymatic digestion, or may be generated by recombinant techniques. Such antibody fragments may be chimeric, human or humanized. These fragments are useful for the experimental, diagnostic, and therapeutic purposes set forth herein.

Monoclonal antibodies can be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-SSEA-4 monoclonal antibodies of the invention can be made using a variety of methods known in the art, including the hybridoma method first described by Kohler et al., Nature, 256:495 (1975), or alternatively they may be made by recombinant DNA methods (e.g., U.S. Pat. No. 4,816,567).

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Host cells include, but are not limited to, cells of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells
Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In certain embodiments, heterologous promoters are utilized, as they generally permit greater transcription and higher yields of expressed target gene as compared to the native target polypeptide promoter.

Promoters suitable for use with prokaryotic hosts include the PhoA promoter, the tion and higher yields of expressed target gene as compared to the native target polypeptide promoter. in by removing the promoter from the source DNA via restriction enzyme ditional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

The production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 hmann, Cellular and Molecular Biology, vol. 2 (Washington, D.C.: American Society for Microbiology, 1987), pp. 1190-1219; ATCC Deposit N *E. coli* 294 (ATCC 31,446), *E. coli* B, *E. coli E. coli* CC 31,446), enod *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In certain embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, growth occurs at a temperature range including, but not limited to, about 20° C. to about 39° C., about 25° C. to about 37° C., and at about 30° C. The pH of the medium may be any pH ranging from about 5 to about 9, depending mainly on the host organism. For *E. coli*, the pH can be from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In one embodiment, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, for example about 1,000 to 100,000 liters of capacity. These fermentors use agitator impellers to distribute oxygen and nutrients, especially glucose (a common carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been growing under suitable conditions to a desired density at which stage the cells are in the early stationary phase (e.g., an OD550 of about 180-220). A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis, trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureus* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, the preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected generally is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II (e.g., primate metallothionein genes), adenosine deaminase, ornithine decarboxylase, etc.

For example, cells transformed with the DHFR selection gene may first be identified by culturing all of the transformants in a culture medium that contains methotrexate (Mtx), a competitive antagonist of DHFR. Appropriate host cells when wild-type DHFR is employed include, for example, the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to nucleic acid encoding a polypeptide of interest (e.g., an antibody). Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding an antibody polypeptide of the invention by higher eukaryotes can often be increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is generally located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), (Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are generally removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a generally acceptable purification technique. The suitability of affinity reagents such as protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification steps, as necessary, for example by low pH hydrophobic interaction chromatography using an elution buffer at a pH between about 2.5-4.5, generally performed at low salt concentrations (e.g., from about 0-0.25M salt).

It should be noted that, in general, techniques and methodologies for preparing antibodies for use in research, testing and clinical use are well-established in the art, consistent with the above and/or as deemed appropriate by one skilled in the art for the particular antibody of interest.

Activity Assays

Antibodies of the invention can be characterized for their physical/chemical properties and biological functions by various assays known in the art.

Antibodies, or antigen-binding fragments, variants or derivatives thereof of the present disclosure can also be described or specified in terms of their binding affinity to an antigen. The affinity of an antibody for a carbohydrate antigen can be determined experimentally using any suitable method (see, e.g., Berzofsky et al, "Antibody—Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-carbohydrate antigen interaction can vary if measured under different conditions {e.g., salt concentration, pH). Thus, measurements of affinity and other antigen-binding parameters (e.g., $K_D$, $K_a$, Ka) are preferably made with standardized solutions of antibody and antigen, and a standardized buffer.

The present antibodies or antigen-binding portions thereof have in vitro and in vivo therapeutic, prophylactic, and/or diagnostic utilities. For example, these antibodies can be administered to cells in culture, e.g., in vitro or ex vivo, or to a subject, e.g., in vivo, to treat, inhibit, prevent relapse, and/or diagnose cancer.

Purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

Where necessary, antibodies are analyzed for their biological activity. In certain embodiments, antibodies of the invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, chemiluminescent immunoassays, nanoparticle immunoassays, aptamer immunoassays, and protein A immunoassays.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10: 163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is generally further desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-SSEA-4 antibodies of the invention can be constructed by combining Fv clone variable domain sequence(s) selected from human-derived phage display libraries with known human constant domain sequences(s) as described above. Alternatively, human monoclonal anti-SSEA-4 antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for SSEA-4 including a specific lysine linkage and the other is for any other antigen. In certain embodiments, bispecific antibodies may bind to two different SSEA-4s having two different lysine linkages. Bispecific antibodies can be prepared as full length antibodies or antibody fragments (e.g., $F(ab')_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., EMBO J., 10: 3655 (1991).

According to a different embodiment, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The dimerization domain comprises (or consists of), for example, an Fc region or a hinge region. In this scenario, the antibody will comprise an Fc region and three or more antigen binding sites amino-terminal to the Fc region. In one embodiment, a multivalent antibody comprises (or consists of), for example, three to about eight, or four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In certain embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FrameWork alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H).

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity) as herein disclosed. In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody. In some aspects the nucleic acid molecules will exclude naturally occurring sequences.

It may be desirable to introduce one or more amino acid modifications in an Fc region of antibodies of the invention, thereby generating an Fc region variant. The Fc region variant may comprise a human Fc region sequence (e.g., a human IgG$_1$, IgG$_2$, IgG$_3$ or IgG$_4$ Fc region) comprising an amino acid modification (e.g. a substitution) at one or more amino acid positions including that of a hinge cysteine.

Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Antibody Derivatives

Antibodies of the invention can be further modified to contain additional nonproteinaceous moieties that are known in the art and readily available. In one embodiment, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, the polymers can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Pharmaceutical Formulations

In one embodiment, the present invention provides pharmaceutical compositions comprising an antibody or antigen-binding portion thereof described herein, and a pharmaceutically acceptable carrier. In another embodiment, the pharmaceutical composition comprises a nucleic acid encoding the present antibody or antigen-binding portion thereof, and a pharmaceutically acceptable carrier. Pharmaceutically acceptable carriers include any and all solvents, dispersion media, isotonic and absorption delaying agents, and the like that are physiologically compatible. In one embodiment, the composition is effective to inhibit cancer cells in a subject.

Routes of administration of the present pharmaceutical compositions include, but are not limited to, intravenous, intramuscular, intransal, subcutaneous, oral, topical, subcutaneous, intradermal, transdermal, subdermal, parenteral, rectal, spinal, or epidermal administration.

The pharmaceutical compositions of the present invention can be prepared as injectables, either as liquid solutions or suspensions, or as solid forms which are suitable for solution or suspension in liquid vehicles prior to injection. The pharmaceutical composition can also be prepared in solid form, emulsified or the active ingredient encapsulated in liposome vehicles or other particulate carriers used for sustained delivery. For example, the pharmaceutical composition can be in the form of an oil emulsion, water-in-oil emulsion, water-in-oil-in-water emulsion, site-specific emulsion, long-residence emulsion, stickyemulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the pharmaceutical composition.

The present antibodies or antigen-binding portions thereof are formulated into pharmaceutical compositions for delivery to a mammalian subject. The pharmaceutical composition is administered alone, and/or mixed with a pharmaceutically acceptable vehicle, excipient or carrier. Suitable vehicles are, for example, water, saline, dextrose, glycerol, ethanol, or the like, and combinations thereof. In addition, the vehicle can contain minor amounts of auxiliary substances such as wetting or emulsifying agents, pH buffering agents, or adjuvants. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, detergents, liposomal carriers, or excipients or other stabilizers and/or buffers. Other physiologically acceptable compounds include wetting agents, emulsifying agents, dispersing agents or preservatives. See, for example, the 21$^{st}$ edition of Remington's Pharmaceutical Science, Mack Publishing Company, Easton, Pa. ("Remington's"). The pharmaceutical compositions of the present invention can also include ancillary substances, such as pharmacological agents, cytokines, or other biological response modifiers.

Furthermore, the pharmaceutical compositions can be formulated into pharmaceutical compositions in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Actual methods of preparing such dosage forms are known, or will be apparent, to those skilled in the art. See, for example, Remington's Pharmaceutical Sciences, Mack Publishing Company, Easton, Pa., 21$^{st}$ edition.

Pharmaceutical compositions can be administered in a single dose treatment or in multiple dose treatments on a schedule and over a time period appropriate to the age, weight, and condition of the subject, the particular composition used, and the route of administration, whether the pharmaceutical composition is used for prophylactic or curative purposes, etc. For example, in one embodiment, the pharmaceutical composition according to the invention is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an antibody according to the invention, i.e., the period of time over which the pharmaceutical composition is administered, can vary, depending on any of a variety of factors, e.g., subject response, etc. For example, the pharmaceutical composition can be administered over a period of time ranging from about one or more seconds to one or more hours, one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

For ease of administration and uniformity of dosage, oral or parenteral pharmaceutical compositions in dosage unit form may be used. Dosage unit form as used herein refers to physically discrete units suited as unitary dosages for the subject to be treated; each unit containing a predetermined quantity of active compound calculated to produce the desired therapeutic effect in association with the required pharmaceutical carrier.

The data obtained from the cell culture assays and animal studies can be used in formulating a range of dosage for use in humans. In one embodiment, the dosage of such compounds lies within a range of circulating concentrations that include the ED50 with little or no toxicity. The dosage can vary within this range depending upon the dosage form employed and the route of administration utilized. In another embodiment, the therapeutically effective dose can be estimated initially from cell culture assays. A dose can be formulated in animal models to achieve a circulating plasma concentration range that includes the IC$_{50}$ (i.e., the concentration of the test compound which achieves a half-maximal inhibition of symptoms) as determined in cell culture. Sonderstrup, Springer, Sem. Immunopathol. 25: 35-45, 2003. Nikula et al., Inhal. Toxicol. 4(12): 123-53, 2000.

An exemplary, non-limiting range for a therapeutically or prophylactically effective amount of an antibody or antigen-binding portion of the invention is from about 0.001 to about 60 mg/kg body weight, about 0.01 to about 30 mg/kg body weight, about 0.01 to about 25 mg/kg body weight, about 0.5 to about 25 mg/kg body weight, about 0.1 to about 20 mg/kg body weight, about 10 to about 20 mg/kg body weight, about 0.75 to about 10 mg/kg body weight, about 1 to about 10 mg/kg body weight, about 2 to about 9 mg/kg body weight, about 1 to about 2 mg/kg body weight, about 3 to about 8 mg/kg body weight, about 4 to about 7 mg/kg body weight, about 5 to about 6 mg/kg body weight, about 8 to about 13 mg/kg body weight, about 8.3 to about 12.5 mg/kg body weight, about 4 to about 6 mg/kg body weight, about 4.2 to about 6.3 mg/kg body weight, about 1.6 to about 2.5 mg/kg body weight, about 2 to about 3 mg/kg body weight, or about 10 mg/kg body weight.

The pharmaceutical composition is formulated to contain an effective amount of the present antibody or antigen-binding portion thereof, wherein the amount depends on the animal to be treated and the condition to be treated. In one embodiment, the present antibody or antigen-binding portion thereof is administered at a dose ranging from about 0.01 mg to about 10 g, from about 0.1 mg to about 9 g, from about 1 mg to about 8 g, from about 2 mg to about 7 g, from about 3 mg to about 6 g, from about 10 mg to about 5 g, from about 20 mg to about 1 g, from about 50 mg to about 800 mg, from about 100 mg to about 500 mg, from about 0.01 µg to about 10 g, from about 0.05 µg to about 1.5 mg, from about 10 µg to about 1 mg protein, from about 30 µg to about 500 from about 40 µg to about 300 from about 0.1 µg to about 200 from about 0.1 µg to about 5 from about 5 µg to about 10 from about 10 µg to about 25 µg, from about 25 µg to about 50 µg, from about 50 µg to about 100 µg, from about 100 µg to about 500 µg, from about 500 µg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy and can be determined by one of ordinary skill in the art without undue experimentation.

Therapeutic formulations comprising an antibody of the invention are prepared for storage by mixing the antibody having the desired degree of purity with optional physiologically acceptable carriers, excipients or stabilizers (Remington's Pharmaceutical Sciences 16$^{th}$ edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (e.g., octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, including, but not limited to those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the invention may be used in, for example, in vitro, ex vivo, and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, an antibody of the invention can be used for inhibiting antigen activities by contacting the antibody with the antigen such that antigen activity is inhibited. In one embodiment, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. In one embodiment, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Antibodies of the invention can be used to treat, inhibit, delay progression of, prevent/delay recurrence of, ameliorate, or prevent diseases, disorders or conditions associated with abnormal expression and/or activity of SSEA-4s and SSEA-4ated proteins, including but not limited to cancer, muscular disorders, ubiquitin-pathway-related genetic disorders, immune/inflammatory disorders, neurological disorders, and other ubiquitin pathway-related disorders.

In one aspect, a blocking antibody of the invention is specific for SSEA-4.

In certain embodiments, an immunoconjugate comprising an antibody of the invention conjugated with a cytotoxic agent is administered to the patient. In certain embodiments, the immunoconjugate and/or antigen to which it is bound is/are internalized by cells expressing one or more antigens on their cell surface which are associated with SSEA-4, resulting in increased therapeutic efficacy of the immunoconjugate in killing the target cell with which it is associated. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, and/or adjuvant/therapeutic agents (e.g., steroids). For instance, an antibody of the invention may be combined with an anti-inflammatory and/or antiseptic in a treatment scheme, e.g. in treating any of the diseases described herein, including cancer, muscular disorders, ubiquitin-pathway-related genetic disorders, immune/inflammatory disorders, neurological disorders, and other ubiquitin pathway-related disorders. Such combined therapies noted above include combined administration (where the two or more agents are included in the same or separate formulations), and separate administration, in which case, administration of the antibody of the invention can occur prior to, and/or following, administration of the adjunct therapy or therapies.

An antibody of the invention (and adjunct therapeutic agent) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, for example, by injections (e.g., intravenous or subcutaneous injections), depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. Intracellular expression of an intrabody is effected by introducing a nucleic acid encoding the desired antibody or antigen-binding portion thereof (lacking the wild-type leader sequence and secretory signals normally associated with the gene encoding the antibody or antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest. One or more nucleic acids encoding all or a portion of an anti-SSEA-4 antibody of the invention can be delivered to a target cell, such that one or more intrabodies are expressed which are capable of intracellular binding to a SSEA-4 and modulation of one or more SSEA-4-mediated cellular pathways.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889-7893 (1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes. See, e.g., Chen et al., Proc. Natl. Acad. Sci. USA (1999), 96:4325-4329.

When the binding target is located in the brain, certain embodiments of the invention provide for the antibody or antigen-binding fragment thereof to traverse the blood-brain barrier. Certain neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)), interstitial infusion/convection-enhanced delivery (see, e.g., Bobo et al., Proc. Natl. Acad. Sci. USA 91: 2076-2080 (1994)), and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Patent Application Publication No. 20020025313), and coating the antibody or antigen-binding fragment in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

The antibody composition of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg for the prevention or treatment of disease, the appropriate dosage of an antibody of the invention (with several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments, the subject being treated is a mammal. In certain embodiments, the subject is a human. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent, dog, or non-human primate. In certain embodiments, the subject is a non-human transgenic animal such as a transgenic mouse or transgenic pig.

Pharmaceutical Compositions and Formulations

After preparation of the antibodies as described herein, "pre-lyophilized formulation" can be produced. The antibody for preparing the formulation is preferably essentially pure and desirably essentially homogeneous (i.e. free from contaminating proteins etc.). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition. In certain embodiments, the protein is an antibody.

The amount of antibody in the pre-lyophilized formulation is determined taking into account the desired dose volumes, mode(s) of administration etc. Where the protein of choice is an intact antibody (a full-length antibody), from about 2 mg/mL to about 50 mg/mL, preferably from about 5 mg/mL to about 40 mg/mL and most preferably from about 20-30 mg/mL is an exemplary starting protein concentration. The protein is generally present in solution. For example, the protein may be present in a pH-buffered solution at a pH from about 4-8, and preferably from about 5-7. Exemplary buffers include histidine, phosphate, Tris, citrate, succinate and other organic acids. The buffer concentration can be from about 1 mM to about 20 mM, or from about 3 mM to about 15 mM, depending, for example, on the buffer and the desired isotonicity of the formulation (e.g. of the reconstituted formulation). The preferred buffer is histidine in that, as demonstrated below, this can have lyoprotective properties. Succinate was shown to be another useful buffer.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the protein occurs upon lyophilization. Where the lyoprotectant is a sugar (such as sucrose or trehalose) and the protein is an antibody, exemplary lyoprotectant concentrations in the pre-lyophilized formulation are from about 10 mM to about 400 mM, and preferably from about 30 mM to about 300 mM, and most preferably from about 50 mM to about 100 mM.

The ratio of protein to lyoprotectant is selected for each protein and lyoprotectant combination. In the case of an antibody as the protein of choice and a sugar (e.g., sucrose or trehalose) as the lyoprotectant for generating an isotonic reconstituted formulation with a high protein concentration, the molar ratio of lyoprotectant to antibody may be from about 100 to about 1500 moles lyoprotectant to 1 mole antibody, and preferably from about 200 to about 1000 moles of lyoprotectant to 1 mole antibody, for example from about 200 to about 600 moles of lyoprotectant to 1 mole antibody.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g. Pluronics, PF68 etc). The amount of surfactant added is such that it reduces aggregation of the reconstituted protein and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e.g. mannitol or glycine) is used in the preparation of the pre-lyophilization formulation. The bulking agent may allow for the production of a uniform lyophilized cake without excessive pockets therein etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include; additional buffering agents; preservatives; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions and formulations described herein are preferably stable. A "stable" formulation/composition is one in which the antibody therein essentially retains its physical and chemical stability and integrity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for protein, at about 120° C. for about 30 minutes, for example.

After the protein, lyoprotectant and other optional components are mixed together, the formulation is lyophilized. Many different freeze-dryers are available for this purpose such as Hull50® (Hull, USA) or GT20® (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g. 40-60 hrs). A secondary drying stage may be carried out at about 0-40° C., depending primarily on the type and size of container and the type of protein employed. However, it was found herein that a secondary drying step may not be necessary. For example, the shelf temperature throughout the entire water removal phase of lyophilization may be from about 15-30° C. (e.g., about 20° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g. 10-15 hours). The pressure may be the same as that employed during the primary drying step. Freeze-drying conditions can be varied depending on the formulation and vial size.

In some instances, it may be desirable to lyophilize the protein formulation in the container in which reconstitution of the protein is to be carried out in order to avoid a transfer step. The container in this instance may, for example, be a 3, 5, 10, 20, 50 or 100 cc vial. As a general proposition, lyophilization will result in a lyophilized formulation in which the moisture content thereof is less than about 5%, and preferably less than about 3%.

At the desired stage, typically when it is time to administer the protein to the patient, the lyophilized formulation may be reconstituted with a diluent such that the protein concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high protein concentrations in the reconstituted formulation are considered to be particularly useful where subcutaneous delivery of the reconstituted formulation is intended. However, for other routes of administration, such as intravenous administration, lower concentrations of the protein in the reconstituted formulation may be desired (for example from about 5-50 mg/mL, or from about 10-40 mg/mL protein in the reconstituted formulation). In certain embodiments, the protein concentration in the reconstituted formulation is significantly higher than that in the pre-lyophilized formulation. For example, the protein concentration in the reconstituted formulation may be about 2-40 times, preferably 3-10 times and most preferably 3-6 times (e.g. at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and protein. Exemplary diluents include sterile water, bacteriostatic water for injection (BWFI), a pH buffered solution (e.g. phosphate-buffered saline), sterile saline solution, Ringer's solution or dextrose solution. The diluent optionally contains a preservative. Exemplary preservatives have been described above, with aromatic alcohols such as benzyl or phenol alcohol being the preferred preservatives. The amount of preservative employed is determined by assessing different preservative concentrations for compatibility with the protein and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%. Preferably, the reconstituted formulation has less than 6000 particles per vial which are >10 μm size.

Therapeutic Applications

Described herein are therapeutic methods that include administering to a subject in need of such treatment a therapeutically effective amount of a composition that includes one or more antibodies described herein.

In certain embodiments, the subject (e.g., a human patient) in need of the treatment is diagnosed with, suspected of having, or at risk for cancer. Examples of the cancer include, but are not limited to, sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. In certain embodiments, the cancer is sarcoma, skin cancer, leukemia, lymphoma, brain cancer, lung cancer, breast cancer, ovarian cancer, prostate cancer, colon cancer, or pancreas cancer. In some preferred embodiments, the cancer is brain cancer or glioblastoma multiforme (GBM) cancer.

In preferred embodiments, the antibody is capable of targeting SSEA-4-expressing cancer cells. In certain embodiments, the antibody is capable of targeting SSEA-4 on cancer cells. In certain embodiments, the antibody is capable of targeting SSEA-4 in cancers.

The treatment results in reduction of tumor size, elimination of malignant cells, prevention of metastasis, prevention of relapse, reduction or killing of disseminated cancer, prolongation of survival and/or prolongation of time to tumor cancer progression.

In certain embodiments, the treatment further comprises administering an additional therapy to said subject prior to, during or subsequent to said administering of the antibodies. In certain embodiments, the additional therapy is treatment with a chemotherapeutic agent. In certain embodiments, the additional therapy is radiation therapy.

The methods of the invention are particularly advantageous in treating and preventing early stage tumors, thereby preventing progression to the more advanced stages resulting in a reduction in the morbidity and mortality associated with advanced cancer. The methods of the invention are also advantageous in preventing the recurrence of a tumor or the regrowth of a tumor, for example, a dormant tumor that persists after removal of the primary tumor, or in reducing or preventing the occurrence of a tumor.

In certain embodiments, the methods as disclosed herein are useful for the treatment or prevention of a cancer, for example where a cancer is characterized by increased Globo H, SSEA-3 and/or SSEA-4 expression. In certain embodiments the cancer comprises a cancer stem cell. In certain embodiments, the cancer is a pre-cancer, and/or a malignant cancer and/or a therapy resistant cancer. In certain embodiments, the cancer is a brain cancer.

For the methods of the invention, the cancer may be a liquid tumor, e.g., such as leukemia and lymphoma, solid tumor, for example, breast cancer, colorectal cancer, rectal cancer, lung cancer, renal cell cancer, a glioma (e.g., anaplastic astrocytoma, anaplastic oligoastrocytoma, anaplastic oligodendroglioma, glioblastoma multiforme (GBM)), kidney cancer, prostate cancer, liver cancer, pancreatic cancer, soft-tissue sarcoma, carcinoid carcinoma, head and neck cancer, melanoma, and ovarian cancer. In one embodiment, the cancer is a brain cancer or GBM. To practice the method disclosed herein, an effective amount of the pharmaceutical composition/formulation described above, containing at least one antibody described herein, can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having cancer, which include, but not limited to, breast cancer, lung cancer, esophageal cancer, rectal cancer, biliary cancer, liver cancer, buccal cancer, gastric cancer, colon cancer, nasopharyngeal cancer, kidney cancer, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer, basal cell carcinoma, squamous cell carcinoma, melanoma, or brain tumor. A subject having cancer can be identified by routine medical examination.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy, if any, the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of cancer. Alternatively, sustained continuous release formulations of the antibodies described herein may be appropriate. Various formulations and devices for achieving sustained release are known in the art.

In one example, dosages for an antibody as described herein may be determined empirically in individuals who have been given one or more administration(s) of the antibody. Individuals are given incremental dosages of the antibody. To assess efficacy of the antibody, an indicator of the disease (e.g., cancer) can be followed according to routine practice.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate cancer, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In certain embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In certain embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen, including the antibody used can vary over time.

For the purpose of the present disclosure, the appropriate dosage of an antibody described herein will depend on the specific antibody (or compositions thereof) employed, the type and severity of the cancer, whether the antibody is administered for preventive or therapeutic purposes, previous therapy, the patient's clinical history and response to the antibody, and the discretion of the attending physician. The administration of the antibodies described herein may be essentially continuous over a preselected period of time or may be in a series of spaced dose, e.g., either before, during, or after developing cancer.

As used herein, the term "treating" refers to the application or administration of a composition including one or more active agents to a subject, who has cancer, a symptom of cancer, or a predisposition toward cancer, with the purpose to cure, heal, alleviate, relieve, alter, remedy, ameliorate, improve, or affect cancer, the symptom of cancer, or the predisposition toward cancer.

Alleviating cancer includes delaying the development or progression of cancer, or reducing cancer severity. Alleviating cancer does not necessarily require curative results. As used therein, "delaying" the development of cancer means to defer, hinder, slow, retard, stabilize, and/or postpone progression of cancer. This delay can be of varying lengths of time, depending on the history of cancer and/or individuals being treated. A method that "delays" or alleviates the development of cancer, or delays the onset of cancer, is a method that reduces probability (the risk) of developing one or more symptoms of cancer in a given time frame and/or reduces extent of the symptoms in a given time frame, when compared to not using the method. Such comparisons are typically based on clinical studies, using a number of subjects sufficient to give a statistically significant result.

"Development" or "progression" of cancer means initial manifestations and/or ensuing progression of cancer. Development of cancer can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of cancer includes initial onset and/or recurrence.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

Diagnostic Applications

Described herein is a method for diagnosing cancer in a subject, comprising (a) applying a composition that includes one or more monoclonal antibodies that detect expression of SSEA-4, to a cell or tissue sample obtained from the subject; (b) assaying the binding of the monoclonal antibody to the cell or the tissue sample; and (c) comparing the binding with a normal control to determine the presence of the cancer in the subject.

Examples of the cancer for detection and diagnosis include, but are not limited to, sarcoma, skin cancer, leukemia, lymphoma, brain cancer, lung cancer, breast cancer, oral cancer, esophagus cancer, stomach cancer, liver cancer, bile duct cancer, pancreas cancer, colon cancer, kidney cancer, cervix cancer, ovary cancer and prostate cancer. In certain embodiments, the cancer is sarcoma, skin cancer, leukemia, lymphoma, brain cancer, lung cancer, breast cancer, ovarian cancer, prostate cancer, colon cancer, or pancreas cancer.

In certain embodiments, the antibody is capable of detecting Globo H, SSEA-3 and SSEA-4-expressing cancer cells. In certain embodiments, the antibody is capable of detecting Globo H and SSEA on cancer cells. In certain embodiments, the antibody is capable of detecting SSEA in cancers. In certain embodiments, the cancer is brain cancer or glioblastoma multiforme (GBM) cancer, and the antibody is an anti-SSEA-4 monoclonal antibody.

SSEA-4-specific monoclonal antibodies can be used alone or in combination for in vitro and in vivo diagnostic assays to detect SSEA-4-expressing cancer cells. In certain embodiments, SSEA-4 specific monoclonal antibodies are contacted with a biological sample from an individual having or suspected of having cancer, and antibody binding to a cell in the sample is determined when higher or lower than normal antibody binding indicates that the individual has cancer. In certain embodiments, the biological sample is a blood sample or blood fraction (e.g., serum, plasma, platelets, red blood cells, white blood cells). In certain embodiments, the biological sample is a tissue sample (biopsy), e.g., from a suspected tumor site, or from a tissue that is known to be affected, e.g., to determine the boundaries of a known tumor. In certain embodiments, the biological sample is obtained from a site of inflammation.

Biopsies are typically performed to obtain samples from tissues, i.e., non-fluid cell types. The biopsy technique applied will depend on the tissue type to be evaluated (e.g., breast, skin, colon, prostate, kidney, lung, bladder, lymph node, liver, bone marrow, airway or lung). In the case of a cancer the technique will also depend on the size and type of the tumor (e.g., solid, suspended, or blood), among other factors. Biopsy techniques are discussed, for example, in Harrison's Principles of Internal Medicine, Kasper, et al., eds., 16th ed., 2005, Chapter 70, and throughout Part V.

Any method of detecting antibody binding to a cell in a sample can be used for the present diagnostic assays. Methods of detecting antibody binding are well known in the art, e.g., flow cytometry, fluorescent microscopy, ELISAs, etc. In certain embodiments, the method comprises preparing the biological sample for detection prior to the determining step. For example, a subpopulation of cells (e.g., white blood cells) can be separated from the rest of the sample from the individual (e.g., other blood components) or cells in a tissue can be suspended for easier detection.

In certain embodiments, the percentage of SSEA-4 expressing cells in the sample is determined and compared to a control, e.g., a sample from an individual or group of individuals that are known to have cancer (positive control) or from an individual or group of individuals that are known not to have cancer (normal, non-disease, or negative control). In certain embodiments, the control is a standard range of SSEA-4 expression established for a given tissue. A higher or lower than normal percentage of/SSEA-4 expressing cells, or higher or lower expression level, indicates that the individual has cancer.

In one embodiment, a kit is provided for detecting SSEA-4 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of SSEA-4. Kits for detecting a polypeptide will typically comprise one or more antibodies that specifically bind SSEA-4, such as any of the antibodies disclosed herein. In a further embodiment, the antibodies are labeled (for example, with a fluorescent, radioactive, or an enzymatic label).

In one embodiment, a kit includes instructional materials disclosing means of use of one or more antibodies that specifically bind SSEA-4. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbent assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind to SSEA-4, as disclosed herein, can be used in these assays. Thus, the antibodies can be used in a conventional immunoassay, including, without limitation, an ELISA, an RIA, FACS, tissue immunohistochemistry, Western blot or immunoprecipitation.

Methods for Staging and/or Determining Prognosis of Tumors

Another aspect of the present disclosure features a method for staging and/or determining prognosis of tumors in a human patient, the method comprising: (a) applying a composition that includes one or more antibodies that detect the expression of markers consisting of SSEA-4 to a cell or tissue sample obtained from the patient; (b) assaying the binding of the monoclonal antibodies to the cell or the tissue sample; (c) comparing the expression level of the markers in the test sample with the level in a reference sample, and (d) determining the stage and/or prognosis of tumors in the patient based upon the outcome identified in step (c).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Hybridoma Fusion and Screening

A classical hybridoma fusion was performed. Mice received their first immunization with SSEA-4-DT-CRM197 (diphtheria toxin cross reacting material 197) conjugated with OBI-821 saponin adjuvant. Each mouse was administrated with designated treatment via subcutaneous (s.c.) injection at both left and right abdominal sites (100 µL/site). The mice were dosed four times (Day 0, Day 7, Day 14, and Day 23). Blood sample (approximately 0.1 mL whole blood/time point/animal) was obtained through facial vein without anticoagulant before Day 0 (pre-dose), Day 10, Day 17, Day 26 and on the sacrifice day (Day 35, volume of whole blood was collected through facial vein and heart punch). Coagulated blood samples were centrifuged (1500× g, 15 min, 4° C.), and serum was separated and transferred into eppendorf tubes. All serum samples were tested for titers of anti-SSEA-4 antibody. Five mice were found to produce high levels of anti-SSEA-4 IgG and IgM and were used for hybridoma production. Mouse myeloma cells were used for fusion with the mouse splenocytes following procedure of a Köhler and Milstein (Köhler G. and Milstein C, 1975). Hybridoma supernatants were screened by affinity ELISA with 0.2 µg SSEA-4-lipid 1/per well. The commercial SSEA-4 Antibody (MC-813-70) (Biolegend; Cat #330402) served as positive controls. The OD of hybridoma clone with no dilution of supernatant. Background×2 was selected. Top three hybridoma clones were 1G1s, Ms and 2F20s.

Example 2: Measurement of the Anti-Tumor Activity of the Exemplary Antibody in Nude Mice In a xenograft tumor model of human pancreatic adenocarcinoma, HPAC cells were subcutaneously (s.c.) implanted into BALB/c male nude mice and test articles were administered at 0.4 mg/kg by intraperitoneal (i.p.) injection twice weekly for 5 weeks starting when the average tumor size reached 50-120 mm$^3$. The tumor size was monitored and recorded twice weekly for 36 days. Mortality, body weight, and signs of overt animal toxicity were also recorded twice weekly for 36 days. Tumor growth was calculated as T/C (treatment/control)×100%.

Test Substances and Dosing Pattern

Test substances were prepared at 1.45, 1, or 0.5 mg/mL in liquid form. Test substances were freshly prepared each day before dosing by diluting stocks solutions with phosphate buffer saline (PBS, pH7.4) to obtain the designated dosing concentration (0.04 mg/mL). Test substances were administered intraperitoneally (i.p.) at a dosing volume at 10 mL/kg twice weekly for 5 weeks.

TABLE 4

The exemplary types of formulation.

| Test Compound | Vehicle | Solubility[a] | Color | Light Protection[b] | Temperature[c] | Formulation mg/mL |
|---|---|---|---|---|---|---|
| Globo H-2C2 | PBS, pH 7.4 | S | Colorless | N | 4° C. | 0.04 |
| commercial SSEA-4 Ab (MC-813-70) | PBS, pH 7.4 | S | Colorless | N | 4° C. | 0.04 |
| 1G1s | PBS, pH 7.4 | S | Colorless | N | 4° C. | 0.04 |
| 1J1s | PBS, pH 7.4 | S | Colorless | N | 4° C. | 0.04 |
| 2F20s | PBS, pH 7.4 | S | Colorless | N | 4° C. | 0.04 |

[a]This is based upon visual observation S: soluble; SS: slightly soluble; I: insoluble (suspension or precipitation)
[b]Y: formula is kept in tube or vial with brown color, or covered with aluminum foil. N: no protection from light
[c]RT: prepared fresh and stored between 20-25° C. 4° C. prepared fresh and stored in the refrigerator or kept on ice.

Cell Line

HPAC tumor cell line (ATCC CRL-2119, human pancreatic adenocarcinoma) was prepared and cultured at Eurofins Panlabs Taiwan Ltd. before subcutaneous implantation at 0.1 mL of 1×10$^6$ cells/mouse into the right flank of BALB/c male nude mice.

Animals

BALB/c male nude mice, 6-7 weeks of age, weighing 18-22 g were obtained from BioLasco Taiwan (under Charles River Laboratories Licensee). All animals were maintained in a well-controlled temperature (20-24° C.) and humidity (30-70%) environment with 12 hours light/dark cycles. Free access to standard lab diet [MFG (Oriental Yeast Co., Ltd., Japan)] and autoclaved tap water were granted. All aspects of this study including housing, experimentation, and animal disposal were performed in general accordance with the "Guide for the Care and Use of Laboratory Animals: Eighth Edition" (National Academies Press, Washington, D.C., 2011) in our AAALAC-accredited laboratory animal facility. In addition, the animal care and use protocol was reviewed and approved by the IACUC at Eurofins Panlabs Taiwan, Ltd.

Chemicals

DMEM/F12 medium (Invitrogen, USA), Epidermal growth factor (R&D Systems, USA), Fetal bovine serum (Invitrogen, USA), Insulin (Sigma, USA), Hydrocortisone (Sigma, USA) and Penicillin/streptomycin solution (Invitrogen, USA).

Equipment

Animal cage (Tecniplast, Italy), Beaker 1000 mL (Kimax, USA), Calipers (Mitutoyo, Japan), Class II biological safety cabinet (NuAire, USA), Centrifuge 5810 R (Eppendorf, Germany), μ incubator (Forma Scientific Inc., USA), Individually ventilated cages (IVC, 36 Mini Isolator system) (Tecniplast, Italy), Mouse scale #Z-40 (Taconic, USA), Stainless forceps (Klappenecker, Germany) and Vertical laminar flow (Tsao-Hsin, Taiwan).

Methods

BALB/c nude male mice at 6-7 weeks of age and weighing 18-22 g were used. Human pancreatic adenocarcinoma tumor cells HPAC (ATCC CRL-2119, $1.0 \times 10^6$ in 0.1 mL) were injected subcutaneously into the right flank of the animals. The animals were subsequently divided into 6 groups, consisting of 5 animals in each group. The administration of test substances and the vehicle was initiated when the average tumor size reached 50-120 mm$^3$ (set as Day 1). Test substances (0.4 mg/kg) were prepared freshly prior to each dosing. Test substances and the vehicle were administered twice weekly by intraperitoneal injection (i.p.) for 5 weeks. Tumor size, body weight, and mortality were recorded twice weekly for 36 days prior to administrations of test substances or the vehicle. Photos of the animals bearing the grown tumors were taken at the end of the study (FIGS. 1-6).

Tumor volume (mm$^3$) was determined according to the ellipsoid formula: length×(width)×0.5. Tumor growth (T/C) was calculated using the following formula: T/C=(Tn)/(Cn)×100%, where C1 (Cn) is the tumor volume of day n in the control group, and T1 (Tn) is the tumor volume of day n in the treated group. T/C value ≤42% was considered significant antitumor activity.

Results

TABLE 5-1

Tumor, Xenograft, Pancreas, HPAC, in Nude Mice

| Gr. | Treatment | Dose (mg/kg) (Route) | No. | Day 1 | Day 4 | Day 8 | Day 11 | Day 15 | Day 18 | Day 22 | Day 25 | Day 29 | Day 32 | Day 36 |
|---|---|---|---|---|---|---|---|---|---|---|---|---|---|---|
| 1 | Vehicle (PBS, pH 7.4) | 10 mL/kg × 10, IP (Twice weekly) | 1 | 70 | 93 | 164 | 225 | 250 | 336 | 529 | 670 | 954 | 1161 | 1565 |
|  |  |  | 2 | 72 | 81 | 146 | 181 | 227 | 248 | 351 | 387 | 428 | 502 | 575 |
|  |  |  | 3 | 76 | 94 | 176 | 192 | 300 | 317 | 555 | 617 | 708 | 926 | 991 |
|  |  |  | 4 | 55 | 72 | 104 | 127 | 203 | 217 | 242 | 342 | 474 | 543 | 562 |
|  |  |  | 5 | 47 | 62 | 110 | 118 | 152 | 179 | 240 | 314 | 381 | 443 | 507 |
|  |  |  | Mean | 64 | 80 | 140 | 169 | 226 | 259 | 383 | 466 | 589 | 715 | 840 |
|  |  |  | SEM | 6 | 6 | 14 | 20 | 25 | 30 | 68 | 74 | 107 | 111 | 159 |
| 2 | Globo H-2C2 | 0.4 mg/kg × 10, IP (Twice weekly) | 1 | 83 | 108 | 166 | 202 | 262 | 252 | 368 | 396 | 541 | 572 | 657 |
|  |  |  | 2 | 79 | 98 | 158 | 177 | 244 | 289 | 428 | 508 | 635 | 844 | 886 |
|  |  |  | 3 | 49 | 62 | 70 | 87 | 115 | 128 | 154 | 200 | 201 | 250 | 329 |
|  |  |  | 4 | 52 | 68 | 93 | 113 | 122 | 143 | 186 | 267 | 269 | 317 | 379 |
|  |  |  | 5 | 53 | 84 | 104 | 127 | 163 | 195 | 233 | 272 | 340 | 297 | 340 |
|  |  |  | Mean | 63 | 84 | 118 | 141 | 181 | 201 | 274 | 329 | 397 | 456 | 518 |
|  |  |  | SEM | 7 | 9 | 19 | 21 | 31 | 31 | 53 | 55 | 82 | 89 | 87 |
|  |  |  | % T/C | 98 | 105 | 84 | 83 | 80 | 78 | 72 | 71 | 67 | 64 | 62 |
| 3 | Commercial SSEA-4 Ab (MC-813-70) | 0.4 mg/kg × 10, IP (Twice weekly) | 1 | 59 | 49 | 72 | 72 | 109 | 132 | 194 | 214 | 246 | 314 | 360 |
|  |  |  | 2 | 61 | 76 | 97 | 134 | 184 | 252 | 321 | 395 | 585 | 670 | 763 |
|  |  |  | 3 | 60 | 91 | 148 | 200 | 240 | 313 | 424 | 505 | 701 | 779 | 1018 |
|  |  |  | 4 | 54 | 66 | 100 | 140 | 223 | 256 | 325 | 404 | 451 | 620 | 702 |
|  |  |  | 5 | 84 | 125 | 228 | 288 | 424 | 530 | 635 | 856 | 1262 | 1554 | 2056 |
|  |  |  | Mean | 64 | 81 | 129 | 167 | 236 | 297 | 380 | 475 | 649 | 787 | 980 |
|  |  |  | SEM | 5 | 13 | 28 | 36 | 52 | 65 | 74 | 106 | 171 | 163 | 228 |
|  |  |  | % T/C | 100 | 101 | 92 | 99 | 104 | 115 | 99 | 102 | 110 | 110 | 117 |

TABLE 5-2

Tumor, Xenograft, Pancreas, HPAC, in Nude Mice (Continued)

| Gr. | Treatment | Dose (mg/kg) (Route) | No. | Day 1 | Day 4 | Day 8 | Day 11 | Day 15 | Day 18 | Day 22 | Day 25 | Day 29 | Day 32 | Day 36 |
|---|---|---|---|---|---|---|---|---|---|---|---|---|---|---|
| 4 | 1G1s | 0.4 mg/kg × 10, IP (Twice weekly) | 1 | 45 | 118 | 133 | 125 | 189 | 225 | 268 | 314 | 369 | 384 | 841 |
|  |  |  | 2 | 57 | 62 | 103 | 163 | 189 | 254 | 339 | 377 | 519 | 588 | 664 |
|  |  |  | 3 | 62 | 98 | 130 | 181 | 245 | 312 | 362 | 468 | 547 | 626 | 706 |
|  |  |  | 4 | 83 | 80 | 95 | 121 | 171 | 203 | 259 | 322 | 415 | 490 | 579 |
|  |  |  | 5 | 78 | 83 | 149 | 166 | 234 | 310 | 340 | 407 | 505 | 553 | 583 |
|  |  |  | Mean | 65 | 88 | 122 | 151 | 206 | 261 | 314 | 378 | 471 | 528 | 675 |
|  |  |  | SEM | 7 | 9 | 10 | 12 | 14 | 22 | 21 | 28 | 34 | 34 | 38 |
|  |  |  | % T/C | 102 | 110 | 87 | 89 | 91 | 101 | 82 | 81 | 80 | 74 | 80 |
| 5 | 1J1s | 0.4 mg/kg × 10, IP (Twice weekly) | 1 | 47 | 79 | 142 | 164 | 194 | 222 | 227 | 282 | 356 | 424 | 427 |
|  |  |  | 2 | 73 | 91 | 127 | 159 | 181 | 266 | 366 | 408 | 482 | 545 | 610 |
|  |  |  | 3 | 41 | 52 | 65 | 93 | 122 | 150 | 202 | 233 | 329 | 376 | 426 |

TABLE 5-2-continued

Tumor, Xenograft, Pancreas, HPAC, in Nude Mice (Continued)

| Gr. | Treatment | Dose (mg/kg) (Route) | No. | Day 1 | Day 4 | Day 8 | Day 11 | Day 15 | Day 18 | Day 22 | Day 25 | Day 29 | Day 32 | Day 36 |
|---|---|---|---|---|---|---|---|---|---|---|---|---|---|---|
| | | | 4 | 77 | 72 | 136 | 211 | 277 | 291 | 308 | 333 | 473 | 473 | 493 |
| | | | 5 | 68 | 87 | 122 | 153 | 193 | 285 | 455 | 477 | 602 | 721 | 826 |
| | | | Mean | 61 | 76 | 118 | 156 | 193 | 243 | 312 | 347 | 448 | 508 | 556 |
| | | | SEM | 7 | 7 | 14 | 19 | 25 | 26 | 46 | 44 | 49 | 48 | 60 |
| | | | % T/C | 95 | 95 | 84 | 92 | 85 | 94 | 81 | 74 | 76 | 71 | 66 |
| 6 | 2F20s | 0.4 mg/kg × 10, IP (Twice weekly) | 1 | 53 | 74 | 85 | 129 | 164 | 161 | 231 | 265 | 375 | 402 | 499 |
| | | | 2 | 50 | 51 | 74 | 110 | 129 | 162 | 208 | 259 | 393 | 411 | 520 |
| | | | 3 | 92 | 95 | 175 | 244 | 268 | 322 | 446 | 447 | 637 | 670 | 768 |
| | | | 4 | 73 | 83 | 127 | 162 | 214 | 269 | 337 | 348 | 446 | 490 | 514 |
| | | | 5 | 52 | 59 | 86 | 109 | 158 | 206 | 273 | 296 | 450 | 516 | 536 |
| | | | Mean | 64 | 72 | 109 | 151 | 187 | 224 | 299 | 323 | 460 | 498 | 567 |
| | | | SEM | 8 | 8 | 19 | 25 | 25 | 31 | 43 | 35 | 47 | 38 | 40 |
| | | | % T/C | 100 | 90 | 78 | 89 | 83 | 86 | 78 | 69 | 78 | 70 | 68 |

Test substances were administered intraperitoneally twice weekly for 5 weeks. Tumor size was measured and recorded twice weekly for 36 days. Tumor growth was calculated as T/C (treatment/control)×100%.

T/C value ≤42% was considered significant antitumor activity. In addition, two-way ANOVA followed by Bonferroni test was applied to ascertain the statistically significant difference compared to Group 1 (Vehicle, PBS) at * P<0.05.

Figure 7:
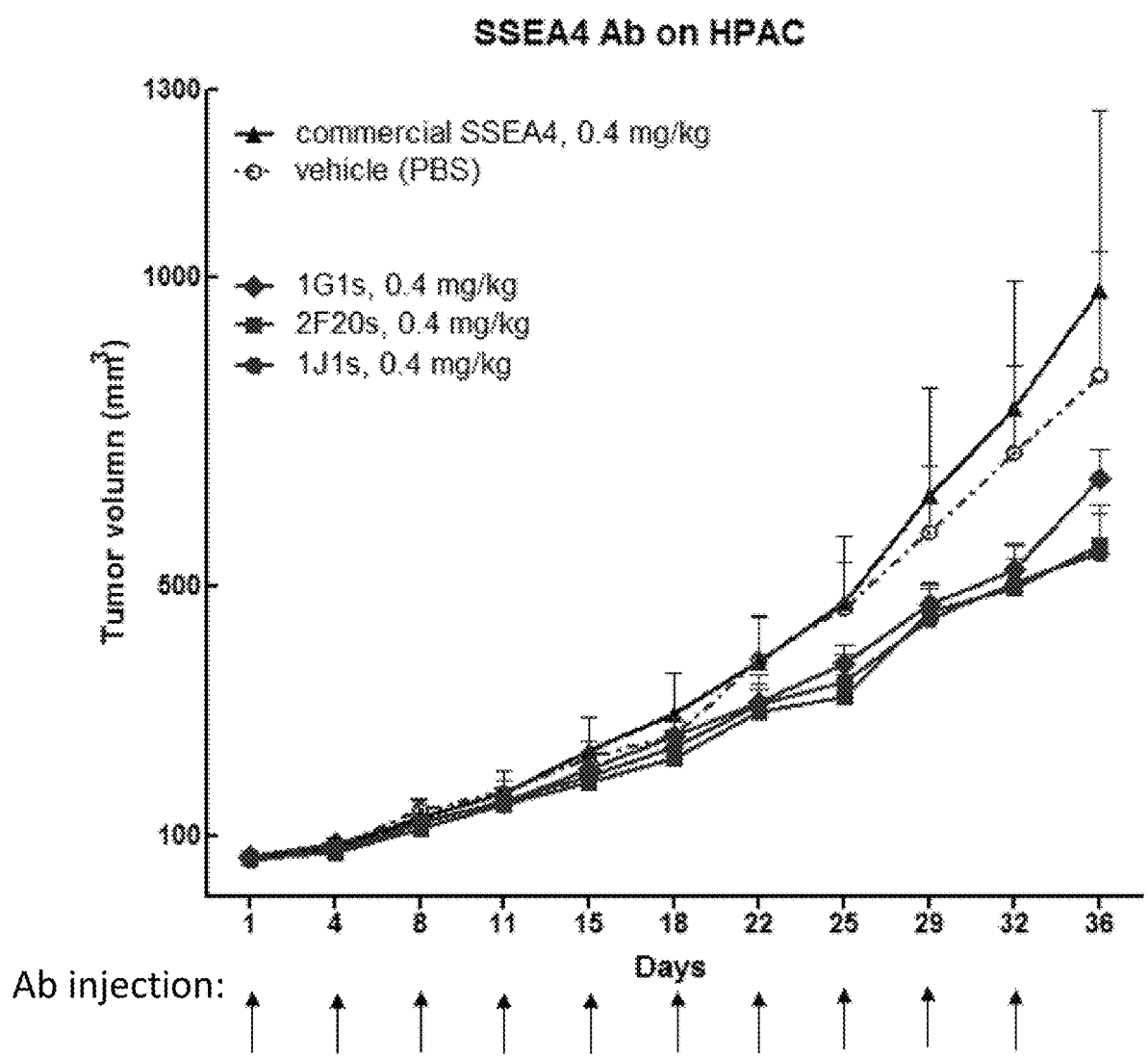
FIG. 7 shows a graph of measurements of tumor volume during the course of antibody injections over 36 days. The effect of SSEA-4 antibodies 1G1s, 2F20s and Ms were measured on HPAC tumors. Commercial SSEA-4 antibody (MC-813-70) and vehicle (PBS) were also measured.

FIGS. 1-6 show the photos of Nude Mice with administering different test compounds for 36 Days. The tumor inhibition ability was calculated as 19.6% of 1G1s, 33.8% of Ms and 32.5% of 2F20s. It indicated that both Ms and 2F20s have the better tumor inhibition ability (FIG. 7).

Example 3: Determination of Cell Binding Ability of the Exemplary Antibody with MCF7 by FACS Cell Culture MCF-7 cell were cultured in Minimum essential medium (Invitrogen, Cat #10370021) with 2 mM L-glutamine (Invitrogen, Cat #25030081) and 1 mM sodium pyruvate (Invitrogen, Cat #11360070) and supplemented with 0.01 mg/mL insulin (Sigma, Cat #SI-I9278-5 mL), 10% fetal bovine serum (Invitrogen, Cat #16000044).

Cell Staining

Test cells were suspended by discarding media from the test sample flask containing monolayer cells. Cells were rinsed with 5 mL PBS twice. 1 mL of 0.05% trypsin was added to flask, swirled to cover all surface area, and put in a 37° C. $CO_2$ incubator for 5-10 minutes. 5 mL of complete growth medium was added. Cells were aspirated by pipetting gently. Cell suspension was transferred to a 15 mL conical tube. The tube was centrifuged for 5 minutes at 200 g. Following centrifugation, the supernatant was removed, and the cell pellet was agitated.

Cell Counting 1-2 mL FACS buffer was added to the cell pellet and mixed well by pipetting. Cells were added onto the 5 mL Polystyrene Round-Bottom Tube with Cell-Strainer Cap (Falcon, Cat #352235) to obtain intact and viable single cells. 10 µL cell suspension was transferred to a microcentrifuge tube. 10 µL of Trypan Blue Solution (0.4% Trypan blue) was added and mixed well by pipetting, then viable cells were counted on a hematocytometer. Cell concentration was adjusted to be $4 \times 10^6$ cells/mL, and then 50 µL cell suspension was pipetted into polystyrene round tubes to make $2 \times 10^5$ cells per tube.

Primary Antibody

TABLE 6

Exemplary primary antibodies

| Clone name | Isotype control name |
|---|---|
| 1G1s | Purified Mouse $IgG_{2b}$ (Biolegend, Cat #400302) |
| 1J1s | Purified Mouse $IgG_1$ (Biolegend, Cat #401402) |
| 2F20s | Purified Mouse $IgG_{2a}$ (Biolegend, Cat #401502) |
| Alexa Fluor ® 488 anti-human SSEA-4 antibody (Biolegend, Cat #330412) | Alexa Fluor ® 488 Mouse $IgG_3$ (Biolegend, Cat #401324) |

The primary antibody was diluted in FACS buffer to final antibody concentration of 10 µg/mL. 50 µL antibody diluent was added to 50 µL cell suspension to reach 0.5 µg antibody per tube. Each tube was vortexed gently to mix cell suspension and first antibody well, then tubes were placed on ice for incubation of approximately 30 minutes. Every tube was filled with 1 mL FACS buffer, and washed one time each by centrifuging at 400 g for 5 minutes. Supernatant was discarded by vacuum suction, being careful of the suction action and avoiding touching the bottom of the tube that may cause cell loss.

Secondary Antibody

Secondary antibodies used for assay setup: 1 mg, Goat anti-Mouse IgG, Human ads-FITC (Southern Biotech, Cat #1030-02) for 1G1s, Ms and 2F20s assay. The secondary antibody was diluted in FACS buffer to a final antibody concentration of 4 µg/mL. 100 µL diluted secondary antibody was added to every tube, then each tube was vortexed gently to mix cell suspension and secondary antibody well. Tubes were placed on ice and light avoided for an incubation time of approximately 30 minutes. Then, every tube was filled with 1 mL FACS buffer, and washed one time each by centrifuging at 400 g for 5 minutes. The supernatant was discarded by vacuum suction, being careful of the suction action and avoiding touching the bottom of the tube that may cause cell loss. 300 µL of 4% paraformaldehyde fixed solution was added to every tube and tubes placed on ice, while avoiding light, for incubation of approximately 30 minutes. Every tube was filled with 1 mL FACS buffer, and washed each one time by centrifuging at 400 g for 5 minutes. Then, the supernatant was discarded by vacuum suction, being careful of the suction action and avoiding touching the bottom of the tube that may cause cell loss. The test cell tube was resuspended with 400 µL of FACS buffer and then stored in 4±2° C. refrigerator, avoiding light.

Flow Cytometry Analysis

Figure 8A:
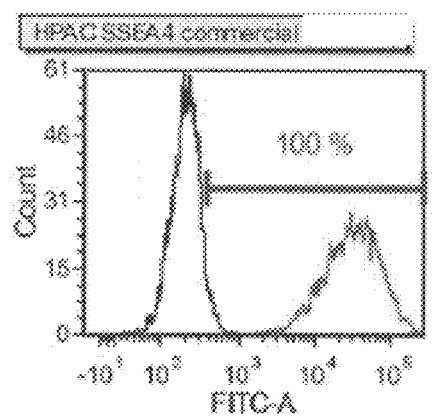
FIG. 8 shows flow cytometry histograms. 2×10$^5$ cells/tube were stained with tested antibody (green line) or isotype control (black line) followed by incubation with FITC-conjugated secondary antibody.
Figure 8B:
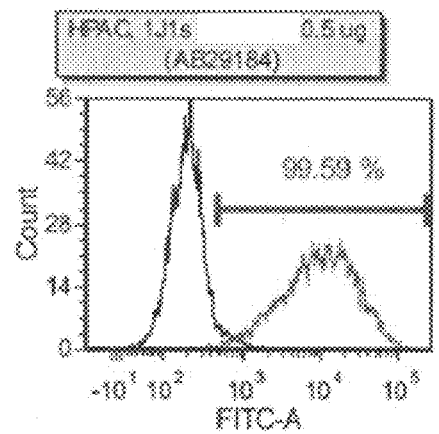
Figure 8C:
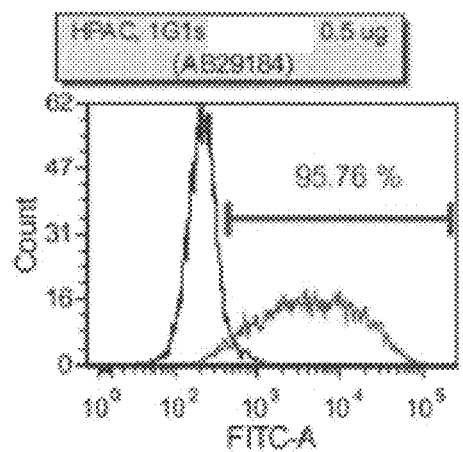
Figure 8D:
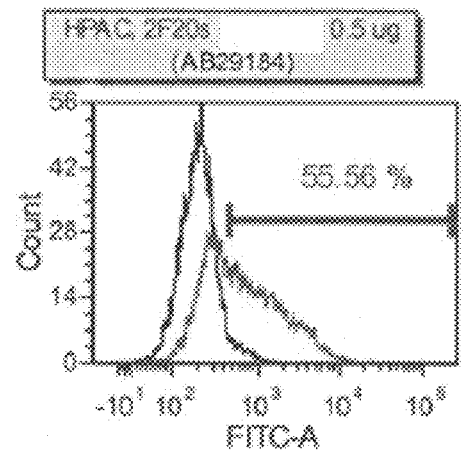

Flow cytometry was performed right after staining. To perform data analysis, the percentage of MCF7 cell binding were analyzed by FCS Express 4 Flow Research software. In the histogram plot, isotype control was gated and defined that 5% of gated cells were background. Based on the setting of the background, the percentage of binding region (M1) of test cell tube was determined. At this setting, test cell of 5% or greater above the isotype control were considered as positive binding of MCF7 cells. FIG. 8A shows 100% of commercial SSEA-4 antibody (MC-813-70), on HPAC cells. FIG. 8B shows 99.59% of Ms on HPAC cells. FIG. 8C shows 55.56% of 2F20s on HPAC cells. FIG. 8D shows 95.76% of 1G1s on HPAC cells. It indicates Ms has the best cell binding affinity on HPAC cell (Pancreatic cell line). In addition, FIG. 9 shows FACS binding assay results of exemplary SSEA-4 antibodies to various cancer and non-cancer cell lines. It also indicates Ms has the best cell binding affinity on MCF-7 (breast cancer), MDA-MB231 (breast cancer) and HK2 (kidney, cortex/proximal tubule).

Example 4: Epitope Mapping of Exemplary Anti-SSEA4 IgG Antibody by ELISA Analysis with SSEA-4, SS Serial and Gb Serial Sugars Reagent/Buffer Preparation Coating Antigen SSEA4-lipid1, SSEA4-ceramide, SS serial sugars-lipid 1, and Gb serial sugars-lipid 1 powder were dissolved in 100% ethanol in glass bottle and stored at 4° C. until use. The 10× Blocking Buffer (Sigma, Cat #B6429) was diluted in double-distilled water (d.d. $H_2O$) to 1× for use. Wash Buffer: 0.5 mL of Tween 20 was added into 1 L of PBS to make a 0.05% Tween 20 in PBS.

Primary Antibody

Commercial MC-813-70 SSEA4 antibody (BioLegend, Cat #330402), 1G1s, Ms, and 2F20s SSEA4 antibodies were diluted in Blocking Buffer at 10 µg/mL in Eppendorf tubes.

Secondary Antibody

Goat anti-mouse IgG-AP (Southern Biotech, Cat #1030-04), was rehydrated to make 2.0 mL of 0.3 mg/mL solution in d.d. $H_2O$. 1.0 mL of glycerol (ACS grade or better) was added to a 2 mL eppendorf to reach the 1 mL scale tick of the eppendorf. 0.5 mL of rehydrated antibody was transferred into the glycerol, mixed well and stored at −20±2° C. refrigerator.

Substrate Solution

Substrate Solution (Alkaline Phosphatase Yellow (pNPP) Liquid Substrate System for ELISA, Sigma, Cat #P7998) originally stored at 4° C. was warmed in 37° C. water bath before use.

Plate Coating

20 µg of the individual SSEA4-lipid1, SSEA4-ceramide, lipid1 conjugated SS/Gb serial sugars (Coating Antigens) were added to 5 mL ethanol and mixed gently (0.2 µg of sugars/well×100-well plate=20 µg; 50 µL/well×100 well=5 mL). 50 µL of coated antigens were pipetted into each well of individual plates on ice. Plates was labeled, covered with lid and incubated at room temperature overnight. 100 µL of Blocking Buffer was added to each well and incubated at room temperature (22-26° C.) for approximately 30 minutes.

120 µL 1:50 diluted primary antibodies (10 µg/mL) were pipetted to the top well of Column 2. Then 180 µL was added for the rest of Column 2 wells, leaving the first column (Column 1) empty for blank. 60 µL of 10 µg/mL primary antibodies were transferred from the first well to second well (2.5 µg/mL anti-SSEA-4 antibodies). Wells were mixed by pipetting repeatedly. Process was repeated and the following well of primary antibodies dilutions (fourfold dilution) were made: $1^{st}$ well=10 µg/mL (1:50 dilution), $2^{nd}$ well=2.5 µg/mL (1:200 dilution), $3^{rd}$ well=0.625 µg/mL (1:800 dilution), $4^{th}$ well=0.156 µg/mL (1:3200 dilution), $5^{th}$ well=0.039 µg/mL (1:12800 dilution), $6^{th}$ well=0.01 µg/mL (1:51200 dilution), $7^{th}$ well=0.025 µg/mL (1:204800 dilution), $8^{th}$ well=0.0006 µg/mL (1:819200 dilution).

Following the 30 minutes incubation of the antigen-coated plate with Blocking Buffer, Blocking Buffer was removed by aspiration and each well washed three times with 200 µL Wash Buffer. 50 µL diluted positive control (commercial SSEA-4 Antibody MC-813-70) and exemplary primary antibodies were added from Dilution Plates to wells in the Test Plates for individual SSEA4 coating antigen. Test Plates were covered, labeled, and incubated at room temperature for approximately 1 hour. After incubation, wells were aspirated and washed three times with 200 µL Wash Buffer.

25 µL of Secondary Antibody was added to 4975 µL of Blocking Buffer (1:200 dilution) and mixed gently (50 µL/well×100-well plate=5 mL). 50 µL of Secondary Antibody Solution was pipetted into each well. Plates were covered, labeled, and incubated at room temperature for approximately 45 minutes. After incubation, Secondary Antibody Solution was aspirated from all wells and all wells washed four times with 200 µL Wash Buffer.

100 µL Substrate Solution was pipetted into each well and incubated for 20 minutes at 37±2° C., stopped by the addition of 50 µL of Stop Solution (Alkaline Phosphatase Stop Solution, Sigma, Cat #A5852), mixed well and then plate was read at 405 nm on the ELISA Plate Reader.

Data Analysis

Data were analyzed statistically and draw the curve by Sigmoidal dose-response (variable slope) method using GraphPad Prism 6 Software and Mean and SD were calculated from the duplicated results. Secondary antibody only as negative control.

Figure 10:
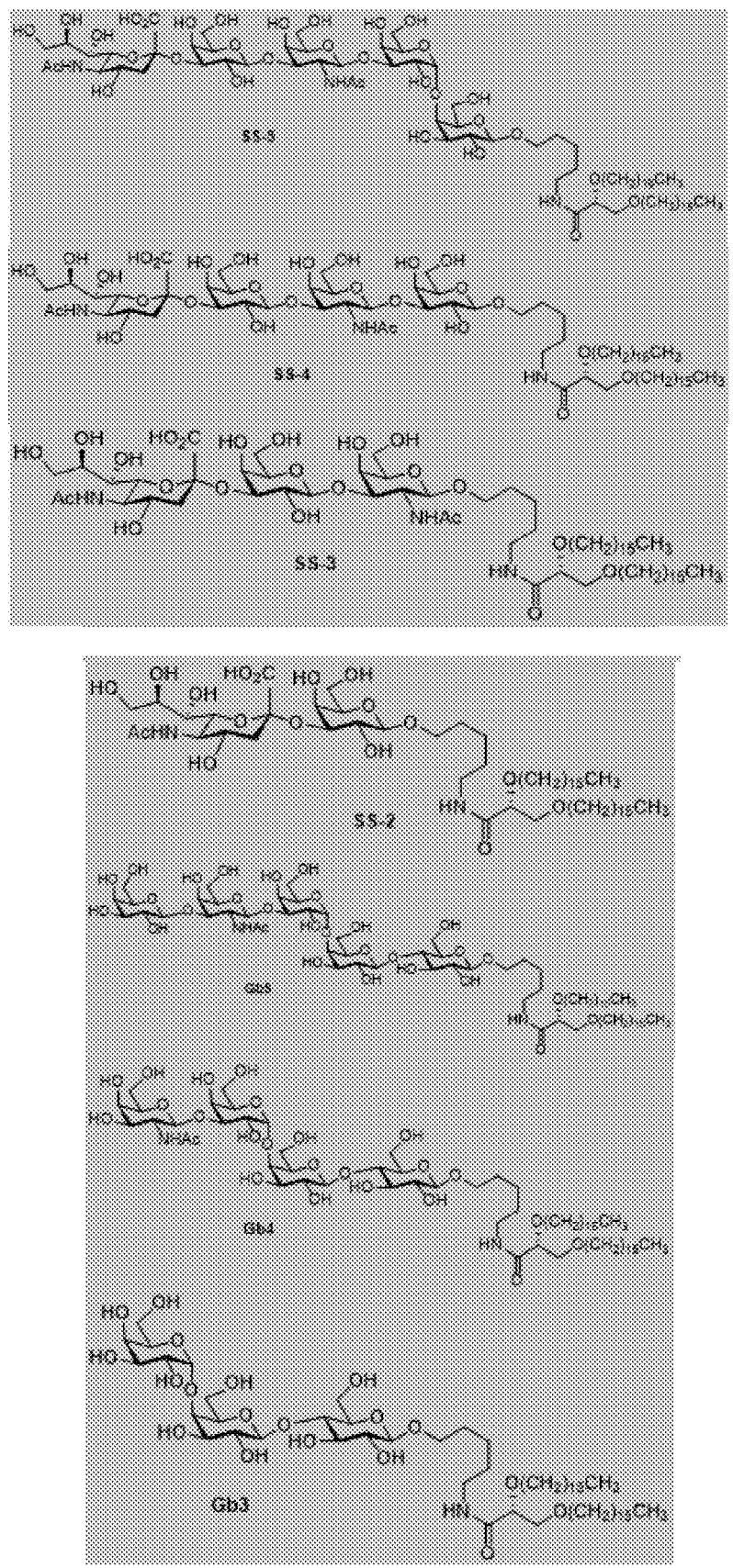
FIG. 10 shows the structure of SS serial sugars and Gb serial sugars conjugated to lipid1.
Figure 11A:
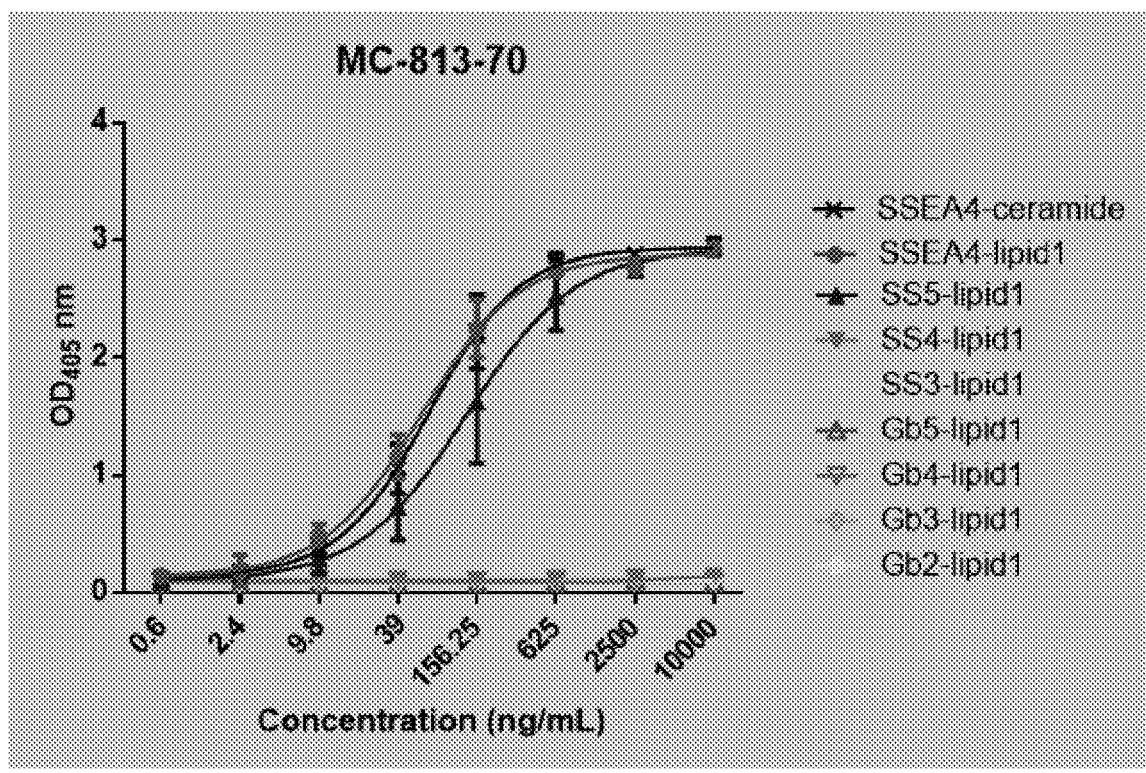
FIG. 11A: commercial SSEA-4 antibody (MC-813-70)
Figure 11B:
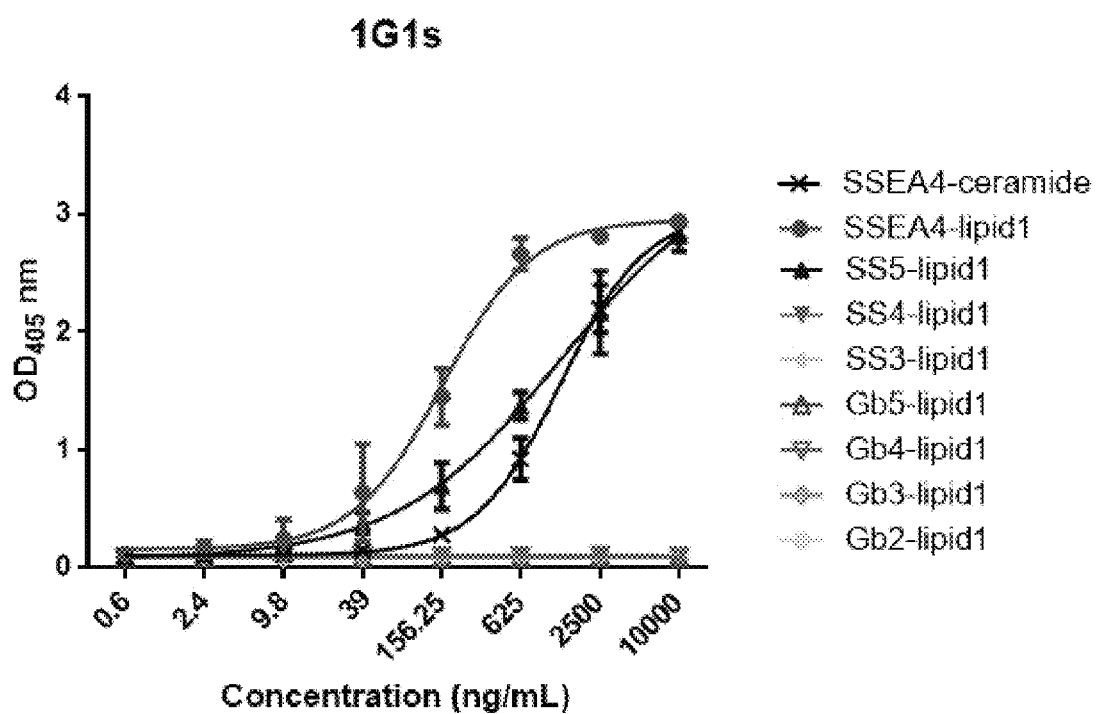
FIG. 11B: 1G1s.
Figure 11C:
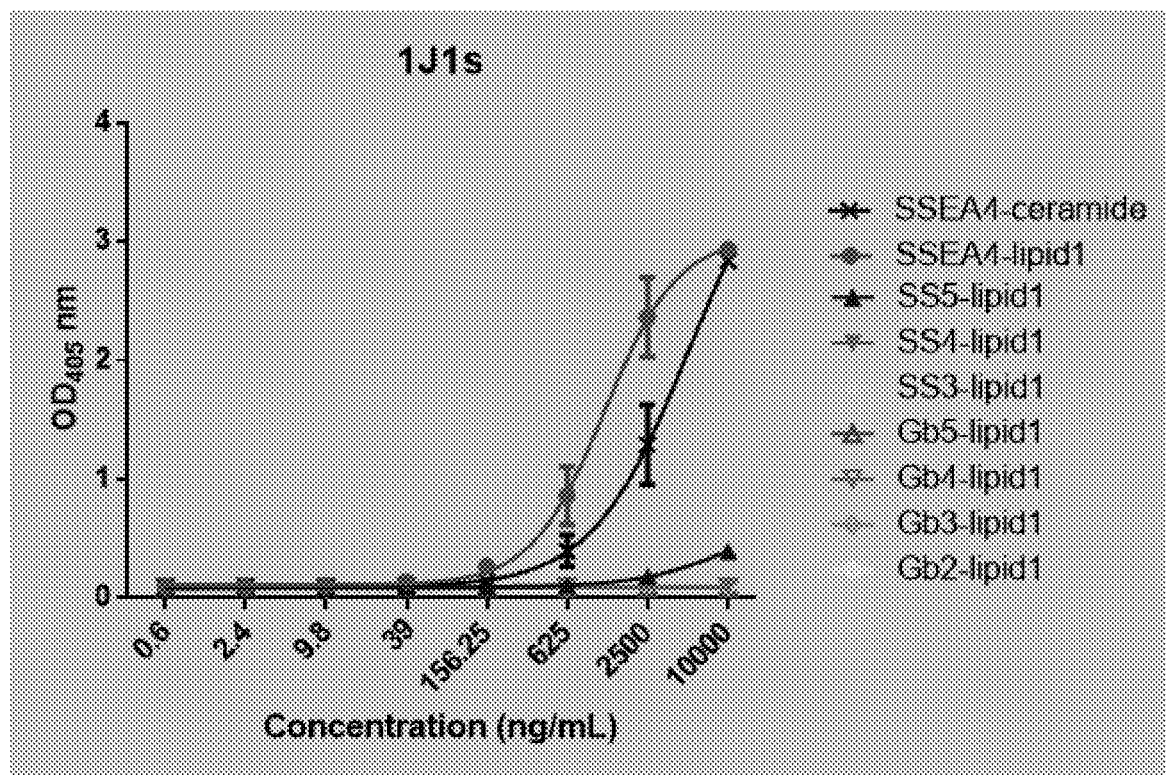
FIG. 11C: 1J1s.
Figure 11D:
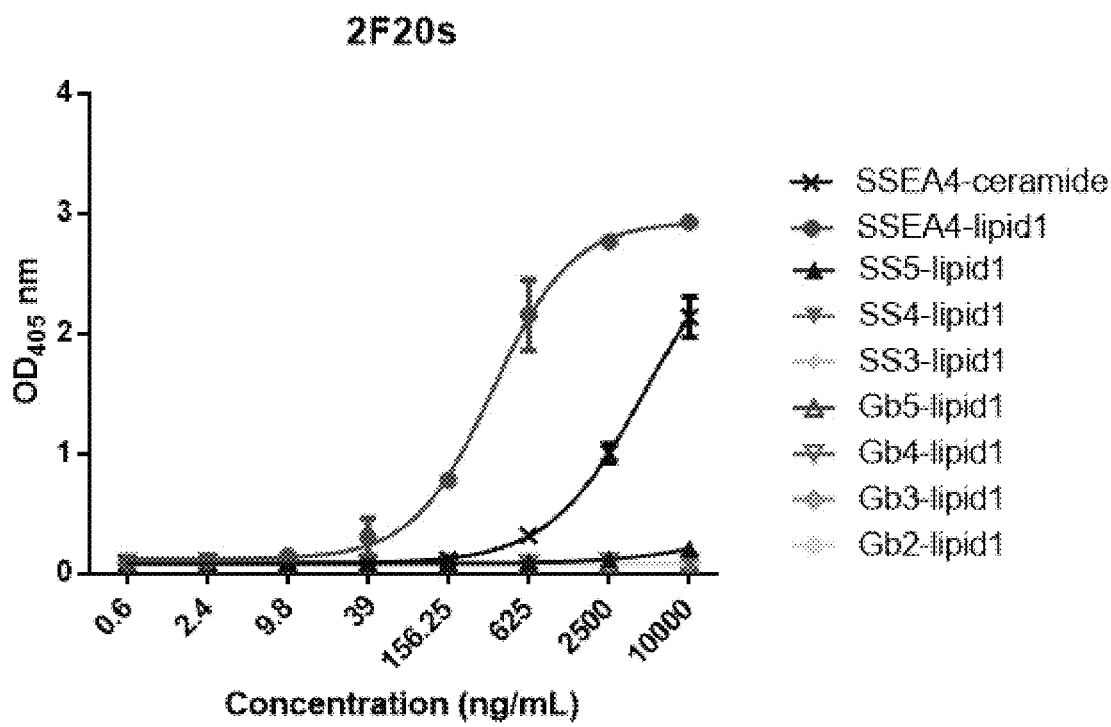
FIG. 11D: 2F20s.

FIG. 10 shows the structure of truncated SSEA-4: SS serial sugars and Gb serial sugars conjugated with lipid1. FIG. 11 shows the epitope mapping result of primary SSEA-4 antibodies. Truncated glycan terminal antigens showed that a complete SSEA-4 structure is required for Ms and 2F20s recognition. On the other hand, commercial SSEA-4 antibody MC-813-70 and 1G1s also recognize both SSEA-4 and SS5 due to the last compound structure (N-Acetylneuraminic Acid; NeuAc). It means the first compound structure (Glucose) at the reducing end of sugar is less essential for epitope recognition.

Example 5: Cross Activity with Exemplary Biotinylated Sugars by SSEA-4-Lipid1 Coating Chemiluminescent Sandwich ELISA Analysis Reagents SuperBlock, the blocking buffer (ThermoFisher, Cat #37515) was used as-is. Primary SSEA-4 antibodies (1G1s, Ms, 2F20s, and MC-813-70) were diluted in SuperBlock at 2.5 µg/mL. Wash Buffer: 0.5 mL of Tween 20 was added into 1 L of PBS to make a 0.05% Tween 20 in PBS. Secondary Antibody: Goat anti-mouse IgG-HPR (Jackson ImmunoResearch, Cat #109-035-003) in SuperBlock at 1:50000 dilution. Biotinylated sugars (listed below) and D-Biotin (Carbosynth, Cat #FB02633) was dissolved in 1×PBS (Sigma, Cat #P5493-4L) to make 1 mg/mL stock.

TABLE 7

List of tumor associated sugars (coated antigens)
Tumor Associated Sugar

α-Glucose
α-Galactose
α-Man-6-phosphate
α-L-Rhamnose
H types3: Fucα1-2Galβ1-4GalNAcβ
(NeuAcα2-8)$_2$
NeuAcβ2-6GalNAcα
(NeuAcα2-8)$_3$
Blood Group B:Galα1-3(Fucα1-2)Galβ
6Gal-HSO$_3$-SiaLex:Neu5Acα2-3(6-HSO$_3$)Galβ1-4(Fucα1-3)GlcNAcβ
6GlcNAc-HSO$_3$-SiaLex:Neu5Acα2-3Galβ1-4(Fucα1-3)(6-HSO$_3$)GlcNAcβ
α2-6 sialylated diantennary N-glycans: (NeuAcα2-6Galα1-4GlcNAcα1-2Man)$_2$α1-3,6Manα1-4GlcNAcα1-4GlcNAc
GD2:GalNAcβ1-4(NeuAcα2-8NeuAcα2-3)Galβ1-4Glc-β
(OligoTech; Cat# GLY094-NAc-sp3-Bt)
GM2:GalNAcβ1-4(NeuAcα2-3)Galβ1-4Glc-β
(OligoTech; Cat# GLY093-NAc-sp3-Bt)
SSEA4 hexaose: Neu5Acα2-3Galβ1-3GalNAcβ1-3Galα1-4Galβ1-4Glcβ
(OligoTech; Cat# GLY131-NAc-sp3-Bt)
GD3:NeuAcα2-8NeuAcα2-3Galβ1-4Glc-β
(OligoTech; Cat# GLY091-NAc-sp3-Bt)
Fucosyl-GM1:Fucα1-2Galβ1-3GalNAcβ1-4(Neu5Acα2-3)Galβ1-4Glcβ
(OligoTech; Cat# GLY103-NAc-sp3-Bt)
Globo H: Fucα1-2Galβ1-3GalNAcβ1-3Galα1-4Galβ1-4Glcβ
SSEA3:Galβ1-3GalNAcβ1-3Galα1-4Galβ1-4Glcβ
SSEA4 :Neu5Acα2-3Galβ1-3GalNAcβ1-3Galα1-4Galβ1-4Glcβ
Tn:α-GalNAc
(GlycoTech; Cat# 01-010)
sTn:NeuAcα2-6GalNAcα
(GlycoTech; Cat# 01-059)
Sialic acid (mono):α-Neu5Ac
(GlycoTech; Cat# 01-012)
sLewis A:NeuAcα2-3Galβ1-3(Fucα1-4)GlcNAcβ
(GlycoTech; Cat# 01-044)
sLewis X:NeuAcα2-3Galβ1-4(Fucα1-3)GlcNAcβ
(GlycoTech; Cat# 01-045)
Lewis Y:Fucα1-2Galβ1-4(Fucα1-3)GlcNAcβ
(GlycoTech; Cat# 01-043)

Plate Coating 96-well commercial available Streptavidin HBC coated black plate (ThermoSci, Cat #15503) was washed with 200 µL/per well Wash Buffer (Sigma, Cat #P5493) once. Biotinylated sugars stock was diluted to 1 ng/mL in 1×PBS. Volumes of diluted biotinylated sugars were added to test plate (50 µL/well; 50 ng/well). Test plate was incubated at room temperature for 2 hours. Wells were washed once with 200 µL Wash Buffer. 200 µL of SuperBlock were added to each well and incubated at room temperature for 1 hour.

Primary Antibody

TABLE 8

| Exemplary primary antibodies | |
|---|---|
| Clone name | Isotype control name |
| 1G1s | Purified Mouse IgG$_{2b}$ (Biolegend, Cat #400302) |
| 1J1s | Purified Mouse IgG$_1$ (Biolegend, Cat #401402) |
| 2F20s | Purified Mouse IgG$_{2a}$ (Biolegend, Cat #401502) |
| Commercial SSEA-4 Antibody (MC-813-70) (Biolegend; Cat#330402) | Purified Mouse IgG$_3$ (Biolegend, Cat #401302) |

After incubation, wells were aspirated and washed once with 200 µL Wash Buffer. 50 µL of 2.5 µg/mL primary antibodies were added to individual plates. Test Plates were covered, labeled, and incubated at room temperature for approximately 1 hour. After incubation, wells were aspirated and washed four times with 200 µL Wash Buffer.

Secondary Antibody.

50 µL of Secondary Antibody Solution was pipetted into each well. Plates were covered, labeled, and incubated at room temperature for approximately 45 minutes. After incubation, Secondary Antibody Solution was aspirated from all wells and all wells washed five times with 200 µL Wash Buffer.

100 µL Substrate Solution (ThermoSci, Cat #PIE37074) was pipetted into each well and incubated at room temperature for 1 to 5 minutes. Plates were read with ELISA plate reader (Molecular Devices, SpectraMax L) at 470 nm.

Data Analysis

Data were analyzed statistically using GraphPad Prism 6 Software. Mean and SD were calculated from the triplicate results.

Figure 12:
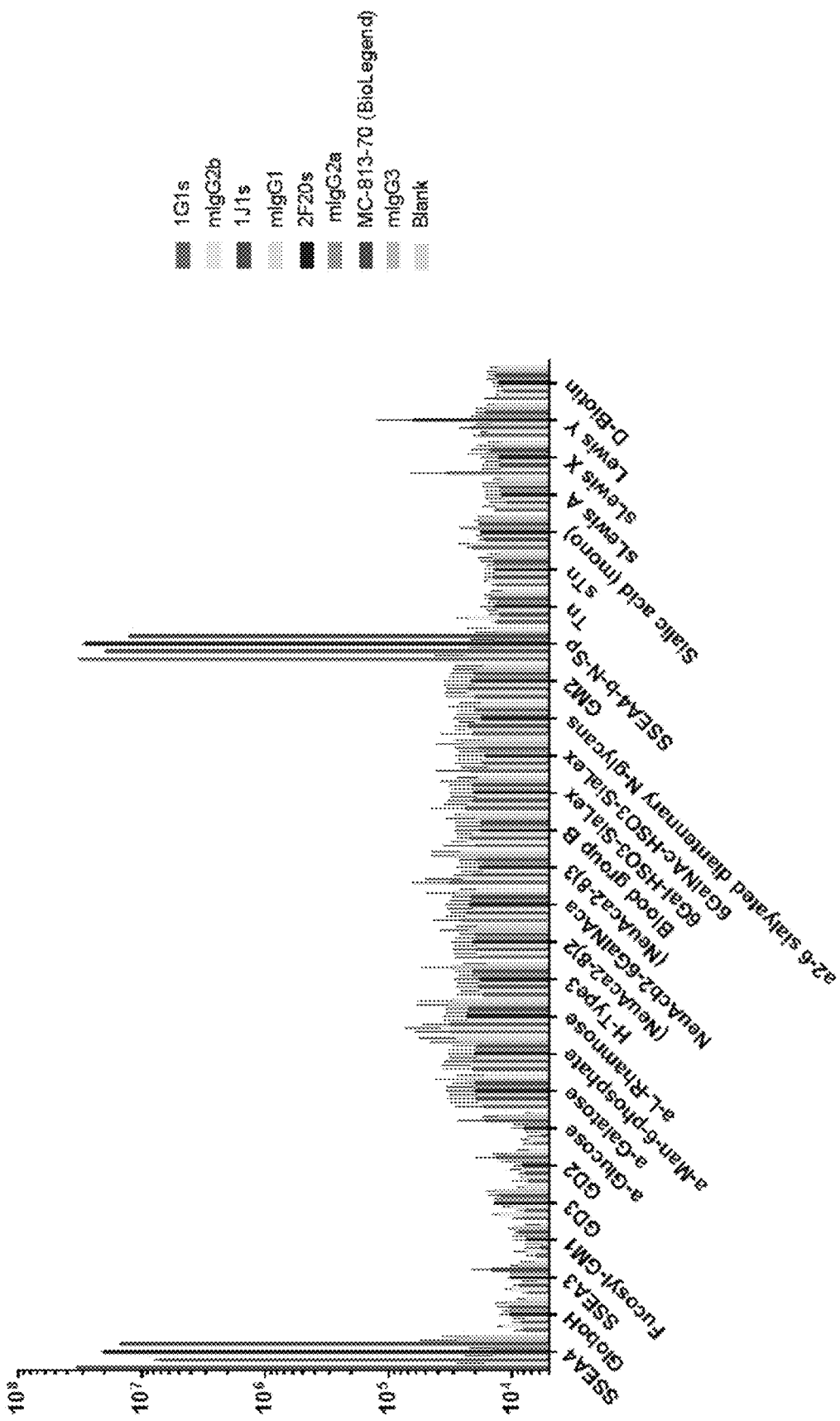
FIG. 12 shows cross reactivity test with biotinylated sugars by the chemiluminescent sandwich ELISA analysis.

FIG. 12 shows the ELISA affinity assay result of SSEA-4 antibodies. Exemplary SSEA-4 antibodies, including 1G1s, Ms, 2F20s, and commercial MC-813-70, showed minimal interaction with other tumor associated sugars and are specific with SSEA-4 antigens (SSEA4 and SSEA4-b-N-Sp). It showed binding specificity of SSEA4-antibodies in this invention.

Example 6: Measurement of the Anti-Tumor Activity of the Exemplary Antibody Combined with Globo H Antibody in Nude Mice In a xenograft tumor model of human pancreatic adenocarcinoma, HPAC cells were subcutaneously (s.c.) implanted into BALB/c male nude mice and test articles were administered at 0.1 mg/kg, 10 mg/kg or combination with 0.1 mg/kg of both antibodies by intraperitoneal (i.p.) injection twice weekly for 5 weeks starting when the average tumor size reached 50-120 mm$^3$. The tumor size was then monitored and recorded twice weekly for 37 days. Mortality, body weight, and signs of overt animal toxicity were also recorded twice weekly for 37 days. Tumor growth was calculated as T/C (treatment/control)×100%.

Test Substances and Dosing Pattern

Test substances were prepared at 1 or 1.03 mg/mL in liquid form. Test substances were freshly prepared each day before dosing by diluting stocks solutions with sodium citrate buffer (25 mM sodium citrate and 100 mM NaCl, pH6.5) to obtain the designated dosing concentration (0.01 mg/mL or 1 mg/mL). Test substances were administered intraperitoneally at a dosing volume at 10 mL/kg twice weekly for 5 weeks.

Washington, D.C., 2011) in our AAALAC-accredited laboratory animal facility. In addition, the animal care and use protocol was reviewed and approved by the IACUC at Pharmacology Discovery Services Taiwan Ltd.

Chemicals

DMEM/F12 medium (Invitrogen, USA), Epidermal growth factor (R&D Systems, USA), Fetal bovine serum (Invitrogen, USA), Insulin (Sigma, USA), Hydrocortisone (Sigma, USA) and Penicillin/streptomycin solution (Invitrogen, USA).

Equipment

Animal cage (Tecniplast, Italy), Beaker 1000 mL (Kimax, USA), Calipers (Mitutoyo, Japan), Class II biological safety cabinet (NuAire, USA), Centrifuge 5810 R (Eppendorf, Germany), μ incubator (Forma Scientific Inc., USA), Individually ventilated cages (IVC, 36 Mini Isolator system) (Tecniplast, Italy), Mouse scale #Z-40 (Taconic, USA), Stainless forceps (Klappenecker, Germany) and Vertical laminar flow (Tsao-Hsin, Taiwan).

Methods

BALB/c nude male mice at 6-7 weeks of age and weighing 18-22 g were used. Human pancreatic adenocarcinoma tumor cells HPAC (ATCC CRL-2119, 1.0×10$^6$ in 0.1 mL) were injected subcutaneously into the right flank of the

TABLE 9

The exemplary types of formulation.

| Test Compound | Vehicle | Solubility[a] | Color | Light Protection[b] | Temperature[c] | Formulation mg/mL |
|---|---|---|---|---|---|---|
| 1J1s | Sodium citrate buffer, pH 6.5 | S | Colorless | N | 4° C. | 0.01 |
| 1J1s | Sodium citrate buffer, pH 6.5 | S | Colorless | N | 4° C. | 1 |
| Globo H-2C2 | Sodium citrate buffer, pH 6.5 | S | Colorless | N | 4° C. | 0.01 |
| Globo H-2C2 | Sodium citrate buffer, pH 6.5 | S | Colorless | N | 4° C. | 1 |
| 1J1s + 2C2 | Sodium citrate buffer, pH 6.5 | S | Colorless | N | 4° C. | 0.01 + 0.01 |

[a] This is based upon visual observation S: soluble; SS: slightly soluble; I: insoluble (suspension or precipitation)
[b] Y: formula is kept in tube or vial with brown color, or covered with aluminum foil. N: no protection from light
[c] RT: prepared fresh and stored between 20-25° C. 4° C.: prepared fresh and stored in the refrigerator or kept on ice.

Cell Line

HPAC tumor cell line (ATCC CRL-2119, human pancreatic adenocarcinoma) was prepared and cultured at Eurofins Panlabs Taiwan Ltd. before subcutaneous implantation at 0.1 mL of 1×10$^6$ cells/mouse into the right flank of BALB/c male nude mice.

Animals

BALB/c male nude mice, 6-7 weeks of age, weighing 18-22 g were obtained from BioLasco Taiwan (under Charles River Laboratories Licensee). All animals were maintained in a well-controlled temperature (20-24° C.) and humidity (30-70%) environment with 12 hours light/dark cycles. Free access to standard lab diet [MFG (Oriental Yeast Co., Ltd., Japan)] and autoclaved tap water were granted. All aspects of this study including housing, experimentation, and animal disposal were performed in general accordance with the "Guide for the Care and Use of Laboratory Animals: Eighth Edition" (National Academies Press, animals. The animals were subsequently divided into 6 groups, consisting of 8 animals in each group. The administration of test substances and the vehicle was initiated when the average tumor size reached 50-120 mm$^3$ (set as Day 1). Test substances (according to the dosing in Table X) were prepared freshly prior to each dosing. Test substances and the vehicle were administered twice weekly by intraperitoneal injection for 5 weeks. Tumor size, body weight, and mortality were recorded twice weekly for 37 days prior to administrations of test substances or the vehicle.

Tumor volume (mm$^3$) was determined according to the ellipsoid formula: length×(width)×0.5. Tumor growth (T/C) was calculated using the following formula: T/C=(Tn)/(Cn)×100%, where C1 (Cn) is the tumor volume of day n in the control group, and T1 (Tn) is the tumor volume of day n in the treated group. T/C value ≤42% was considered significant antitumor activity.

Results

TABLE 10

Tumor, Xenograft, Pancreas, HPAC, in Nude Mice

| Gr. | Treatment | Dose (mg/kg) (Route) | No. | Day 1 | Day 4 | Day 8 | Day 11 | Day 15 | Day 18 | Day 22 | Day 25 | Day 29 | Day 32 | Day 37 |
|---|---|---|---|---|---|---|---|---|---|---|---|---|---|---|
| | | | | | | | Tumor Volume (mm$^3$) | | | | | | | |
| 1 | Vehicle (25 mM sodium citrate, pH 6.5 + 100 mM NaCl) | 10 mL/kg × 10 (Twice weekly) (IP) | 1 | 78 | 139 | 228 | 230 | 293 | 336 | 519 | 514 | 612 | 778 | 940 |
| | | | 2 | 79 | 150 | 233 | 259 | 390 | 457 | 607 | 733 | 999 | 1274 | 1535 |
| | | | 3 | 133 | 216 | 421 | 552 | 630 | 928 | 1183 | 1408 | 1615 | 2032 | 2150 |
| | | | 4 | 56 | 131 | 162 | 214 | 214 | 313 | 392 | 498 | 603 | 634 | 780 |
| | | | 5 | 72 | 146 | 243 | 259 | 322 | 380 | 515 | 658 | 827 | 952 | 1175 |
| | | | 6 | 72 | 148 | 186 | 237 | 327 | 395 | 449 | 675 | 694 | 671 | 844 |
| | | | 7 | 56 | 117 | 181 | 211 | 282 | 395 | 507 | 642 | 725 | 687 | 811 |
| | | | 8 | 55 | 108 | 168 | 244 | 277 | 315 | 377 | 482 | 583 | 652 | 716 |
| | | | Mean | 75 | 144 | 228 | 276 | 342 | 440 | 569 | 701 | 832 | 960 | 1119 |
| | | | SEM | 9 | 12 | 30 | 40 | 45 | 72 | 92 | 106 | 122 | 171 | 175 |
| 2 | 1J1s | 0.1 mg/kg × 10 (Twice weekly) (IP) | 1 | 79 | 144 | 205 | 231 | 285 | 419 | 505 | 577 | 767 | 856 | 977 |
| | | | 2 | 110 | 231 | 282 | 402 | 447 | 624 | 897 | 1126 | 1391 | 1700 | 2190 |
| | | | 3 | 61 | 133 | 162 | 202 | 303 | 341 | 466 | 550 | 652 | 678 | 801 |
| | | | 4 | 111 | 209 | 274 | 344 | 354 | 499 | 640 | 744 | 826 | 972 | 1172 |
| | | | 5 | 58 | 96 | 139 | 155 | 173 | 234 | 234 | 236 | 341 | 455 | 557 |
| | | | 6 | 77 | 111 | 169 | 205 | 276 | 356 | 451 | 495 | 702 | 760 | 938 |
| | | | 7 | 72 | 124 | 173 | 198 | 296 | 371 | 431 | 492 | 633 | 745 | 811 |
| | | | 8 | 45 | 86 | 144 | 160 | 171 | 243 | 244 | 241 | 348 | 490 | 534 |
| | | | Mean | 77 | 142 | 194 | 237 | 288 | 386 | 484 | 558 | 708 | 832 | 998 |
| | | | SEM | 8 | 18 | 20 | 31 | 32 | 46 | 76 | 101 | 116 | 138 | 186 |
| | | | % T/C | 103 | 94 | 76 | 80 | 79 | 85 | 82 | 77 | 83 | 85 | 88 |
| 3 | 1J1s | 10 mg/kg × 10 (Twice weekly) (IP) | 1 | 64 | 96 | 145 | 150 | 205 | 289 | 292 | 314 | 381 | 505 | 583 |
| | | | 2 | 99 | 206 | 308 | 309 | 429 | 551 | 568 | 657 | 922 | 958 | 1151 |
| | | | 3 | 66 | 113 | 141 | 148 | 162 | 231 | 285 | 314 | 452 | 452 | 606 |
| | | | 4 | 102 | 154 | 240 | 287 | 303 | 416 | 446 | 463 | 654 | 768 | 952 |
| | | | 5 | 93 | 146 | 231 | 311 | 461 | 540 | 654 | 720 | 883 | 1014 | 1172 |
| | | | 6 | 68 | 99 | 162 | 189 | 222 | 267 | 435 | 489 | 556 | 658 | 787 |
| | | | 7 | 48 | 75 | 140 | 174 | 203 | 322 | 316 | 361 | 444 | 585 | 600 |
| | | | 8 | 74 | 113 | 161 | 243 | 264 | 318 | 395 | 449 | 581 | 717 | 919 |
| | | | Mean | 77 | 125 | 191 | 226 | 281 | 367 | 424 | 471 | 609 | 707 | 846 |
| | | | SEM | 7 | 15 | 22 | 25 | 39 | 43 | 47 | 53 | 71 | 71 | 85 |
| | | | % T/C | 103 | 70 | 75 | 74 | 76 | 79 | 70 | 63 | 70 | 71 | 74 |
| 4 | Globo H-2C2 | 0.1 mg/kg × 10 (Twice weekly) (IP) | 1 | 92 | 179 | 262 | 415 | 573 | 797 | 864 | 1153 | 1568 | 2237 | 2470 |
| | | | 2 | 59 | 96 | 117 | 119 | 156 | 161 | 166 | 246 | 284 | 388 | 425 |
| | | | 3 | 62 | 115 | 135 | 174 | 174 | 269 | 275 | 291 | 447 | 533 | 625 |
| | | | 4 | 63 | 129 | 165 | 236 | 313 | 335 | 461 | 593 | 764 | 890 | 1076 |
| | | | 5 | 46 | 73 | 108 | 108 | 101 | 127 | 139 | 200 | 256 | 321 | 388 |
| | | | 6 | 125 | 185 | 323 | 401 | 711 | 779 | 879 | 1109 | 1460 | 1766 | 2158 |
| | | | 7 | 77 | 143 | 202 | 245 | 337 | 441 | 537 | 645 | 910 | 1181 | 1305 |
| | | | 8 | 80 | 108 | 137 | 150 | 192 | 285 | 285 | 346 | 441 | 510 | 622 |
| | | | Mean | 76 | 129 | 181 | 231 | 320 | 399 | 451 | 573 | 766 | 978 | 1134 |
| | | | SEM | 9 | 14 | 27 | 42 | 77 | 92 | 103 | 134 | 182 | 248 | 282 |
| | | | % T/C | 101 | 77 | 69 | 77 | 91 | 88 | 76 | 79 | 91 | 102 | 101 |
| 5 | Globo H-2C2 | 10 mg/kg × 10 (Twice weekly) (IP) | 1 | 89 | 129 | 164 | 192 | 282 | 292 | 309 | 388 | 467 | 578 | 695 |
| | | | 2 | 80 | 161 | 207 | 251 | 283 | 363 | 433 | 461 | 602 | 711 | 790 |
| | | | 3 | 39 | 76 | 123 | 123 | 161 | 196 | 216 | 245 | 313 | 409 | 445 |
| | | | 4 | 93 | 154 | 278 | 283 | 400 | 658 | 780 | 946 | 1248 | 1523 | 1766 |
| | | | 5 | 80 | 122 | 163 | 182 | 213 | 310 | 320 | 321 | 346 | 383 | 428 |
| | | | 6 | 55 | 89 | 166 | 166 | 202 | 233 | 285 | 317 | 476 | 478 | 578 |
| | | | 7 | 85 | 205 | 243 | 406 | 437 | 575 | 617 | 684 | 780 | 1079 | 2025 |
| | | | 8 | 80 | 119 | 142 | 160 | 210 | 292 | 317 | 406 | 499 | 639 | 846 |
| | | | Mean | 75 | 132 | 186 | 220 | 274 | 365 | 410 | 471 | 591 | 725 | 947 |
| | | | SEM | 7 | 15 | 19 | 32 | 35 | 58 | 68 | 82 | 107 | 138 | 215 |
| | | | % T/C | 100 | 83 | 73 | 72 | 75 | 79 | 68 | 63 | 68 | 73 | 84 |
| 6 | 1J1s + Globo H-2C2 | 0.1 mg/kg × 10 (Twice weekly) (IP) + 0.1 mg/kg × 10 (Twice | 1 | 77 | 104 | 154 | 155 | 184 | 252 | 275 | 324 | 456 | 442 | 599 |
| | | | 2 | 92 | 171 | 198 | 234 | 300 | 401 | 407 | 525 | 698 | 929 | 936 |
| | | | 3 | 76 | 104 | 166 | 164 | 156 | 233 | 256 | 256 | 310 | 303 | 363 |
| | | | 4 | 77 | 131 | 139 | 184 | 205 | 308 | 303 | 345 | 437 | 446 | 573 |
| | | | 5 | 115 | 189 | 288 | 366 | 432 | 682 | 878 | 877 | 1242 | 1689 | 2025 |
| | | | 6 | 43 | 105 | 155 | 196 | 205 | 247 | 347 | 344 | 403 | 462 | 473 |
| | | | 7 | 53 | 104 | 106 | 111 | 141 | 181 | 258 | 258 | 269 | 269 | 381 |
| | | | 8 | 68 | 99 | 146 | 146 | 183 | 240 | 253 | 337 | 381 | 411 | 589 |

TABLE 10-continued

Tumor, Xenograft, Pancreas, HPAC, in Nude Mice

| Gr. | Treatment | Dose (mg/kg) (Route) | No. | Tumor Volume (mm³) | | | | | | | | | | |
|---|---|---|---|---|---|---|---|---|---|---|---|---|---|---|
| | | | | Day 1 | Day 4 | Day 8 | Day 11 | Day 15 | Day 18 | Day 22 | Day 25 | Day 29 | Day 32 | Day 37 |
| | | weekly) (IP) | Mean | 75 | 126 | 169 | 195 | 226 | 318 | 372 | 408 | 525 | 619 | 742 |
| | | | SEM | 8 | 12 | 19 | 28 | 34 | 57 | 75 | 73 | 112 | 169 | 194 |
| | | | % T/C | 100 | 74 | 61 | 60 | 57 | 67 | 60 | 53 | 59 | 61 | 64 |

Test substances were administered intraperitoneally twice weekly for 5 weeks. Tumor size was measured and recorded twice weekly for 37 days. Tumor growth was calculated as T/C (treatment/control) × 100%.
T/C value ≤42% was considered significant antitumor activity. In addition, two-way ANOVA followed by Bonferroni test was applied to ascertain the statistically significant difference compared to Group 1 (Vehicle, PBS) at * P < 0.05.

Figure 13:
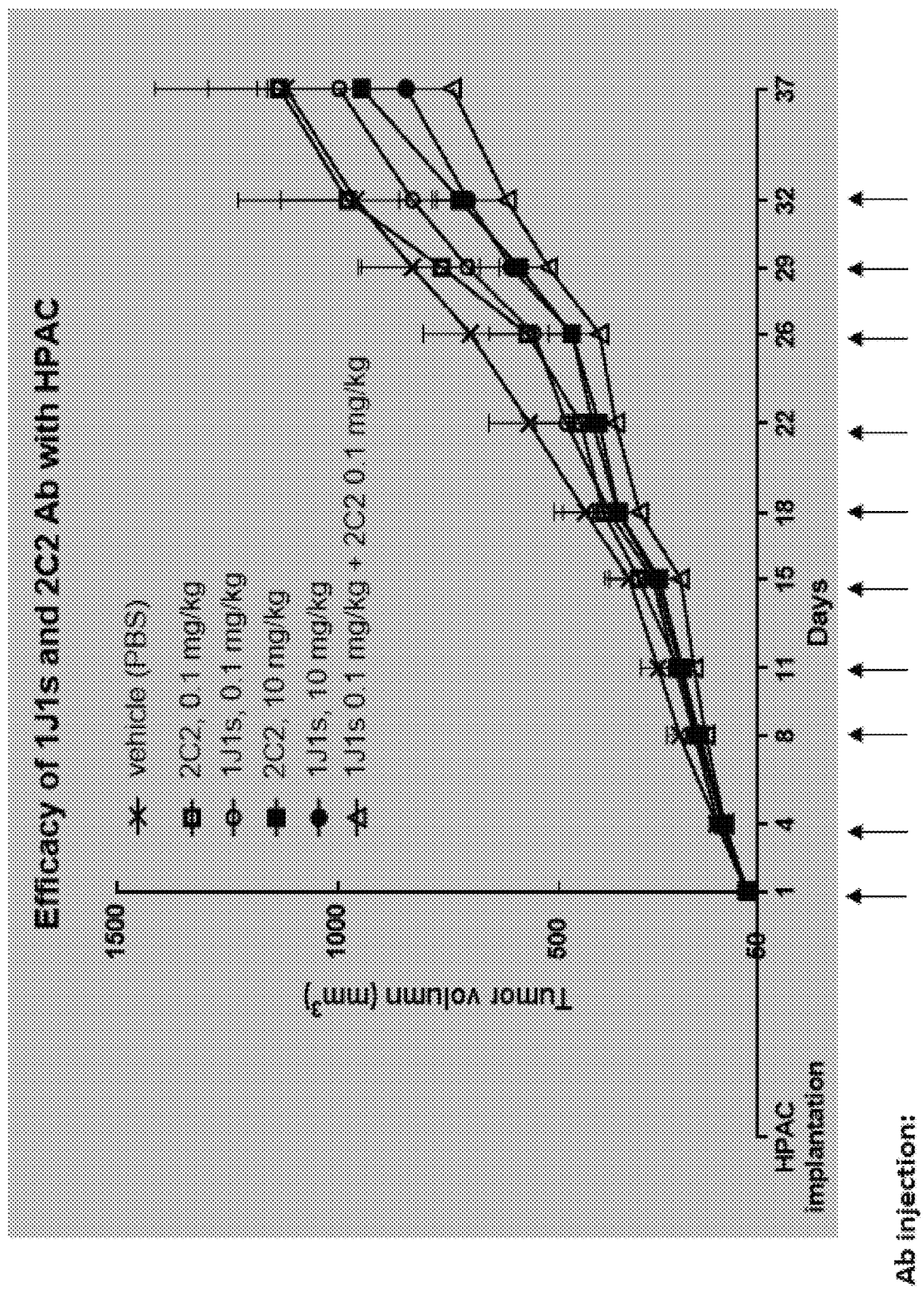
FIG. 13 shows a graph of measurements of tumor volume during the course of antibody combination injections over 37 days. The effect of antibodies 2C2 (Anti-Globo H) and 1J1s (Anti-SSEA4) were measured on HPAC tumors.

FIG. 13 showed the photos of Nude Mice with administering different test compounds for 37 Days. The tumor growth inhibition (TGI (%)=($V_{control}$-$V_{test}$)/($V_{control}$-$V_{original}$)*100) at the end of this study were calculated as 10.8% of 0.1 mg/kg Ms, 24.4% of 10 mg/kg Ms, 15.4% of 10 mg/kg 2C2 (0.1 mg/kg 2C2 didn't showed inhibition ability of HPAC). However, 0.1 mg/kg Ms combined with 0.1 mg/kg 2C2 showed 33.7% tumor growth inhibition, even higher than 100-fold dosing of treatment with 1J1s or 2C2 alone.

While specific aspects of the invention have been described and illustrated, such aspects should be considered illustrative of the invention only and not as limiting the invention as construed in accordance with the accompanying claims. All publications and patent applications cited in this specification are herein incorporated by reference in their entirety for all purposes as if each individual publication or patent application were specifically and individually indicated to be incorporated by reference in its entirety for all purposes. Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed is:

1. An antibody, or an antigen-binding fragment thereof, comprising:
   a heavy chain variable domain (VH) and
   a light chain variable domain (VL),
   wherein said heavy chain variable domain (VH) comprises heavy chain CDRs comprising the amino acid sequences of SEQ ID NOS: 13, 15 and 17, and
   wherein said light chain variable domain (VL) comprises light chain CDRs comprising the amino acid sequences of SEQ ID NOS: 6, 8 and 10;
   wherein the antibody or the antigen-binding fragment binds SSEA-4.

2. The antibody or antigen-binding fragment thereof of claim 1, wherein the antibody or antigen-binding fragment thereof is selected from: (a) a whole immunoglobulin molecule; (b) an scFv; (c) a Fab fragment; (d) an F(ab')2; or (e) a disulfide linked Fv.

3. The antibody, or an antigen-binding fragment thereof of claim 1, wherein the antibody is a humanized antibody.

4. The antibody of claim 3, wherein the antibody is an IgG or IgM.

5. A chimeric antigen receptor (CAR) specific for SSEA-4, wherein an antibody, or an antigen-binding SSEA-4 recognition domain comprises the antibody or the antigen-binding fragment thereof of claim 3.

6. The antibody of claim 5, wherein the CAR domain comprises a transmembrane domain and an intracellular signaling domain, wherein the transmembrane domain comprises a sequence of the transmembrane domains of CD8 and/or CD28; and wherein the intracellular signaling domain comprises a sequence of the intracellular signaling domains of one or more of CD27, CD28, CD137, OX40, ICOS and CD3zeta.

7. A pharmaceutical composition, comprising:
   the antibody or antigen-binding fragment thereof of claim 3, and at least one pharmaceutically acceptable carrier.

8. The pharmaceutical composition of claim 7, further comprising at least one additional therapeutic agent.

9. An antibody drug conjugate (ADC) specific for SSEA-4 comprising the antibody or antigen-binding fragment thereof of claim 3, and further comprising a cytotoxic agent, wherein the cytotoxic agent is covalently conjugated to the antibody or the antigen-binding fragment by a linker.

10. A method of treating cancer, the method comprising administering in need thereof an effective amount of the ADC of claim 9.

11. The method of claim 10, wherein the cancer is selected from the group consisting of breast cancer, lung cancer, esophageal cancer, rectal cancer, biliary cancer, liver cancer, buccal cancer, gastric cancer, colon cancer, nasopharyngeal cancer, kidney cancer, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer, basal cell carcinoma, squamous cell carcinoma, melanoma, or brain tumor.

12. An SSEA-4 binding antibody, or an antigen-binding fragment thereof, comprising:
    a heavy chain variable domain (VH) and a light chain variable domain (VL), wherein said heavy chain variable domain (VH) comprises an amino acid sequence of at least about 95% sequence homology to the amino acid sequence set forth in SEQ ID NO: 3 and heavy chain CDRs comprising the amino acid sequence of SEQ ID NOS: 13, 15 and 17, and wherein said light chain variable domain (VL) comprises an amino acid sequence of at least about 95% sequence homology to the amino acid sequence set forth in SEQ ID NO: 4 and light chain CDRs comprising the amino acid sequences of SEQ ID NOS: 6, 8 and 10.

13. An SSEA-4 antibody or binding fragment thereof, wherein the antibody or binding fragment thereof comprises VH selected from SEQ ID No: 3, and VL selected from SEQ ID NO: 4.

14. The chimeric antigen receptor (CAR) of claim 5 comprising the heavy chain variable domain (VH) selected from SEQ ID NO: 3 and the light chain variable domain (VL) selected from SEQ ID NO: 4.

15. An antibody, or an antigen-binding fragment thereof, produced by the hybridoma designated as 1J1s deposited under ATCC Accession Number PTA-122679.

16. A hybridoma designated as 1J1s deposited under ATCC Accession Number PTA-122679.

17. A method of treating cancer in a subject, the method comprising administering to a subject in need thereof an effective amount of the pharmaceutical composition comprising the antibody of claim 1.

18. The method of claim 17, wherein the cancer is selected from the group consisting of breast cancer, lung cancer, esophageal cancer, rectal cancer, biliary cancer, liver cancer, buccal cancer, gastric cancer, colon cancer, nasopharyngeal cancer, kidney cancer, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer, basal cell carcinoma, squamous cell carcinoma, melanoma, or brain tumor.

19. The method of claim 17, wherein the subject is human.

20. A method for inhibiting the proliferation of cancer cells, comprising the administering of an effective amount of the pharmaceutical composition according to claim 7 to a subject in need thereof, wherein the proliferation of cancer cells is inhibited.

21. The method of claim 20, wherein the cell is cancer stem cell.

22. A method for cancer diagnosis in a subject, comprising:
    (a) obtaining a body fluid sample or a cell sample from a subject,
    (b) contacting the sample with the antibody of claim 1 that can detect expression of;
    (c) assaying the binding of the antibody to the cell or the sample; and
    (d) assessing the cancer status of the subject in an assay by measuring and comparing the level of antibody binding with a normal control to determine the presence of the cancer in the subject.

23. A method for treating a human patient by monitoring prognosis of tumors in the patient, wherein the method comprising:
    (a) obtaining a body fluid sample or a cell/tissue sample from the patient;
    (b) contacting the sample with the antibody of claim 1 that can detect SSEA-4;
    (c) assaying the level of binding of the antibody to the cell or the cell/tissue sample;
    (d) measuring and comparing the level of the markers in the test sample with the level in a reference sample;
    (e) determining the stage and/or prognosis of tumors in the patient based on the determination in step (d); and
    (f) adjusting treatment planning for immunotherapy of said patient based on (e).

24. The method of claim 22, wherein the sample is selected from a group consisting of serum, blood, plasma, cells, cell medium, saliva, urine, lymph node fluid, tumor biopsy or tissue culture.

25. A method of imaging a subject comprising:
    (a) administering an effective amount of the antibody of claim 1, wherein the antibody is conjugated to an imaging agent; and
    (b) detecting and determining the imaging agent in the subject; and
    (c) generating and displaying the image on a display.

26. The method of claim 25, wherein the imaging agent is a fluorophore, a dye, an MRI contrast agent or a radionuclide.

27. The method of claim 25, wherein the subject has a cancer, the method further defined as a method of detecting a cancer metastasis.

28. The method of claim 25, wherein the subject is human.

29. The method of claim 22, wherein the assay is an antibody based assay or an array.

30. A bi-specific antibody or antigen-binding fragment thereof of, comprising a first binding domain of the antibody or antigen-binding fragment of claim 1 that specifically binds to SSEA-4 and a second binding domain that specifically binds to T cell surface antigens.

31. The bi-specific antibody or antigen-binding fragment of claim 30, wherein the T cell surface antigens comprising CD2, CD3, CD4, CD5, CD6, CD8, CD28, CD40L or CD44.

32. A method of treating cancer, the method comprising administering in need thereof an effective amount of the bi-specific antibody or antigen-binding fragment of claim 30.

33. The method of claim 32, wherein the cancer is selected from the group consisting of breast cancer, lung cancer, esophageal cancer, rectal cancer, biliary cancer, liver cancer, buccal cancer, gastric cancer, colon cancer, nasopharyngeal cancer, kidney cancer, prostate cancer, ovarian cancer, cervical cancer, endometrial cancer, pancreatic cancer, testicular cancer, bladder cancer, head and neck cancer, oral cancer, neuroendocrine cancer, adrenal cancer, thyroid cancer, bone cancer, skin cancer, basal cell carcinoma, squamous cell carcinoma, melanoma, or brain tumor.

\* \* \* \* \*

SEQUENCE LISTING

```
<160> NUMBER OF SEQ ID NOS: 54

<210> SEQ ID NO 1
<211> LENGTH: 351
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
caggtgcagc tgaaggagtc aggacctggc ctggtggcgc cctcacagag cctgtccatc      60
acttgcactg tctctgggtt ttcattaatc agctatggtg tagactgggt tcgccagcct     120
ccaggaaagg gtctggagtg gctgggagta atatgggtg gtggaaatac aaattataat     180
tcatctctca tgtccagact gagcatcagc aaagacaact ccaagagcca agttttctta     240
aaaatgaaca gtctgcaaac tgatgacaca gccatgtact actgtgccaa aactgggacc     300
ggatatgctt tggagtactg gggtcaagga acctcagtca ccgtctcctc c              351

<210> SEQ ID NO 2
<211> LENGTH: 321
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 2
gaaaatgttc tcacccagtc tccagcaatc atgtctgcat ctccagggga aaaggtcacc      60
atgacctgca gtgccaggtc aagtgtaagt tacatgcact ggtaccagca gaagtcaacc     120
gcctccccca aactctggat ttatgacaca tccaaactgg cttctggagt cccaggtcgc     180
ttcagtggca gtgggtctgg aaactcttac tctctcacga tcagcagcat ggaggctgaa     240
```

```
gatgttgcca cttattactg ttttcaggcg agtgggtacc cgctcacgtt cggtgctggg    300
accaagctgg agctgaaacg g                                              321
```

<210> SEQ ID NO 3
<211> LENGTH: 117
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 3

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ile Ser Tyr
            20                  25                  30

Gly Val Asp Trp Val Arg Gln Pro Pro Gly Lys Gly Leu Glu Trp Leu
        35                  40                  45

Gly Val Ile Trp Gly Gly Gly Asn Thr Asn Tyr Asn Ser Ser Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys Thr Gly Thr Gly Tyr Ala Leu Glu Tyr Trp Gly Gln Gly Thr Ser
            100                 105                 110

Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 4

Glu Asn Val Leu Thr Gln Ser Pro Ala Ile Met Ser Ala Ser Pro Gly
1               5                   10                  15

Glu Lys Val Thr Met Thr Cys Ser Ala Arg Ser Ser Val Ser Tyr Met
            20                  25                  30

His Trp Tyr Gln Gln Lys Ser Thr Ala Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Ala Ser Gly Tyr Pro Leu Thr
                85                  90                  95

Phe Gly Ala Gly Thr Lys Leu Glu Leu Lys Arg
            100                 105

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic Polypeptide

<400> SEQUENCE: 5

Glu Asn Val Leu Thr Gln Ser Pro Ala Ile Met Ser Ala Ser Pro Gly
1               5                   10                  15

Glu Lys Val Thr Met Thr Cys
            20

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 6

Ser Ala Arg Ser Ser Val Ser Tyr Met His
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 7

Trp Tyr Gln Gln Lys Ser Thr Ala Ser Pro Lys Leu Trp Ile Tyr
1               5                   10                  15

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 8

Asp Thr Ser Lys Leu Ala Ser
1               5

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 9

Gly Val Pro Gly Arg Phe Ser Gly Ser Gly Ser Gly Asn Ser Tyr Ser
1               5                   10                  15

Leu Thr Ile Ser Ser Met Glu Ala Glu Asp Val Ala Thr Tyr Tyr Cys
            20                  25                  30

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 10

```
Phe Gln Ala Ser Gly Tyr Pro Leu Thr
1               5
```

```
<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 11

Phe Gly Ala Gly Thr Lys Leu Glu Leu Lys Arg
1               5                   10
```

```
<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 12

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25
```

```
<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 13

Gly Phe Ser Leu Ile Ser Tyr Gly Val Asp
1               5                   10
```

```
<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 14

Trp Val Arg Gln Pro Pro Gly Lys Gly Leu Glu Trp Leu Gly
1               5                   10
```

```
<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 15

Val Ile Trp Gly Gly Gly Asn Thr Asn Tyr Asn Ser Ser Leu Met Ser
1               5                   10                  15
```

```
<210> SEQ ID NO 16
```

```
<211> LENGTH: 32
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 16

Arg Leu Ser Ile Ser Lys Asp Asn Ser Lys Ser Gln Val Phe Leu Lys
1               5                   10                  15

Met Asn Ser Leu Gln Thr Asp Asp Thr Ala Met Tyr Tyr Cys Ala Lys
            20                  25                  30

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 17

Thr Gly Thr Gly Tyr Ala Leu Glu Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 18

Trp Gly Gln Gly Thr Ser Val Thr Val Ser Ser
1               5                   10

<210> SEQ ID NO 19
<211> LENGTH: 351
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 19
caggtgcagc tgaaggagtc aggacctggc ctggtggcgc cctcacagag cctgtccatc      60
acttgtactg tctctgggtt ttcattaagc agctatggtg tagactgggt tcgccaacct     120
ccaggaaagg gtctggagtg gctgggagta atatgggtg gtggaagcat aaattataat      180
tcagctctca tgtccagact gagcatcagc aaagacaatt ccaagagcca aattttctta     240
aaaatgaaca gtctgcaaac tgatgacaca gccatatact actgtaccac acatgaggat     300
tacggtcctt ttgcttactg gggccaaggg actctggtca ctgtctctgc a              351

<210> SEQ ID NO 20
<211> LENGTH: 321
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 20
caaattgttc tctcccagtc tccagcaatc ctgtctgcat ctccagggga gaaggtcaca      60
```

```
atgacttgca gggccagctc aagtgtaagt tacatgcact ggtaccagca gaagccagga    120
tcctccccca atcctggat ttatgccaca tccaacctgg cttctggagt ccctgctcgc     180
ttcagtggca gtgggtctgg gacctcttac tctctcacaa tcagcagagt ggaggctgaa    240
gatgctgcca cttattactg ccagcagtgg ggtagttacc cgtggacgtt cggtggaggc    300
accaagctgg aaatcaaacg g                                              321
```

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 21

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Ser Tyr
            20                  25                  30

Gly Val Asp Trp Val Arg Gln Pro Pro Gly Lys Gly Leu Glu Trp Leu
        35                  40                  45

Gly Val Ile Trp Gly Gly Ser Ile Asn Tyr Asn Ser Ala Leu Met
    50                  55                  60

Ser Arg Leu Ser Ile Ser Lys Asp Asn Ser Lys Ser Gln Ile Phe Leu
65                  70                  75                  80

Lys Met Asn Ser Leu Gln Thr Asp Asp Thr Ala Ile Tyr Tyr Cys Thr
                85                  90                  95

Thr His Glu Asp Tyr Gly Pro Phe Ala Tyr Trp Gly Gln Gly Thr Leu
            100                 105                 110

Val Thr Val Ser Ala
        115

<210> SEQ ID NO 22
<211> LENGTH: 107
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 22

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Ser Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Gly Ser Tyr Pro Trp Thr
                85                  90                  95

Phe Gly Gly Gly Thr Lys Leu Glu Ile Lys Arg
            100                 105

<210> SEQ ID NO 23

```
<211> LENGTH: 23
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 23

Gln Ile Val Leu Ser Gln Ser Pro Ala Ile Leu Ser Ala Ser Pro Gly
1               5                   10                  15

Glu Lys Val Thr Met Thr Cys
            20

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 24

Arg Ala Ser Ser Ser Val Ser Tyr Met His
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 25

Trp Tyr Gln Gln Lys Pro Gly Ser Ser Pro Lys Ser Trp Ile Tyr
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 26

Ala Thr Ser Asn Leu Ala Ser
1               5

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 27

Gly Val Pro Ala Arg Phe Ser Gly Ser Gly Ser Gly Thr Ser Tyr Ser
1               5                   10                  15

Leu Thr Ile Ser Arg Val Glu Ala Glu Asp Ala Ala Thr Tyr Tyr Cys
            20                  25                  30

<210> SEQ ID NO 28
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      Polypeptide

<400> SEQUENCE: 28

Gln Gln Trp Gly Ser Tyr Pro Trp Thr
1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 29

Phe Gly Gly Gly Thr Lys Leu Glu Ile Lys Arg
1               5                   10

<210> SEQ ID NO 30
<211> LENGTH: 25
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 30

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 31

Gly Phe Ser Leu Ser Ser Tyr Gly Val Asp
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 32

Trp Val Arg Gln Pro Pro Gly Lys Gly Leu Glu Trp Leu Gly
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 33
```

Val Ile Trp Gly Gly Ser Ile Asn Tyr Asn Ser Ala Leu Met Ser
1               5                   10                  15

<210> SEQ ID NO 34
<211> LENGTH: 32
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 34

Arg Leu Ser Ile Ser Lys Asp Asn Ser Lys Ser Gln Ile Phe Leu Lys
1               5                   10                  15

Met Asn Ser Leu Gln Thr Asp Asp Thr Ala Ile Tyr Tyr Cys Thr Thr
                20                  25                  30

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 35

His Glu Asp Tyr Gly Pro Phe Ala Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 36

Trp Gly Gln Gly Thr Leu Val Thr Val Ser Ala
1               5                   10

<210> SEQ ID NO 37
<211> LENGTH: 351
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 37
caggtgcagc tgaaggagtc aggacctggc ctggtggcgc cctcacagag cctgtccatc      60
acatgcactg tctcagggtt ttcattaacc agttatggtg taagctgggc tcgccagcct     120
ccaggaaagg gtctggagtg gctgggagta atatgggtg acgggagcac aaaattatcat     180 tcagctctca tatccagact gagcatcagc aaggataact ccaagagcca agttttctta     240
aaactgaaca gtctgcaaac tgatgacaca gccacgtact actgtgccaa accggaaaac     300
tgggacggct tcgatgtctg ggcccaggg accacggtca ccgtctcctc a              351

<210> SEQ ID NO 38
<211> LENGTH: 321
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 38

```
caaattgttc tctcccagtc tccagcaatc ctgtctgcat ctccagggga gaaggtcaca    60
atgacttgca gggccagctc aagtgtaagt tacatgcact ggtaccgaca gaagccagga   120
tcctccccca aaccctggat ttatgccaca tccgacctgg cttctggagt ccctactcgc   180
ttcagtggca gtgggtctgg gacctcttac tctctcacaa tcagcagagt ggaggctgaa   240
gatgctgcca cttattactg ccagcagtgg agtagttacc cgtggacgtt cggtggaggc   300
accaagctgg aaatcaaacg g                                             321
```

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 39

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val Ser Trp Ala Arg Gln Pro Pro Gly Lys Gly Leu Glu Trp Leu
        35                  40                  45

Gly Val Ile Trp Gly Asp Gly Ser Thr Asn Tyr His Ser Ala Leu Ile
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Pro Glu Asn Trp Asp Gly Phe Asp Val Trp Gly Pro Gly Thr Thr
            100                 105                 110

Val Thr Val Ser Ser
        115
```

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 40

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Arg Gln Lys Pro Gly Ser Ser Pro Lys Pro Trp Ile Tyr
        35                  40                  45

Ala Thr Ser Asp Leu Ala Ser Gly Val Pro Thr Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Tyr Pro Trp Thr
                85                  90                  95
```

```
Phe Gly Gly Gly Thr Lys Leu Glu Ile Lys Arg
            100                 105

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 41

Gln Ile Val Leu Ser Gln Ser Pro Ala Ile Leu Ser Ala Ser Pro Gly
1               5                   10                  15

Glu Lys Val Thr Met Thr Cys
            20

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 42

Arg Ala Ser Ser Ser Val Ser Tyr Met His
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 43

Trp Tyr Arg Gln Lys Pro Gly Ser Ser Pro Lys Pro Trp Ile Tyr
1               5                   10                  15

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 44

Ala Thr Ser Asp Leu Ala Ser
1               5

<210> SEQ ID NO 45
<211> LENGTH: 31
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 45

Val Pro Thr Arg Phe Ser Gly Ser Gly Ser Gly Thr Ser Tyr Ser Leu
1               5                   10                  15

Thr Ile Ser Arg Val Glu Ala Glu Asp Ala Ala Thr Tyr Tyr Cys
            20                  25                  30
```

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 46

Gln Gln Trp Ser Ser Tyr Pro Trp Thr
1               5

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 47

Phe Gly Gly Gly Thr Lys Leu Glu Ile Lys Arg
1               5                   10

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 48

Gln Val Gln Leu Lys Glu Ser Gly Pro Gly Leu Val Ala Pro Ser Gln
1               5                   10                  15

Ser Leu Ser Ile Thr Cys Thr Val Ser
            20                  25

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 49

Gly Phe Ser Leu Thr Ser Tyr Gly Val Ser
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 50

Trp Ala Arg Gln Pro Pro Gly Lys Gly Leu Glu Trp Leu Gly
1               5                   10

<210> SEQ ID NO 51
<211> LENGTH: 16
<212> TYPE: PRT
<213> ORGANISM: Artificial Sequence
<220> FEATURE:

```
<223> OTHER INFORMATION: Description of Artificial Sequence: Synthetic
      Polypeptide

<400> SEQUENCE: 51

Val Ile Trp Gly Asp Gly Ser Thr Asn Tyr His Ser Ala Leu Ile Ser
1               5                   10                  15

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 52

Arg Leu Ser Ile Ser Lys Asp Asn Ser Lys Ser Gln Val Phe Leu Lys
1               5                   10                  15

Leu Asn Ser Leu Gln Thr Asp Asp Thr Ala Thr Tyr Tyr Cys Ala Lys
            20                  25                  30

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 53

Pro Glu Asn Trp Asp Gly Phe Asp Val
1               5

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      Polypeptide

<400> SEQUENCE: 54

Trp Gly Pro Gly Thr Thr Val Thr Val Ser Ser
1               5                   10
```